US012606839B2

(12) United States Patent
Gutierrez-Marcos

(10) Patent No.: US 12,606,839 B2
(45) Date of Patent: Apr. 21, 2026

(54) METHODS FOR ENHANCING GENOME ENGINEERING EFFICIENCY

(71) Applicant: THE UNIVERSITY OF WARWICK, Coventry (GB)

(72) Inventor: Jose F. Gutierrez-Marcos, Coventry (GB)

(73) Assignee: THE UNIVERSITY OF WARWICK, Coventry (GB)

(*) Notice: Subject to any disclaimer, the term of this patent is extended or adjusted under 35 U.S.C. 154(b) by 448 days.

(21) Appl. No.: 17/426,191

(22) PCT Filed: Jan. 28, 2020

(86) PCT No.: PCT/IB2020/000063
§ 371 (c)(1),
(2) Date: Jul. 28, 2021

(87) PCT Pub. No.: WO2020/157573
PCT Pub. Date: Aug. 6, 2020

(65) Prior Publication Data
US 2022/0112511 A1 Apr. 14, 2022

Related U.S. Application Data

(60) Provisional application No. 62/798,010, filed on Jan. 29, 2019.

(51) Int. Cl.
C12N 15/82 (2006.01)

(52) U.S. Cl.
CPC ..... C12N 15/8213 (2013.01); C12N 15/8238 (2013.01)

(58) Field of Classification Search
None
See application file for complete search history.

(56) References Cited

U.S. PATENT DOCUMENTS

| | | | |
|---|---|---|---|
| 6,528,701 B1 | 3/2003 | Wang et al. | |
| 6,825,397 B1 | 11/2004 | Lowe et al. | |
| 7,763,774 B2 | 7/2010 | Hehl et al. | |
| 7,767,801 B2 | 8/2010 | Hehl et al. | |
| 7,960,612 B2 | 6/2011 | Zhang et al. | |
| 9,476,057 B2 | 10/2016 | Samuel et al. | |
| 2008/0229439 A1 | 9/2008 | La Rosa et al. | |
| 2010/0162427 A1 | 6/2010 | Riechmann et al. | |
| 2011/0165679 A1 | 7/2011 | Gordon-Kamm et al. | |
| 2014/0219925 A1 | 8/2014 | Bertrand et al. | |
| 2014/0237681 A1 | 8/2014 | Gordon-Kamm et al. | |
| 2017/0121722 A1 | 5/2017 | Anand et al. | |
| 2017/0233756 A1 | 8/2017 | Begemann et al. | |
| 2018/0028686 A1 | 2/2018 | Brinker et al. | |
| 2018/0066271 A1* | 3/2018 | Becker ............... | C12N 15/8222 |
| 2019/0225974 A1 | 7/2019 | D'Halluin et al. | |
| 2021/0254087 A1* | 8/2021 | Lin ..................... | C12N 15/821 |
| 2021/0277407 A1 | 9/2021 | Kong et al. | |
| 2022/0025388 A1 | 1/2022 | Meng | |

| | | |
|---|---|---|
| 2023/0081632 A1 | 3/2023 | Meng |
| 2024/0191248 A1 | 6/2024 | Meng |
| 2024/0417743 A1 | 12/2024 | Meng |

FOREIGN PATENT DOCUMENTS

| | | |
|---|---|---|
| CN | 101750487 A | 6/2010 |
| CN | 101849009 A | 9/2010 |
| CN | 109879944 A | 6/2019 |
| CN | 109983122 A | 7/2019 |
| EP | 2771468 B1 | 2/2015 |
| EP | 3159413 A1 | 4/2017 |
| EP | 3009511 B1 | 5/2017 |
| EP | 3252162 A1 | 12/2017 |
| EP | 3456825 A1 | 3/2019 |
| WO | 94/18313 A1 | 8/1994 |
| WO | 95/09233 A1 | 4/1995 |
| WO | 03/004659 | 1/2003 |
| WO | 03/080809 | 10/2003 |
| WO | 2010/079430 A1 | 7/2010 |
| WO | 2011/072246 | 6/2011 |
| WO | 2011/082310 A2 | 7/2011 |
| WO | 2011/082318 A2 | 7/2011 |
| WO | 2011/146121 A1 | 11/2011 |
| WO | 2011/154393 | 12/2011 |
| WO | 2012/001527 | 1/2012 |
| WO | 2012/093833 | 7/2012 |
| WO | 2012/104729 A1 | 8/2012 |
| WO | 2012/138927 | 10/2012 |
| WO | 2012/138939 A1 | 10/2012 |
| WO | 2013/103369 A1 | 7/2013 |
| WO | 2013/103370 A1 | 7/2013 |
| WO | 2016/021973 A1 | 2/2016 |
| WO | 2016/146552 A1 | 9/2016 |

(Continued)

OTHER PUBLICATIONS

Waki et al (2011 Current Biology 21:1277-1281 (Year: 2011).*
Zhang et al., "CRISPR ribonucleoprotein-mediated genetic engineering in plants", Plant Communications, Mar. 8, 2021, vol. 2, pp. 1-13.
Nardmann et al., "The Shoot Stem Cell Niche in Angiosperms: Expression Patterns of WUS Orthologues in Rice and Maize Imply Major Modifications in the Course of Mono- and Dicot Evolution", Molecular Biology and Evolution, 2006, vol. 23, No. 12, pp. 2492-2504.
Soderlund et al., "Sequencing, Mapping, and Analysis of 27,455 Maize Full-Length cDNAs", PLoS Genetics, 2009, vol. 5, Issue 11, e1000740, pp. 1-13.

(Continued)

*Primary Examiner* — Brent T Page
(74) *Attorney, Agent, or Firm* — Troutman Pepper Locke LLP

(57) ABSTRACT

This document relates to methods and materials for genome engineering in eukaryotic cells, and particularly to methods for increasing genome engineering (i.e. transformation or genome editing) efficiency via delivery of one or more RKD2 and RKD4 genes, with genome engineering components.

40 Claims, 6 Drawing Sheets

Specification includes a Sequence Listing.

(56)　　　　　　References Cited

FOREIGN PATENT DOCUMENTS

| WO | 2016184955 A2 | 11/2016 |
|---|---|---|
| WO | 2016184989 A1 | 11/2016 |
| WO | 2017/074547 A1 | 5/2017 |
| WO | 2018042346 A2 | 3/2018 |
| WO | 2018236548 A1 | 12/2018 |
| WO | 2019/060383 A1 | 3/2019 |
| WO | 2019122360 A1 | 6/2019 |
| WO | 2019/238909 A1 | 12/2019 |
| WO | 2019238908 A1 | 12/2019 |
| WO | 2019238911 A1 | 12/2019 |

OTHER PUBLICATIONS

Tanaka et al., "The *Arabidopsis* histone deacetylases HDA6 and HDA19 contribute to the repression of embryonic properities after germination", Plant Physiology, 2008, vol. 146, No. 1, pp. 149-161.

"RWP-RK domain containing protein [Triticum aestivum]", AEB26836.1, GenBank; Aug. 5, 2011.

Li et al., "Analysis of pepper RWP-RK transcription factors", Journal of Anhui Agricultural University, 2018, vol. 45, No. 1, pp. 187-194.

Yang et al., "Trichostatin A and 5-azacytidine both cause an increase in global histone H4 acetylation and a decrease in global DNA and H3K9 methylation during mitosis in maize", BMC Plant Biology, 2010, vol. 10, No. 178, 11 pages.

Prasad et al., "*Arabidopsis* PLETHORA transcription factors control phyllotaxis", Current Biology, 2011, vol. 21, No. 13, pp. 1123-1128.

Purwestri et al., "RWP-PK Domain 3 (OsRKD3) induces somatic embryogenesis in black rice", BMC Plant Biology, 2023, vol. 23, No. 202, 15 pages.

Sprunck et al., "Elucidating small RNA pathways in *Arabidopsis thaliana* egg cells", BioRxiv, 2019, doi: https://doi.org/10.1101/525956, 39 pages.

Helenius et al., "Gene delivery into intact plants using the HeliosTM Gene Gun", Plant Molecular Biology Reporter, 2000, vol. 18, No. 3, pp. 287a-287l.

Isalan et al., "A rapid, generally applicable method to engineer zinc fingers illustrated by targeting the HIV-1 promoter", Nature Biotechnology, 2001, vol. 19, No. 7, pp. 656-660.

Liu et al. "Design of polydactyl zinc-finger proteins for unique addressing within complex genomes", Proceedings of the National Academy of Sciences, 1997, vol. 94, No. 11, pp. 5525-5530.

Boch et al., "Breaking the code of DNA binding specificity of TAL-type III effectors", Science, 2009, vol. 326, No. 5959, pp. 1509-1512.

Moscou et al., "A simple cipher governs DNA recognition by TAL effectors", Science, 2009, vol. 326, No. 5959, p. 1501.

Zetsche et al., "Cpf1 Is a Single RNA-Guided Endonuclease of a Class 2 CRISPR-Cas System", Cell, 2015, vol. 163, pp. 759-771.

Makarova et al., "An updated evolutionary classification of CRISPR-Cas systems", Nature Rev. Microbiol., 2015, vol. 13, No. 11, pp. 722-736.

Jinek et al., "A programmable dual-RNA-guided DNA endonuclease in adaptive bacterial immunity", Science, 2012, vol. 337, No. 6096, pp. 816-821.

Burstein et al., "New CRISPR-Cas systems from uncultivated microbes", Nature, 2017, vol. 542, pp. 237-241.

Jore et al., "Structural basis for CRISPR RNA-guided DNA recognition by Cascadek", Nature Structural & Molecular Biology, 2011, vol. 18, No. 5, pp. 529-536.

Gaudelli et al., "Programmable base editing of A• T to G• C in genomic DNA without DNA cleavage", Nature, 2017, vol. 551, No. 7681, pp. 464.

Sterner et al., "Acetylation of histones and transcription-related factors", Microbiology and Molecular Biology Reviews, 2000, vol. 64, No. 2, pp. 435-459.

Zhang et al., "Transcription regulation by histone methylation: interplay between different covalent modifications of the core histone tails", Genes & Development, 2001, vol. 15, No. 18, pp. 2343-2360.

Shilatifard, "Chromatin modifications by methylation and ubiquitination: implications in the regulation of gene expression", Annu. Rev. Biochem., 2006, vol. 75, pp. 243-269.

Nowak et al., "Phosphorylation of histone H3: a balancing act between chromosome condensation and transcriptional activation", Trends in Genetics, 2004, vol. 20 , No. 4, pp. 214-220.

Nathan et al., "Histone sumoylation is a negative regulator in *Saccharomyces cerevisiae* and shows dynamic interplay with positive-acting histone modifications", Genes & Development, 2006, vol. 20, No. 8, pp. 966-976.

Hassa et al., "Nuclear ADP-ribosylation reactions in mammalian cells: where are we today and where are we going?", Microbiology and Molecular Biology Reviews, 2006, vol. 70, No. 3, pp. 789-829.

Andrews et al., "Nucleosome structure(s) and stability: Variations on a theme", Annu. Rev. Biophys., 2011, vol. 40, pp. 99-117.

Bannister et al., "Regulation of chromatin by histone modifications", Cell Research, 2011, vol. 21, pp. 381-395.

Zhang et al., "An epigenetic perspective on developmental regulation of seed genes", Molecular Plant, 2009, vol. 2, No. 4, pp. 610-627.

Miguel et al., "An epigenetic view of plant cells cultured in vitro: somacional variation and beyond", Journal of Experimental Botany, 2011, vol. 62, pp. 3713-3725.

Li et al., "The Histone Deacetylase Inhibitor Trichostatin A Promotes Totipotency In the Male Gametophyte", The Plant Cell, 2014, vol. 26, pp. 195-209.

Waki et al., "The *Arabidopsis* RWP-RK protein RKD4 triggers gene expression and pattern formation in early embryogenesis", Current Biology, 2011, vol. 21, No. 15, pp. 1277-1281.

El Ouakfaoui et al., "Control of somatic embryogenesis and embryo development by AP2 transcription factors", Plant Molecular Biology, 2010, vol. 74(4-5), pp. 313-326.

Rice et al., "EMBOSS: The European Molecular Biology Open Software Suite", Trends in Genetics, 2000, vol. 16, No. 6, pp. 276-277.

U.S. Appl. No. 62/609,508, filed Dec. 22, 2017.

International Search Report and Written Opinion issued in International Application No. PCT/EP2019/065643 dated Oct. 2, 2019.

Svitashev et al., "Genome editing in maize directed by CRISPR-Cas9 ribonucleoprotein complexes", Nature Communications, vol. 7, 2016, p. 13274.

Lowe et al., "Morphogenic Regulators Baby boom and Wuschel Improve Monocot Transformation", The Plant Cell, vol. 28, No. 9, 2016, pp. 1998-2015.

Bouchabke-Coussa et al., "Wuschel overexpression promotes somatic embryogenesis and induces organogenesis in cotton (*Gossypium hirsutum* L.) tissues cultured in vitro", Plant Cell Reports, 2013, vol. 32, No. 5, pp. 675-686.

International Search Report and Written Opinion issued in International Application No. PCT/EP2019/065645 dated Oct. 7, 2019.

Database EMBL [Online] May 1, 2009 (May 1, 2009), "Ginkgo biloba (maidenhair tree) putative wuschel homeobox protein WUS ID—CAT02906; sv 1.; linear; mRNA; STD; PLN; 786 BP", XP002794173, retrieved from EBI accession No. EMBL:CAT02906 sequence.

Database EMBL [Online] May 1, 2009 (May 1, 2009), "Ginkgo biloba mRNA for putative wuschel homeobox protein WUS (wus gene)", XP002794174, retrieved from EBI accession No. EMBL:FM882128 Database accession No. FM882128 sequence.

International Search Report and Written Opinion issued in International Application No. PCT/EP2019/065647 dated Nov. 29, 2019.

International Search Report and Written Opinion issued in International Application No. PCT/IB2020/000063 dated Jun. 16, 2020.

Koszegi et al., "Members of the RKD transcription factor family induce an egg cell-like gene expression program", The Plant Journal, 2011, vol. 67, No. 2, pp. 280-291.

Kol et al., "An Evolutionarily Conserved Plant RKD Factor Controls Germ Cell Differentiation", Current Biology, 2016, vol. 26, No. 13, pp. 1775-1781.

(56)                References Cited

OTHER PUBLICATIONS

Zuo et al., "An estrogen receptor-based transactivator XVE mediates highly inducible gene expression in transgenic plants", The Plant Journal, 2000, vol. 24, No. 2, pp. 265-273.

Samalova et al., "pOp6/LhGR: a stringently regulated and highly responsive dexamethasone-inducible gene expression system for tobacco", The Plant Journal, 2005, vol. 41, No. 6, pp. 919-935.

Durr et al., "Highly efficient heritable targeted deletions of gene clusters and non-coding regulatory regions in Arabidopsis using CRISPR/Cas9", Scientific Reports, 2018, vol. 8, 4443, 11 pages.

Zuo et al., "Chemical-inducible systems for regulated expression of plant genes", Current Opinion in Biotechnology, 2000, vol. 11, No. 2, pp. 146-151.

Milne et al., "An Approach to gene-specific transcription inhibition using oligonucleotides complementary to the template strand of the open complex", PNAS, 2000, vol. 97, No. 7, pp. 3136-3141.

Zhang et al., "Predicting DNA Hybridization Kinetics from Sequence", Nature Chemistry, 2018, vol. 10, pp. 91-98.

Zhang et al., "A Two-Step Model for de Novo Activation of WUSCHEL during Plant Shoot Regeneration", The Plant Cell, 2017, vol. 29, pp. 1073-1087.

Nardmann et al., Accession CAT02906, published 2009.

Kareem et al., "PLETHORA Genes Control Regeneration by a Two-step Mechanism", Curr Biol., 2015, vol. 25, No. 8, pp. 1017-1030.

Lowe et al., "Rapid genotype "independent" Zea mays L. (maize) transformation via direct somatic embryogenesis", In Vitro Cellular & Developmental Biology—Plant, 2018, vol. 54(8), pp. 240-252.

Komor et al. Programmable editing of a target base in genomic DNA without double-stranded DNA cleavage. Nature 2016, vol. 533, pp. 420-424.

Zong et al., "Precise base editing in rice, wheat and maize with a Cas9-cytidine deaminase fusion", Nat. Biotechnol., 2017, vol. 35, pp. 438-440.

Yan et al., "Highly EfficientA• T to G• C Base Editing by Cas9n-Guided IRNA Adenosine Deaminase in Rice", Molecular Plant, Apr. 2, 2018, vol. 11, issue 4, pp. 631-634.

Hua et al., "Precise A• T to G• C Base Editing in the Rice Genome", Molecular Plant, Apr. 2018, vol. 11(4): pp. 627-630.

Anzalone et al., "Search and replace genome editing without double-strand breaks or donor DNA", Nature, Oct. 21, 2019, vol. 576, pp. 149-157.

Smith et al., "Identification of common molecular subsequences" Journal of Molecular Biology, 1981, vol. 147, No. 1, pp. 195-197.

Mayer et al., "Role of WUSCHEL in regulating stem cell fate in the Arabidopsis shoot meristem", Cell, Dec. 11, 1998, vol. 95, pp. 805-815.

Yadav et al., "WUSCHEL protein movement mediates stem cell homeostasis in the Arabidopsis shoot apex", Genes Dev., 2011, vol. 25, pp. 2025-2030.

Laux, et al., "The WUSCHEL gene is required for shoot and floral meristem integrity in Arabidopsis", Development, 1996, vol. 122, pp. 87-96.

Leibfried et al., "WUSCHEL controls meristem function by direct regulation of cytokinin-inducible response regulators", Nature, Dec. 22, 2005, vol. 438(7071), pp. 1172-1175.

Hofmann, "A Breakthrough in Monocot Transformation Methods", The Plant Cell, Sep. 2016, vol. 28: p. 1989.

Nic-Can et al., "New Insights into Somatic Embryogenesis: Leafy COTYLEDON1, Baby BOOM1 and WUSCHEL-Related HOMEO-BOX4 Are Epigenetically Regulated in Coffea canephora", PLoS One, Aug. 2013, vol. 8(8), 31 pages, e72160. PMID: 23977240.

Ling Min et al., "Leafy COTYLEDON1-CASEIN Kinase I-TCP15-Phytochrome Interacting FACTOR4 Network Regulates Somatic Embryogenesis by Regulating Auxin Homeostasis", Plant Physiology, Dec. 2015, vol. 169, pp. 2805-2821.

Cagliari et al., "New insights on the evolution of Leafy cotyledon1 (LEC1) type genes in vascular plants", Genomics, 2014, vol. 103, pp. 380-387.

Kim et al., "The AtGRF family of putative transcription factors is involved in leaf and cotyledon growth in Arabidopsis", The Plant Journal, 2003, vol. 36, pp. 94-104.

Choi et al., "Whole Genome Analysis of the OsGRF Gene Family Encoding Plant Specific Putative Transcription Activators in Rice (Oryza sativa L.)", Plant Cell Physiol, 2004, vol. 45(7): pp. 897-904.

Ellerström et al., "Etopic Expression of Effector of Transcription perturbs gibberellin-mediated plant developmental proceses", Plant Molecular Biology, 2005, vol. 59: pp. 663-681.

Aida et al., "The PLETHORA genes mediate patterning of the Arabidopsis root stem cell niche", Cell, 2004, vol. 119: pp. 109-120.

Mahönen et al., "PLETHORA gradient formation mechanism separates auxin responses", Nature, 2014, vol. 515: pp. 125-129.

Santuari et al., "The PLETHORA Gene Regulatory Network Guides Growth and Cell Differentiation in Arabidopsis Roots", The Plant Cell, Dec. 2016, vol. 28: pp. 2937-2951.

Ravi et al., "Haploid plants produced by centromere-mediated genome elimination", Nature, 2010, vol. 464, pp. 615-619.

International Search Report and Written Opinion issued in PCT/EP2021/054805 dated May 21, 2021.

Collins et al. Accession No. GO662999, 2010.

Hortsman et al., 2014, "Antigumenta-Like 5 protiends: hubs in a plethora of networks", Trends in Plant Science, vol. 19, No. 3, pp. 146-157.

Zhang et al., "Chemical probes in plant epigenetics studies", Plant Signaling & Behavoir, 2013, vol. 8, No. 9, e25364.

Nasti et al., 2022, Defining the Parameters to Improve Plant Regeneration with Developmental Regulators, BioRxiv.

Guo et al., 2004, "Protein tolerance to random amino acid change", Proceedings of the Naitonal Academy of Sciences, vol. 101, No. 25, pp. 9205-9210.

Horlbeck et al., 2016, "Nucleosomes impede Cas9 access to DNA in vivo and in vitro", elife, vol. 5, e12677.

Definition of derivative—NCI Dictionary of Cancer Terms—NCI (https://www.cancer.gov/publications/dictionaries/cancer-terms/def/derivative) viewed on Jan. 24, 2023 (Year: 2023).

Variant Definition & Meaning—Merriam-Webster (https://www.meriamp-webster.com/dictionary/variant) viewed on Jan. 24, 2023 (Year: 2023).

Tsuwamoto et al., "Arabidopsis EMBRYOMAKER encoding an AP2 domain transcription factor plays a key role in developmental change from vegetative to embryonic phase", Plant Molecular Biology, 2010, vol. 73, pp. 481-492.

Horstman et al., "A transcriptional view on somatic embryogenesis", Regeneration, 2017, vol. 4, No. 4, pp. 201-216.

Craft et al., "New pOp/LhG4 vectors for stringent glucocorticoid—dependent transgene expression in Arabidopsis", The Plant Journal, 2005, vol. 41, No. 6, pp. 899-918.

https://www.uniprot.org/uniprot/Q98292; May 2009.

Du et al., "PLETHORA transcription factors orchestrate de novo organ patterning during Arabidopsis lateral root outgrowth", PNAS 2017, vol. 114, No. 44, pp. 11709-11714. https://doi.org/10.1073/pnas.1714410114.

International Search Report and Written Opinion issued in International Application No. PCT/EP2021/054799 dated May 31, 2021.

Gordon-Kamm et al., "Using morphogenic genes to improve recovery and regeneration of transgenic plants", Plants, 2019, vol. 8, No. 2, p. 38; 18 pages.

Potsenkovskala et al., "Novel NF-Y genes expressed during somatic embryogenesis in Medicago truncatula", Plant Gene, 2022, vol. 31, 100364; 12 pages.

GenBank Accession AGL53583.1, "Wuschel homeobox protein WOX5 [Picea abies]" dated Jun. 20, 2013, https://www.ncbi.nlm.nih.gov/protein/AGL53583.1/.

Zhang et al., "Overexpression analysis of plant transcription factors", Current Opinion In Plant Biology, 2003, vol. 6, No. 5, pp. 430-440.

Eld et al., "CRISPR base editors: genome editing without double-stranded breaks", Biochemical Journal, 2018, vol. 475, No. 11, pp. 1955-1964.

(56)        References Cited

OTHER PUBLICATIONS

Laforest et al., "Advances in Delivery Mechanisms of CRISPR Gene-Editing Reagents in Plants", Frontiers in Genome Editing, 2022, vol. 4, Article 830178; 10 pages.

Lv et al., "Nanoparticle-mediated gene transformation strategies for plant genetic engineering", The Plant Journal, 2020, vol. 104, pp. 880-891.

Sun et al., "Delivery of Abscisic Acid to Plants Using Glutathione Responsive Mesoporous Silica Nanoparticles", Journal of Nanoscience and Nanotechnology, 2018, vol. 18, No. 3, pp. 1615-1625.

Joshi et al., "Gold Nanoparticles as Carriers for Efficient Transmucosal Insulin Delivery", Langmuir, 2006, vol. 22, No. 1, pp. 300-305.

Klein et al., "Factors Influencing Gene Delivery into *Zea mays* Cells by High-Velocity Microprojectiles", Bio/Technology, 1988, vol. 6, pp. 559-563.

Ikeda et al., "*Arabidosis* Wuschel Is a Bifunctional Transcription Factor That Acts as a Repressor in Stem Cell Regulation and as an Activator in Floral Patterning", The Plant Cell, 2009, vol. 21, pp. 3493-3505.

Bortesi et al., "The CRISPR/Cas9 system for plant genome editing and beyond", Biotechnology Advances, 2015, vol. 33, pp. 41-52.

Li et al., "Plant Specific Histone Deacetylases HDT1/2 Regulate Gibberellin 2-Oxidase2 Expression to Control Arabidopsis Root Meritstem Cell Number", The Plant Calle, 2017, vol. 29, pp. 2183-2196.

He et al., "Regulation and function of DNA methylaticn in plants and animals", Cell Research, 2011, vol. 21, pp. 442-465.

Ma et al., "Comprehensive insights on how 2,4-dichlorophenoxyacetic acid retards senescence in post-harvest citrus fruits using transcriptomic and proteomic approaches", Journal of Experimental Boanty, 2014, vol. 65, No. 1, pp. 61-74.

Wang et al., "Chapter 13: Applications of Glaod Nanoparticles in cancer Imaging and Treatment", in Book: Noble and Previous Metals-Properties, Nanoscale effects and applications, IntechtOpen, 2017, pp. 291-309 http://dx.doi.org/10.5772/intechopen.70901.

Tsuji et al., "A New Antifungal Antibotic, Trichostatin", The Journal of Antibotics, 1976, vol. 29, No. 1, 49-14691, pp. 1-6.

Parveen et al., "Nanoparticles: a boon to drug delivery, therapeutics, diagnostic and imaging", Nanomedicine: Nanotechnology, Biology, and Medicine, 2012, vol. 8, pp. 147-166.

* cited by examiner

Embryogenesis induced
by application of
30uM β-estradiol

Shoot and root
development

Photomorphogenesis
after light exposure

Seedling
establishment

METHODS FOR ENHANCING GENOME ENGINEERING EFFICIENCY

CROSS-REFERENCE TO RELATED APPLICATIONS

This application is a U.S. National Phase of International Patent Application No. PCT/IB2020/000063, filed on Jan. 28, 2020, which claims priority to U.S. Provisional Application No. 62/798,010, filed on Jan. 29, 2019. The entire contents of these applications are incorporated herein by reference in their entirety.

TECHNICAL FIELD

Described herein are novel methods and materials for genome engineering in eukaryotic cells, and particularly methods for increasing genome engineering (i.e., transformation or genome editing) efficiency via delivery of nucleic acids encoding RKD2 and/or RKD4, with genome engineering components.

SEQUENCE LISTING

The instant application contains a Sequence Listing which has been submitted electronically in ASCII format and is hereby incorporated by reference in its entirety. Said ASCII copy, created on Jan. 28, 2020, is named 245761.000094.sequence.listing.txt and is 73,290 bytes in size.

BACKGROUND OF THE INVENTION

Traditional breeding has provided domesticated plants and animals, while modern biotechnology, in particular genome engineering, is expanding breeding capability and enabling improvements that are not possible with only traditional crossing of close species. Using biotechnology, various traits, such as high-yield, herbicide tolerance and pest resistance, have been introduced into crops, resulting in dramatic advances in global agriculture and food security. However, the presence of foreign DNA in such products of biotechnology can trigger biosafety and environmental concerns.

By segregating out any integrated DNA, genome-editing technology can be used to generate a site-specific modification of the target genome without the presence of foreign DNA in the end plants. Moreover, by transient expression, genome editing can involve transient editing activity to create site-specific modification without DNA integration at any points of process. The genome-edited plants, especially those derived from the transient activity, would be significantly different from the conventional genome modified plants, and may not be regulated as genetically modified (GM) plants. Genome editing techniques, especially via a transient editing approach, thus can provide a highly accurate, safe and powerful plant breeding and development tool in agriculture.

Genome engineering based on transient activity however faces more challenges. Compared with stable transformation, transient engineering generally results in fewer modified cells. Without an integrated selectable marker, it is highly challenging to identify the engineered cells and achieve homogenous modification in the regenerated plants. These challenges stand in the way of routine implementation of transient gene editing as a breeding tool for plant improvement. Novel methods and materials that enhance genome engineering efficiency are thus highly desirable.

SUMMARY OF THE INVENTION

In one aspect is provided a method for genetic modification in a plant cell, the method comprising
- (a) introducing into the plant cell
  - (i) a nucleic acid comprising a polynucleotide sequence encoding the RKD2 polypeptide or the RKD4 polypeptide, a recombinant gene comprising the nucleic acid, or a DNA construct comprising the nucleic acid; and
  - (ii) a transgene of interest and/or a genome engineering component;
- (b) optionally, cultivating the plant cell under conditions allowing the synthesis of the RKD2 polypeptide or the RKD4 polypeptide from the nucleic acid after chemical induction; and
- (c) optionally, cultivating the plant cell under conditions allowing the genetic modification of the genome of said plant cell by integration of the transgene of interest and activity of the genome engineering component in the presence of the RKD2 polypeptide or the RKD4 polypeptide;

where polynucleotide sequence encoding the RKD2 polypeptide or the RKD4 polypeptide is operably linked to a heterologous promoter, which is either directly chemically inducible or indirectly chemically inducible preferably via an intermediate transcription factor.

In some embodiments, the method is effective to improve the efficiency of plant regeneration. In some embodiments, the method is effective to increase the regeneration ability of the plant cell. In some embodiments, in step (b) the RKD2 polypeptide or the RKD4 polypeptide is synthesized from the nucleic acid upon direct or indirect chemical induction of the heterologous promoter, preferably upon addition of β-estradiol or a glucocorticoid such as dexamethasone to the plant cell.

In some embodiments, the heterologous promoter is the XVE/OLexA system for chemical β-estradiol inducibility. In various embodiments, the XVE/OLexA system comprises the nucleic acid sequence of SEQ ID NO: 22, or a nucleic acid sequence at least 90%, 91%, 92%, 93%, 94%, 95%, 96%, 97%, 98%, 99% identical to SEQ ID NO: 22.

In some embodiments, the heterologous promoter is an inducible bidirectional promoter. In various embodiments, the inducible bidirectional promoter is operably linked to a second nucleic acid sequence encoding a desired polypeptide. In various embodiments, the second nucleic acid sequence comprises a reporter gene and a polynucleotide encoding a reporter protein. In some embodiments, the reporter is GUS or tdTomato.

In various embodiments, the inducible bidirectional promoter is a dexamethasone inducible promoter. In some specific embodiments, the promoter is pOp1, pOp2, pOp4 or pOp6. In some specific embodiments, the pOp6 comprises the nucleic acid sequence of SEQ ID NO: 15, or a nucleic acid sequence at least 90%, 91%, 92%, 93%, 94%, 95%, 96%, 97%, 98%, 99% identical to SEQ ID NO: 15.

In some embodiments, in step (a) (i) a further nucleic acid comprising a polynucleotide sequence encoding a transcription factor operably linked to a strong constitutive promoter is introduced into the plant cell, wherein the transcription factor activates pOp6 upon binding to dexamethasone. In specific embodiments, the transcription factor is LhGR or LhG4. In some embodiments, the LhGR has the amino acid sequence of SEQ ID NO: 17, or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 17; or wherein the nucleic acid encoding LhGR comprises the coding sequence of SEQ ID NO: 16, or a coding sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 16.

In some embodiments, the strong constitutive promoter is a ubiquitin promoter or a double 35S promoter. In some specific embodiments, the double 35S promoter comprises the nucleotide sequence of SEQ ID NO: 21, or a nucleotide sequence at least 90%, 91%, 92%, 93%, 94%, 95%, 96%, 97%, 98%, 99% identical to SEQ ID NO: 21. In some specific embodiments, the ubiquitin promoter comprises the nucleotide sequence of SEQ ID NO: 23, or a nucleotide sequence at least 90%, 91%, 92%, 93%, 94%, 95%, 96%, 97%, 98%, 99% identical to SEQ ID NO: 23. In some specific embodiments, the ubiquitin promoter comprises additionally a ubiquitin intron comprising the nucleotide sequence of SEQ ID NO: 20, or a nucleotide sequence at least 90%, 91%, 92%, 93%, 94%, 95%, 96%, 97%, 98%, 99% identical to SEQ ID NO: 20.

In some embodiments, the plant cell is cultivated under conditions allowing the genetic modification of the genome of said plant cell by integration of the transgene of interest and activity of the genome engineering component in the presence of the RKD2 polypeptide or the RKD4 polypeptide. In some specific embodiments, the cultivated plant cell does not express the reporter gene in the absence of a chemical agent effective to induce the chemically-inducible promoter. In some embodiments, the plant cell is cultivated to yield an embryonic structure. In some embodiments, the embryonic structure is cultivated to yield a regenerated plant.

In various embodiments, the RKD2 polypeptide or the RKD4 polypeptide is transiently present, transiently active and/or transiently expressed in the plant cell, and/or the nucleic acid encoding the RKD2 polypeptide is transiently present, transiently active and/or transiently expressed in the plant cell, or the nucleic acid encoding the RKD4 polypeptide is transiently present, transiently active and/or transiently expressed in the plant cell.

In various embodiments, the RKD2 polypeptide comprises the amino acid sequence of SEQ ID NO: 5, or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 5; or the nucleic acid encoding the RKD2 polypeptide encodes the amino acid sequence of SEQ ID NO: 5, or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 5.

In various embodiments, the RKD4 polypeptide comprises the amino acid sequence of SEQ ID NO: 2, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2; or the nucleic acid encoding the RKD4 polypeptide encodes the amino acid sequence of SEQ ID NO: 2, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2.

In some embodiments, the nucleic acid encoding the RKD2 polypeptide comprises a nucleic acid having a coding sequence selected from the group consisting of:

a) a nucleic acid comprising the nucleotide sequence of SEQ ID NO: 3 or 4;

b) a nucleic acid comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 3 or 4; and c) a nucleic acid hybridizing with the complementary strand of the nucleic acid as defined in a) or b) under stringent hybridization conditions.

In some embodiments, the nucleic acid encoding the RKD4 polypeptide comprises a nucleic acid having a coding sequence selected from the group consisting of:

a) a nucleic acid comprising the nucleotide sequence of SEQ ID NO: 1;

b) a nucleic acid comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1; and c) a nucleic acid hybridizing with the complementary strand of the nucleic acid as defined in (1) or (2) under stringent hybridization conditions.

In some embodiments, the genome engineering component comprises a) an enzyme inducing a double-stranded break (DSB) or a nucleic acid encoding same, and optionally a repair nucleic acid molecule, wherein the DSB-inducing enzyme preferably recognizes a predetermined site in the genome of said cell;

b) an enzyme inducing a single-stranded break (SSB) or a nucleic acid encoding same, and optionally a repair nucleic acid molecule, wherein the SSB-inducing enzyme preferably recognizes a predetermined site in the genome of said cell;

c) a base editor enzyme, optionally fused to a disarmed DSB- or SSB-inducing enzyme, wherein the base editor enzyme preferably recognizes a predetermined site in the genome of said cell; or d) an enzyme effecting DNA methylation, histone acetylation, histone methylation, histone ubiquitination, histone phosphorylation, histone ribosylation or histone citrullination, optionally fused to a disarmed DSB- or SSB-inducing enzyme, wherein the enzyme preferably recognizes a predetermined site in the genome of said cell.

In some embodiments, the genome engineering component comprising a DSB- or SSB-inducing enzyme or a variant thereof is a CRISPR/Cas endonuclease, a CRISPR/Cas9 endonuclease, a CRISPR/Cpf1 endonuclease, a CRISPR/Csm1 endonuclease, a CRISPR/MAD7 endonuclease, a CRISPR/CasX endonuclease, a CRISPR/CasY endonuclease, a zinc finger nuclease (ZFN), a homing endonuclease, a meganuclease, or a TAL effector nuclease.

In some embodiments, the activity of the genome engineering component in step (c) comprises inducing one or more double-stranded breaks in the genome of the plant cell, one or more single strand breaks in the genome of the plant cell, one or more base editing events in the genome of the plant cell, or one or more of DNA methylation, histone acetylation, histone methylation, histone ubiquitination, histone phosphorylation, histone sumoylation, histone ribosylation or histone citrullination in the genome of the plant cell. In specific embodiments, the induction of one or more double-stranded breaks or one or more single strand breaks is followed by non-homologous end joining (NHEJ) and/or by homology directed repair of the break(s) though a homologous recombination mechanism (HDR).

In some embodiments, the transgene in step (a) (ii) is selected from the group consisting of a gene encoding resistance or tolerance to abiotic stress, including drought stress, osmotic stress, heat stress, cold stress, oxidative stress, heavy metal stress, nitrogen deficiency, phosphate deficiency, salt stress or waterlogging, herbicide resistance, including resistance to glyphosate, glufosinate/phosphinotricin, hygromycin, protoporphyrinogen oxidase (PPO) inhibitors, ALS inhibitors, and Dicamba, a gene encoding resistance or tolerance to biotic stress, including a viral resistance gene, a fungal resistance gene, a bacterial resistance gene, an insect resistance gene, or a gene encoding a yield related trait, including lodging resistance, flowering time, shattering resistance, seed color, endosperm composition, or nutritional content.

In some embodiments, in step (c) the modification of said genome is selected from i) a replacement of at least one nucleotide;

ii) a deletion of at least one nucleotide;

iii) an insertion of at least one nucleotide;

iv) a change of the DNA methylation;

v) a change in histone acetylation, histone methylation, histone ubiquitination, histone phosphorylation, histone sumoylation, histone ribosylation or histone citrullination; and vi) any combination of i)-v).

In various embodiments, the method is effective to promote cell proliferation or cell regeneration preferably after genetic modification. In various embodiments, the method is effective to induce embryogenesis from a single cell preferably after genetic modification. In various embodiments, the method is effective to increase the stable transformation efficiency of the transgene into the plant cell. In various embodiments, the method is effective to increase the efficiency of the genome engineering component to edit the genome of the plant cell.

In another aspect is provided a genetically modified plant cell obtained or obtainable according to the method of any one of the above aspects and embodiments. Also provided is a plant or a plant part comprising the genetically modified plant cell.

In yet another aspect is provided a plant cell comprising a) a polynucleotide encoding the RKD2 polypeptide; or a polynucleotide encoding the RKD4 polypeptide; and b) a transgene of interest and/or a genome engineering component;

where the polynucleotide encoding the RKD2 polypeptide or the RKD4 polypeptide is operably linked to a heterologous promoter, which is either directly chemically inducible or indirectly chemically inducible preferably via an intermediate transcription factor.

In another aspect is provided a plant cell comprising a DNA construct, where the DNA construct comprises a) a nucleic acid comprising a polynucleotide encoding the RKD2 or RKD4 polypeptide operably linked to a chemically inducible bidirectional promoter, b) a reporter gene operably linked to the bidirectional promoter, and c) a third recombinant gene encoding a transcription factor operably linked to a strong constitutive promoter.

In another aspect is provided a method for producing a genetically modified plant, comprising the steps:

(a) genetically modifying a plant cell according to any of the above methods, and (b) regenerating a plant from the modified plant cell of step (a).

In some embodiments, the produced plant does not contain any of the genome engineering components stably integrated into the genome of the plant. Also provided is a genetically modified plant or a part thereof obtained or obtainable by the method.

In another aspect is provided the use of a nucleic acid comprising a polynucleotide encoding the RKD2 polypeptide or the RKD4 polypeptide, a recombinant gene comprising the nucleic acid, a DNA construct comprising the nucleic acid for improving the efficiency of plant regeneration or increasing the regeneration ability of a plant cell upon chemical induction, where the polynucleotide encoding the RKD2 polypeptide or the RKD4 polypeptide is operably linked to a heterologous promoter, which is either directly chemically inducible or indirectly chemically inducible preferably via an intermediate transcription factor.

DETAILED DESCRIPTION

Definitions

Figure 1:
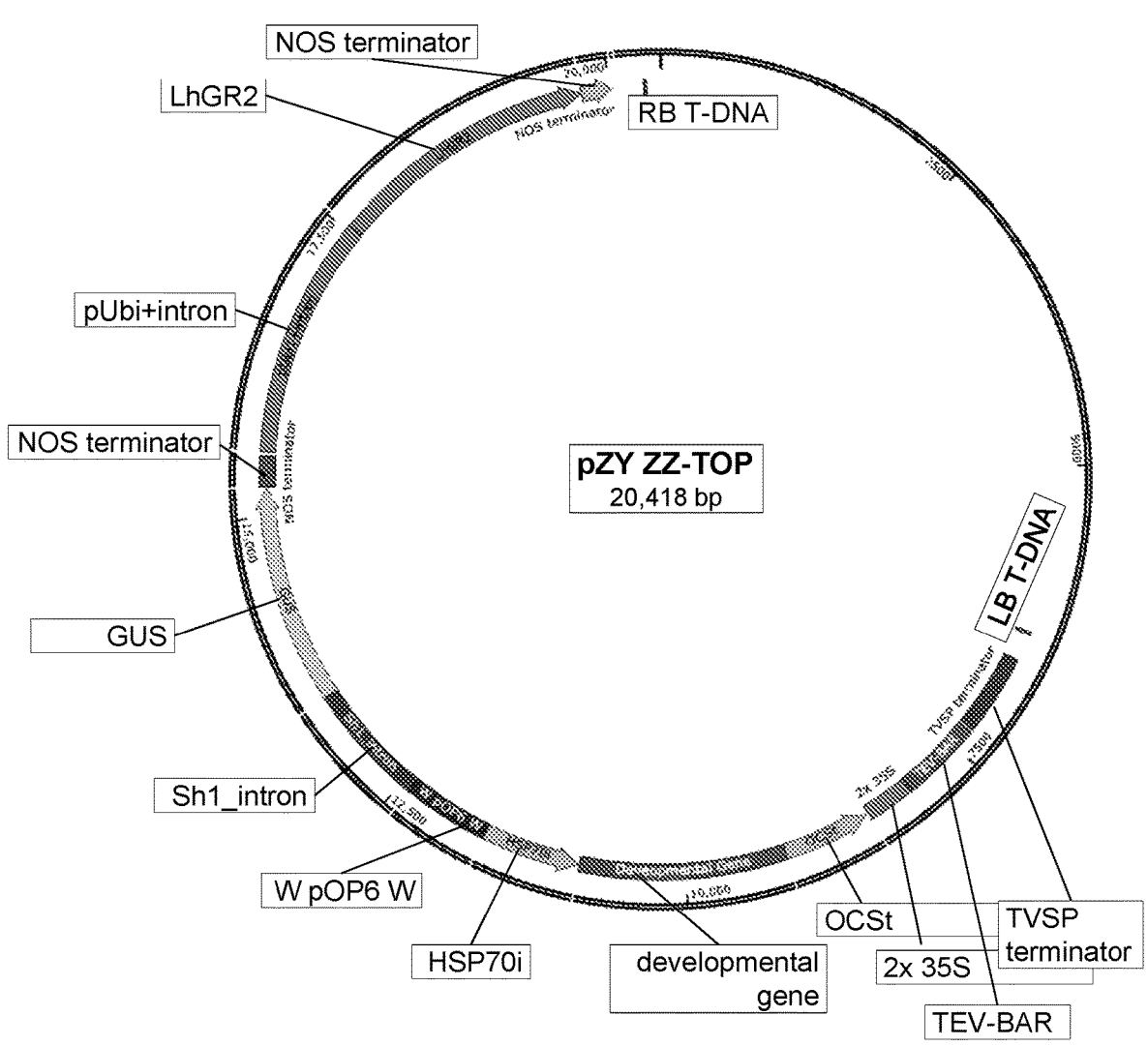
FIG. 1 shows a map of the gene expression vector pZY ZZ-TOP carrying a pOp6/LhGR system for chemical dexamethasone (Dex) inducibility of expression of GUS and a developmental gene of interest. The plasmid comprises a pOp6 chemically-inducible promoter. Upon dexamethasone exposure, both a developmental gene and a GUS reporter gene would be expressed. pZY ZZ-TOP also comprises the gene LhGR operably linked to a ubiquitin promoter. LhGR enters the nucleus in the presence of dexamethasone and activates pOp6.

Unless defined otherwise, technical and scientific terms used herein have the same meaning as commonly understood by one of ordinary skill in the art to which this invention belongs.

As used in the context of the present application, the term "about" means +/−10% of the recited value, preferably +/−5% of the recited value. For example, about 100 nucleotides (nt) shall be understood as a value between 90 and 110 nt, preferably between 95 and 105 nt.

The regeneration of transformed or gene edited plant cells may include the process of somatic embryogenesis, which is an artificial process in which a plant or embryo is derived from a single somatic cell or group of somatic cells. Somatic embryos are formed from plant cells that are not normally involved in the development of embryos, i.e. plant tissue like buds, leaves, shoots etc. Applications of this process may include: clonal propagation of genetically uniform plant material; elimination of viruses; provision of source tissue for genetic transformation; generation of whole plants from single cells, such as protoplasts; development of synthetic seed technology. Cells derived from competent source tissue may be cultured to form a callus. Plant growth regulators like auxins or cytokinines in the tissue culture medium can be manipulated to induce callus formation and subsequently changed to induce embryos to form from the callus. Somatic embryogenesis has been described to occur in two ways: directly or indirectly. Direct embryogenesis occurs when embryos are started directly from explant tissue creating an identical clone. Indirect embryogenesis occurs when explants produced undifferentiated, or partially differentiated, cells (i.e. callus) which then is maintained or differentiated into plant tissues such as leaf, stem, or roots.

The term "transgenic" as used according to the present disclosure refers to a plant, plant cell, tissue, organ or material which comprises a gene or a genetic construct, comprising a "transgene" that has been transferred into the plant, the plant cell, tissue organ or material by natural means or by means of transformation techniques from another organism. The term "transgene" comprises a nucleic acid sequence, including DNA or RNA, or an amino acid sequence, or a combination or mixture thereof. Therefore, the term "transgene" is not restricted to a sequence commonly identified as "gene", i.e. a sequence encoding protein. It can also refer, for example, to a non-protein encoding DNA or RNA sequence. Therefore, the term "transgenic"

generally implies that the respective nucleic acid or amino acid sequence is not naturally present in the respective target cell, including a plant, plant cell, tissue, organ or material. The terms "transgene" or "transgenic" as used herein thus refer to a nucleic acid sequence or an amino acid sequence that is taken from the genome of one organism, or produced synthetically, and which is then introduced into another organism, in a transient or a stable way, by artificial techniques of molecular biology, genetics and the like. A "plant material" as used herein refers to any material which can be obtained from a plant during any developmental stage. The plant material can be obtained either in planta or from an in vitro culture of the plant or a plant tissue or organ thereof. The term thus comprises plant cells, tissues and organs as well as developed plant structures as well as sub-cellular components like nucleic acids, polypeptides and all chemical plant substances or metabolites which can be found within a plant cell or compartment and/or which can be produced by the plant, or which can be obtained from an extract of any plant cell, tissue or a plant in any developmental stage. The term also comprises a derivative of the plant material, e.g., a protoplast, derived from at least one plant cell comprised by the plant material. The term therefore also comprises meristematic cells or a meristematic tissue of a plant.

The term "genome engineering" is used herein, refers to strategies and techniques for the genetic modification of any genetic information or genome of a plant cell, comprising genome transformation, genome editing. As such "genome editing" refers to techniques for the targeted, specific modification of any genetic information or genome of a plant cell. As such, "genome engineering" and "genome editing" include editing of a gene-encoding region, and also editing of regions other than gene encoding regions of a genome. These further comprise the editing or engineering of the nuclear (if present) as well as other genetic information of a plant cell. Furthermore, "genome engineering" also comprises an epigenetic editing or engineering, i.e., the targeted modification of, e.g., methylation, histone modification or of non-coding RNAs possibly causing heritable changes in gene expression.

The term "genome editing" as used herein refers to strategies and techniques for the targeted, specific modification of any genetic information or genome of a plant cell, including the editing of regions other than gene encoding regions of a genome, such as intronic sequences, non-coding RNAs, miRNAs, sequences of regulatory elements like promoter, terminator, transcription activator binding sites, cis or trans acting elements. Additionally, "genome editing" may comprise base editing for targeted replacement of single nucleobases. It can further comprise the editing of the nuclear genome as well as other genetic information of a plant cell, i.e., mitochondrial genome or chloroplast genome as well as miRNA, pre-mRNA or mRNA. Furthermore, "genome editing" may comprise an epigenetic editing or engineering, i.e., the targeted modification of, e.g., DNA methylation or histone modification, such as histone acetylation, histone methylation, histone ubiquitination, histone phosphorylation, histone sumoylation, histone ribosylation or histone citrullination, possibly causing heritable changes in gene expression. "Genome editing" may also comprise an epigenetic editing or engineering of non-coding RNAs possibly causing heritable changes in gene expression.

A "base editor" as used herein refers to a protein or a fragment thereof having the same catalytic activity as the protein it is derived from, which protein or fragment thereof, alone or when provided as molecular complex referred to as base editing complex herein. A base editor has the capacity to mediate a targeted base modification, i.e., the conversion of a base of interest resulting in a point mutation of interest which in turn can result in a targeted mutation, if the base conversion does not cause a silent mutation, but rather a conversion of an amino acid encoded by the codon comprising the position to be converted with the base editor.

As used herein, a "regulatory element" refers to nucleotide sequences which are not part of the protein-encoding nucleotide sequence, but mediate the expression of the protein-encoding nucleotide sequence. Regulatory elements include, for example, promoters, cis-regulatory elements, enhancers, introns or terminators. Depending on the type of regulatory element it is located on the nucleic acid molecule before (i.e., 5' of) or after (i.e., 3' of) the protein-encoding nucleotide sequence. Regulatory elements are functional in a living plant cell. The term "operatively linked" means that a regulatory element is linked in such a way with the protein-encoding nucleotide sequence, i.e., is positioned in such a way relative to the protein-encoding nucleotide sequence on, for example, a nucleic acid molecule that an expression of the protein-encoding nucleotide sequence under the control of the regulatory element can take place in a living cell.

As used herein, "upstream" indicates a location on a nucleic acid molecule which is nearer to the 5' end of said nucleic acid molecule. Likewise, the term "downstream" refers to a location on a nucleic acid molecule which is nearer to the 3' end of said nucleic acid molecule. For avoidance of doubt, nucleic acid molecules and their sequences are typically represented in their 5' to 3' direction (left to right).

As used herein, a "flanking region" is a region of the repair nucleic acid molecule having a nucleotide sequence which is homologous to the nucleotide sequence of the DNA region flanking (i.e. upstream or downstream) of the preselected site.

As used herein, "transient expression" refers to the phenomenon where the transferred protein/polypeptide and nucleic acid fragment encoding the protein/polypeptide is expressed and/or active transiently in the cells, and turned off and/or degraded shortly with the cell growth.

As used herein, a "double-stranded DNA break inducing enzyme", "enzyme inducing a double-stranded break", or "DSBI enzyme" is an enzyme capable of inducing a double-stranded DNA break at a particular nucleotide sequence, called the "recognition site" or "predetermined site". Accordingly, a "single-stranded DNA or RNA break inducing enzyme", "enzyme inducing a single-stranded break", or "SSBI enzyme" is an enzyme capable of inducing a single-stranded DNA or RNA break at a particular nucleotide sequence, called the "recognition site" or "predetermined site".

As used herein, a "repair nucleic acid molecule" is a single-stranded or double-stranded DNA molecule or RNA molecule that is used as a template for modification of the genomic DNA or the RNA at the preselected site in the vicinity of or at the cleavage site. As used herein, "use as a template for modification of the genomic DNA", means that the repair nucleic acid molecule is copied or integrated at the preselected site by homologous recombination between the flanking region(s) and the corresponding homology region (s) in the target genome flanking the preselected site, optionally in combination with non-homologous end-joining (NHEJ) at one of the two end of the repair nucleic acid molecule (e.g., in case there is only one flanking region).

As used herein, "a modification of the genome", means that the genome has changed in at least one nucleotide or by at least one epigenetic editing.

As used herein "a preselected site", "a predetermined site" or "predefined site" indicates a particular nucleotide sequence in the genome (e.g., the nuclear genome or the chloroplast genome) at which location it is desired to insert, replace and/or delete one or more nucleotides.

As used herein, "phytohormone" or "plant growth regulator" refers to any material and chemical, either naturally occurred or synthesized, which promotes plant cell division and/or plant morphogenesis. As used herein, "regeneration" refers to a process in which single or multiple cells proliferate and develop into tissues, organs, and eventually entire plants.

As used herein, the terms "vector", or "plasmid (vector)" refers to a construct comprising, inter alia, plasmids or (plasmid) vectors, cosmids, artificial yeast- or bacterial artificial chromosomes (YACs and BACs), phagemides, bacterial phage based vectors, an expression cassette, isolated single-stranded or double-stranded nucleic acid sequences, comprising sequences in linear or circular form, or amino acid sequences, viral vectors, including modified viruses, and a combination or a mixture thereof, for introduction or transformation, transfection or transduction into any eukaryotic cell, including a plant, plant cell, tissue, organ or material according to the present disclosure.

"Recombinant" in the context of the recombinant gene can comprise regulatory sequences and/or localization sequences. The recombinant construct or the DNA construct according to the present invention can be integrated into or can be a vector, including a plasmid vector, and/or it can be present isolated from a vector structure, for example, in the form of a single-stranded or double-stranded nucleic acid. After its introduction, e.g., by transformation or transfection by biological or physical means, the recombinant gene or the DNA construct can either persist extrachromosomally, i.e. non-integrated into the genome of the target cell, for example in the form of a double-stranded or single-stranded DNA. Alternatively, the recombinant gene or the DNA construct, can be stably integrated into the genome of a target cell, including the nuclear genome or further genetic elements of a target cell, including the genome of plastids like mitochondria or chloroplasts.

The inventors show that a nucleic acid encoding RKD2 and/or RKD4 mediates a strong effect in particular in the early phase of regeneration after delivery of transgene and/or the genome engineering component. This effect does not compromise plant development and regenerated plants show favorable plant growth in the adult stage and are fertile. As such, integration of RKD2 and RKD4 genes can be segregated out in the following generation by crossing and selection.

RKD2 and RKD4 are plant-specific RWP-RK transcription factors. RKD2 and RKD4 are found in *Arabidopsis* and other plant species, such as *Triticum aestivum* and *Zea mays*. RKD2 and RKD4 alone, or in combination, can bring about improved genome engineering and/or improved plant regeneration of transformed or gene edited plant cells. RKD2 and RKD4 alone, or together, may increase the capability or ability of a plant cell, preferably derived from somatic tissue, embryonic tissue, callus tissue or protoplast, to regenerate in an entire plant, preferably a fertile plant. Thereby, RKD2 and RKD4 each, or together, may regulate somatic embryo formation (somatic embryogenesis) and/or may increase the proliferation rate of plant cells. The combination of RKD2 and RKD4 together may be synergistic. In the various methods disclosed herein, RKD2, RKD4, or a combination of RKD2 and RKD4, can be transiently co-expressed. A polynucleotide encoding for RKD2 or RKD4 may be introduced into the plant cell.

Also provided is a nucleic acid encoding RKD2 or RKD4 comprising an amino acid sequence of SEQ ID NO: 2 or 5. Further provided is a nucleic acid encoding RKD2 or RKD4 comprising an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 5.

The nucleic acid encoding RKD4 comprising an amino acid sequence of SEQ ID NO: 2 or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2, can comprise a nucleic acid comprising the nucleotide sequence of SEQ ID NO: 1. The nucleic acid can comprise a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1. Alternatively, the nucleic acid can hybridize, under stringent hybridization conditions, with the complementary strand of a nucleic acid comprising the nucleotide sequence of SEQ ID NO: 1 or a nucleic acid comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1.

The nucleic acid encoding RKD2 comprising an amino acid sequence of SEQ ID NO: 5 or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 5, can also comprise a nucleic acid comprising the nucleotide sequence of SEQ ID NO: 3 or 4. The nucleic acid can comprise a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 3. The nucleic acid can comprise a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 4. Alternatively, the nucleic acid can hybridize, under stringent hybridization conditions, with the complementary strand of a nucleic acid comprising the nucleotide sequence of SEQ ID NO: 3 or a nucleic acid comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 3. Alternatively, the nucleic acid can hybridize, under stringent hybridization conditions, with the complementary strand of a nucleic acid comprising the nucleotide sequence of SEQ ID NO: 4 or a nucleic acid comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 4.

A recombinant gene comprising a nucleic acid encoding RKD2 or RKD4 comprising an amino acid sequence of SEQ ID NO: 2 or 5, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 5 is provided. The nucleic acid can be operatively linked to one or more regulatory elements. The regulatory element can be a promoter, a cis-regulatory element, an enhancer, an intron or a terminator. The regulatory element can be 5' to the nucleic acid sequence. The regulatory element can be 3' to the nucleic acid sequence. The regulatory element can be a directional promoter. The nucleic acid can comprise a nucleic acid comprising the nucleotide sequence of SEQ ID NO: 1, 3 or 4. The nucleic acid can comprise a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1, 3 or 4. The nucleic acid can hybridize, under stringent hybridization conditions, with the complementary strand of a nucleic acid comprising the nucleotide sequence of SEQ ID NO: 1, 3 or 4 or a nucleic acid comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1, 3 or 4.

In some embodiments, the nucleic acid is operably linked to a heterologous promoter. The heterologous promoter can be an inducible promoter.

The heterologous promoter can be a bidirectional inducible promoter, e.g., pOp6, a chemically-inducible promoter. The pOp6 promoter comprises six copies of an optimized lac operator sequence, such as described in Samalova et al., Plant J., 2005, 41(6):919-35. As part of the pOp6/LhGR expression system, dexamethasone mobilizes localization of LhGR to the nucleus where LhGR activates pOp6. LhGR may be operatively linked to a strong constitutive promoter (e.g., a ubiquitin promoter or a double 35S promoter). The LhGR encoding sequence may further comprise a ubiquitin intron. As an alternative, LhGR and the strong constitutive promoter may be expressed on a separate DNA construct.

In some embodiments, in step (a) (i) a further a nucleic acid comprising a polynucleotide sequence encoding a transcription factor operably linked to a strong constitutive promoter is introduced into the plant cell, wherein the transcription factor activates pOp6 upon binding to dexamethasone. In specific embodiments, the transcription factor is LhGR or LhG4. In some embodiments, the LhGR has the amino acid sequence of SEQ ID NO: 17, or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 17; or wherein the nucleic acid encoding LhGR comprises the coding sequence of SEQ ID NO: 16, or a coding sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 16.

In some embodiments, the strong constitutive promoter is a ubiquitin promoter or a double 35S promoter. In some specific embodiments, the double 35S promoter comprises the nucleotide sequence of SEQ ID NO: 21, or a nucleotide sequence at least 90%, 91%, 92%, 93%, 94%, 95%, 96%, 97%, 98%, 99% identical to SEQ ID NO: 21. In some specific embodiments, the ubiquitin promoter comprises the nucleotide sequence of SEQ ID NO: 23, or a nucleotide sequence at least 90%, 91%, 92%, 93%, 94%, 95%, 96%, 97%, 98%, 99% identical to SEQ ID NO: 23. In some specific embodiments, the ubiquitin promoter comprises additionally a ubiquitin intron comprising the nucleotide sequence of SEQ ID NO: 20, or a nucleotide sequence at least 90%, 91%, 92%, 93%, 94%, 95%, 96%, 97%, 98%, 99% identical to SEQ ID NO: 20.

The activated pOp6 is capable of directing transcription of genes operatively linked to pOp6. Due to the bidirectional nature, pOp6 can express both a gene of interest (e.g., a developmental gene) and a reporter gene (e.g., GUS or tdTomato). As an alternative, pOp1, pOp2, or pOp4 may also be used.

Alternatively, the heterologous promoter can be XVE/OlexA, e.g., as part of the XVE/OlexA system that is β-estradiol inducible. Upon exposure to β-estradiol, XVE/OlexA is activated and capable of directing transcription of genes operatively linked to XVE/OlexA.

The GUS reporter system is suitable for most plants due to the low level of β-glucuronidase activity found in the plants. (GUS is a β-glucuronidase.) The tDTomato gene (tDT) encodes an exceptionally bright red fluorescent protein with excitation maximum at 554 nm and emission maximum at 581 nm. Alternatively, other reporters can be used such as luciferase, beta-galactosidase, chloramphenicol acetyltransferase (CAT), and alkaline phosphatase.

Also provided is a DNA construct, preferably a vector, comprising any of the above nucleic acids or recombinant genes. The nucleic acid can comprise a nucleic acid comprising the nucleotide sequence of SEQ ID NO: 1, 3 or 4. The nucleic acid can comprise a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1, 3 or 4. Alternatively, the nucleic acid can hybridize, under stringent hybridization conditions, with the complementary strand of a nucleic acid comprising the nucleotide sequence of SEQ ID NO: 1, 3 or 4 or a nucleic acid comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1, 3 or 4. In some embodiments, the DNA construct is a plasmid. In some embodiments, the DNA construct comprises a bidirectional inducible promoter (e.g., pOp6). The nucleic acid can be operably linked to the bidirectional inducible promoter. In some embodiments, the DNA construct comprises the XVE/OlexA promoter system capable of inducing expression of the nucleic acid upon exposure to β-estradiol. Another reporter nucleic acid (e.g., GUS or tdTomato) can also be operably linked to the bidirectional inducible promoter. The reporter nucleic acid may assist in selecting against plants that express the nucleic acid in a leaky manner, such as when no induction of the bidirectional inducible promoter occurs. For example, plants may be selected against that express GUS or tdTomato, which is operably linked to dexamethasone-inducible pOp6 when no dexamethasone is applied.

Plant Cells

In another aspect is provided a plant cell comprising one or more of RKD2 or RKD4, nucleic acids, recombinant genes and DNA constructs described herein, preferably as transgene(s). In some embodiments, RKD2 or RKD4 comprises the amino acid sequence of SEQ ID NO: 2 or 5. In some embodiments, the RKD2 or RKD4 comprises the amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 5. The nucleic acid can comprise a nucleic acid comprising the nucleotide sequence of SEQ ID NO: 1, 3 or 4. The nucleic acid can comprise a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1, 3 or 4. The nucleic acid can hybridize, under stringent hybridization conditions, with the complementary strand of a nucleic acid comprising the nucleotide sequence of SEQ ID NO: 1, 3 or 4 or a nucleic acid comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1, 3 or 4. Also provided is a plant, a part of the plant, a seed, an embryo or callus comprising the plant cell.

Plant cells can be part of or derived from any type of plant material, preferably shoot, hypocotyl, cotyledon, stem, leave, petiole, root, embryo, callus, flower, gametophyte or part thereof or can be a protoplast or derived from a protoplast. It is possible to use isolated plant cells as well as plant material, i.e. whole plants or parts of plants containing the plant cells.

A part of a plant, or parts of plants, may be attached to or separated from a whole intact plant. Such parts of a plant include, but are not limited to, organs, tissues, and cells of a plant, and preferably seeds.

The plant cell, plant part or plant can be from any plant species, whether monocot or dicot. Preferably, plants which may be subject to the methods and uses of the present invention are plants of the genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium,* or *Helianthus*. More preferably, the plant is selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max,* and/or *Gossypium* sp.

Genetically modified plant cells can be part of a whole plant or part thereof. Thus, the present invention also relates to a plant or plant part comprising the above genetically modified plant cell.

The plant cells into which the genome engineering components have been (co-)introduced are cultured under conditions allowing the genetic modification of the genome of said plant cell by integration of the transgene of interest and activity of the genome engineering components in the presence of RKD2 or RKD4.

Genetic Modification of a Plant Cell

Also provided is a method for genetic modification in a plant cell. The method comprises introducing into the plant cell (i) any of the nucleic acids, recombinant genes or DNA constructs described herein; and (ii) a transgene and/or a genome engineering component. The plant cell may be cultivated under conditions allowing the synthesis of the RKD2 or RKD4 polypeptide from the nucleic acid, the recombinant gene or the DNA construct. The plant cell may be cultivated under conditions allowing the genetic modification of the genome of said plant cell by activity of the genome engineering component in the presence of the RKD2 or RKD4 polypeptide.

The genome engineering component can be introduced as a protein and/or as a nucleic acid encoding the genome engineering component, in particular as DNA such as plasmid DNA, RNA, mRNA or RNP. Genome engineering can be used for the manufacture of transgenic, gene-edited or base-edited plant material.

For plant cells to be modified, transformation methods based on biological approaches may be used, such as *Agrobacterium* transformation or viral vector-mediated plant transformation. A common biological means is transformation with *Agrobacterium* spp. which has been used for decades for a variety of different plant materials. Viral vector mediated plant transformation also can be used to introduce genetic material into a cell of interest. *Agrobacterium*-mediated transformation refers to the method of using *Agrobacterium tumefaciens*, a soil bacterium that works as a natural genetic engineer vector, to deliver foreign DNA into plant cells. *Agrobacterium tumefaciens* can invade plants and transfer foreign DNA in remarkably broad range of plants.

Alternatively, transformation methods based on physical delivery methods may be used, like particle bombardment or microinjection. Particle bombardment includes biolistic transfection or microparticle-mediated gene transfer, which refers to a physical delivery method for transferring a coated microparticle or nanoparticle comprising a nucleic acid or a genetic construct of interest into a target cell or tissue. Physical introduction means are suitable to introduce nucleic acids, i.e., RNA and/or DNA, and proteins. Particle bombardment and microinjection have evolved as prominent techniques for introducing genetic material into a plant cell or tissue of interest. Helenius et al., "Gene delivery into intact plants using the Helios™ Gene Gun", Plant Molecular Biology Reporter, 2000, 18(3):287-288 discloses a particle bombardment as physical method for introducing material into a plant cell. Thus, there exists a variety of plant transformation methods to introduce genetic material in the form of a genetic construct into a plant cell of interest, comprising biological and physical means known to the skilled person on the field of plant biotechnology and which can be applied to introduce at least one gene encoding at least one wall-associated kinase into at least one cell of at least one of a plant cell, tissue, organ, or whole plant.

The term "particle bombardment" as used herein, also named "biolistic transfection" or "microparticle-mediated gene transfer" refers to a physical delivery method for transferring a coated microparticle or nanoparticle comprising RKD2 or RKD4 genes, genome engineering components, and/or transgenes into a target cell or tissue. The micro- or nanoparticle functions as projectile and is fired on the target structure of interest under high pressure using a suitable device, often called gene-gun. The transformation via particle bombardment uses a microprojectile of metal covered with the construct of interest, which is then shot onto the target cells using an equipment known as "gene gun" (Sandford et al. 1987) at high velocity fast enough (~1500 km/h) to penetrate the cell wall of a target tissue, but not harsh enough to cause cell death. For protoplasts, which have their cell wall entirely removed, the conditions are different logically. The precipitated construct on the at least one microprojectile is released into the cell after bombardment. The acceleration of microprojectiles is accomplished by a high voltage electrical discharge or compressed gas (helium). Concerning the metal particles used it is mandatory that they are non-toxic, non-reactive, and that they have a lower diameter than the target cell. The most commonly used are gold or tungsten. There is plenty of information publicly available from the manufacturers and providers of gene-guns and associated system concerning their general use.

In a particularly preferred embodiment of microparticle bombardment, one or more RKD2 or RKD4 genes, genome engineering components, and/or transgenes are co-delivered via microcarriers comprising gold particles having a size in a range of 0.4-1.6 micron ($\mu$m), preferably 0.4-1.0 $\mu$m. In an exemplary process, 10-1000 $\mu$g of gold particles, preferably 50-300 $\mu$g, are used per one bombardment.

The RKD2 or RKD4 genes, genome engineering components, and/or transgenes can be delivered into target cells for example using a Bio-Rad PDS-1000/He particle gun or handheld Helios gene gun system. When a PDS-1000/He particle gun system used, the bombardment rupture pressures are from 450 psi to 2200 psi, preferred from 450-1100 psi, while the rupture pressures are from 100-600 psi for a Helios gene gun system. More than one chemical or construct can be co-delivered with genome engineering components into target cells simultaneously.

The above-described delivery methods for transformation and transfection can be applied to introduce the tools of the present invention simultaneously. Likewise, specific transformation or transfection methods exist for specifically introducing a nucleic acid or an amino acid construct of interest into a plant cell, including electroporation, microinjection, nanoparticles, and cell-penetrating peptides (CPPs). Furthermore, chemical-based transfection methods exist to introduce genetic constructs and/or nucleic acids and/or proteins, comprising inter alia transfection with calcium phosphate, transfection using liposomes, e.g., cationic liposomes, or transfection with cationic polymers, including DEAD-dextran or polyethylenimine, or combinations thereof. The above delivery techniques, alone or in combination, can be used for in vivo (including in planta) or in vitro approaches.

In some embodiments, the genome engineering component comprises:

a) an enzyme inducing a double-stranded break (DSB) or a nucleic acid encoding same, and optionally a repair nucleic acid molecule, wherein the DSB-inducing enzyme optionally recognizes a predetermined site in the genome of said cell;

b) an enzyme inducing a single-stranded break (SSB) or a nucleic acid encoding same, and optionally a repair nucleic acid molecule, wherein the SSB-inducing enzyme optionally recognizes a predetermined site in the genome of said cell;

c) a base editor enzyme, optionally fused to a disarmed DSB- or SSB-inducing enzyme, wherein the base editor enzyme preferably recognizes a predetermined site in the genome of said cell; or d) an enzyme effecting DNA methylation, histone acetylation, histone methylation, histone ubiquitination, histone phosphorylation, histone ribosylation or histone citrullination, optionally fused to a disarmed DSB- or SSB-inducing enzyme, wherein the enzyme preferably recognizes a predetermined site in the genome of said cell.

In order to enable a break at a predetermined target site, the enzymes preferably include a binding/recognition domain and a cleavage domain. Particular enzymes capable of inducing double or single-stranded breaks are nucleases or nickases as well as variants thereof, including such molecules no longer comprising a nuclease or nickase function but rather operating as recognition molecules in combination with another enzyme. In recent years, many suitable nucleases, especially tailored endonucleases have been developed comprising meganucleases, zinc finger nucleases, TALE nucleases, Argonaute nucleases, derived, for example, from *Natronobacterium gregoryi*, and CRISPR nucleases, comprising, for example, Cas9, Cpf1, Csm1, MAD7, CasX or CasY nucleases as part of the Clustered Regularly Interspaced Short Palindromic Repeats (CRISPR) system. Thus, in a preferred aspect of the invention, the genome engineering component comprises a DSB- or SSB-inducing enzyme or a variant thereof selected from a CRISPR/Cas endonuclease, a CRISPR/Cas9 endonuclease, a CRISPR/Cpf1 endonuclease, a CRISPR/Csm1 endonuclease, a CRISPR/MAD7 endonuclease, a CRISPR/CasX endonuclease, a CRISPR/CasY endonuclease, a zinc finger nuclease (ZFN), a homing endonuclease, a meganuclease and a TAL effector nuclease.

Rare-cleaving endonucleases are DSBI/SSBI enzymes that have a recognition site of preferably about 14 to 70 consecutive nucleotides, and therefore have a very low frequency of cleaving, even in larger genomes such as most plant genomes. Homing endonucleases, also called meganucleases, constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level. A list of other rare cleaving meganucleases and their respective recognition sites is provided in Table I of WO 03/004659 (pages 17 to 20) (incorporated herein by reference).

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described, e.g., in WO 03/080809, WO 94/18313 or WO 95/09233 and in Isalan et al. (2001). A rapid, generally applicable method to engineer zinc fingers illustrated by targeting the HIV-1 promoter. Nature biotechnology, 19(7): 656; Liu et al. (1997). Design of polydactyl zinc-finger proteins for unique addressing within complex genomes. Proceedings of the National Academy of Sciences, 94(11): 5525-5530.

Another example of custom-designed endonucleases includes the TALE nucleases (TALENs), which are based on transcription activator-like effectors (TALEs) from the bacterial genus *Xanthomonas* fused to the catalytic domain of a nuclease (e.g., FokI or a variant thereof). The DNA binding specificity of these TALEs is defined by repeat-variable di-residues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see, e.g., Boch et al. (2009). Breaking the code of DNA binding specificity of TAL-type III effectors. *Science,* 326(5959), 1509-1512; Moscou & Bogdanove (2009). A simple cipher governs DNA recognition by TAL effectors. *Science,* 326(5959), 1501-1501; and WO 2010/079430, WO 2011/072246, WO 2011/154393, WO 2011/146121, WO 2012/001527, WO 2012/093833, WO 2012/104729, WO 2012/138927, WO 2012/138939). WO 2012/138927 further describes monomeric (compact) TALENs and TALEs with various catalytic domains and combinations thereof.

Recently, a new type of customizable endonuclease system has been described; the so-called CRISPR/Cas system. A CRISPR system in its natural environment describes a molecular complex comprising at least one small and individual non-coding RNA in combination with a Cas nuclease or another CRISPR nuclease like a Cpf1 nuclease or a Csm1 nuclease (Zetsche et al., "Cpf1 Is a Single RNA-Guides Endonuclease of a Class 2 CRISPR-Cas System", Cell, 163, pp. 1-13, October 2015.; US 2017/0233756 A1) which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems code for a Cas9 nuclease as the key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease.

As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognizes and cleaves target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

The cleavage site of a DSBI/SSBI enzyme relates to the exact location on the DNA or RNA where the break is induced. The cleavage site may or may not be comprised in (overlap with) the recognition site of the DSBI/SSBI enzyme and hence it is said that the cleavage site of a DSBI/SSBI enzyme is located at or near its recognition site. The recognition site of a DSBI/SSBI enzyme, also sometimes referred to as binding site, is the nucleotide sequence that is (specifically) recognized by the DSBI/SSBI enzyme and determines its binding specificity. For example, a TALEN or ZNF monomer has a recognition site that is determined by their RVD repeats or ZF repeats respectively, whereas its cleavage site is determined by its nuclease domain (e.g., FokI) and is usually located outside the recognition site. In case of dimeric TALENs or ZFNs, the cleavage site is located between the two recognition/binding sites of the respective monomers, this intervening DNA or RNA region where cleavage occurs being referred to as the spacer region.

A person skilled in the art would be able to choose a DSBI/SSBI enzyme recognizing a certain recognition site and inducing a DSB or SSB at a cleavage site at or in the vicinity of the preselected/predetermined site or engineer such a DSBI/SSBI enzyme. Alternatively, a DSBI/SSBI enzyme recognition site may be introduced into the target genome using any conventional transformation method or by crossing with an organism having a DSBI/SSBI enzyme recognition site in its genome, and any desired nucleic acid may afterwards be introduced at or in the vicinity of the cleavage site of that DSBI/SSBI enzyme.

In various embodiments, modification of the genome comprises one or more of: i) a replacement of at least one nucleotide; ii) a deletion of at least one nucleotide; iii) an insertion of at least one nucleotide; iv) a change of the DNA methylation; and v) a change in histone acetylation, histone methylation, histone ubiquitination, histone phosphorylation, histone sumoylation, histone ribosylation or histone citrullination.

In some embodiments, the activity of the genome engineering component induces one or more double-stranded breaks in the genome of the plant cell, one or more single strand breaks in the genome of the plant cell, one or more base editing events in the genome of the plant cell, or one or more of DNA methylation, histone acetylation, histone methylation, histone ubiquitination, histone phosphorylation, histone sumoylation, histone ribosylation or histone citrullination in the genome of the plant cell.

In some embodiments, the induction of one or more double-stranded breaks or one or more single strand breaks is followed by non-homologous end joining (NHEJ) and/or by homology directed repair of the break(s) though a homologous recombination mechanism (HDR). NHEJ and HDR are two major and distinct pathways to repair breaks. Homologous recombination requires the presence of a homologous sequence as a template (e.g., repair nucleic acid molecule or "donor") to guide the cellular repair process and the results of the repair are error-free and predictable. In the absence of a template (or repair nucleic acid molecule or "donor") sequence for homologous recombination, the cell typically attempts to repair the break via the process of non-homologous end-joining (NHEJ).

In a particularly preferred aspect of this embodiment, a repair nucleic acid molecule is additionally introduced into the plant cell. The repair nucleic acid molecule is a single-stranded or double-stranded DNA molecule or RNA molecule that is used as a template for modification of the genomic DNA or the RNA at the preselected site in the vicinity of or at the cleavage site. In some embodiments, the repair nucleic acid molecule is used as a template for modification of the genomic DNA, in which the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two end of the repair nucleic acid molecule (e.g., in case there is only one flanking region). Integration by homologous recombination allows for precise joining of the repair nucleic acid molecule to the target genome up to the nucleotide level, while NHEJ may result in small insertions/deletions at the junction between the repair nucleic acid molecule and genomic DNA.

In various embodiments of the aspects described herein, a modification of the genome occurs in which the genome has changed by at least one nucleotide. Modification of the genome can occur by insertion of a transgene, preferably an expression cassette comprising a transgene of interest, replacement of at least one nucleotide and/or a deletion of at least one nucleotide and/or an insertion of at least one nucleotide, as long as it results in a total change of at least one nucleotide compared to the nucleotide sequence of the preselected genomic target site before modification, thereby allowing the identification of the modification, e.g., by techniques such as sequencing or PCR analysis and the like, of which the skilled person will be well aware.

Modification of the genome may occur at a preselected site, a predetermined site, or predefined site, i.e., at a particular nucleotide sequence in the genome (e.g., the nuclear genome or the chloroplast genome) at which location it is desired to insert, replace and/or delete one or more nucleotides. For example, the preselected site, predetermined site, or predefined site can be an endogenous locus or a particular nucleotide sequence in or linked to a previously introduced foreign DNA, RNA or transgene. The preselected site can be a particular nucleotide position at (after) which it is intended to make an insertion of one or more nucleotides. The preselected site can also comprise a sequence of one or more nucleotides which are to be exchanged (replaced) or deleted.

In various embodiments, the length and percentage sequence identity of the flanking regions is chosen such as to enable homologous recombination between said flanking regions and their corresponding DNA region upstream or downstream of the preselected site. The DNA region or regions flanking the preselected site having homology to the flanking DNA region or regions of the repair nucleic acid molecule are also referred to as the homology region or regions in the genomic DNA.

To have sufficient homology for recombination, the flanking DNA regions of the repair nucleic acid molecule may vary in length, and should be at least about 10 nt, about 15 nt, about 20 nt, about 25 nt, about 30 nt, about 40 nt or about 50 nt in length. However, the flanking region may be as long as is practically possible (e.g., up to about 100-150 kb such as complete bacterial artificial chromosomes (BACs). Preferably, the flanking region will be about 50 nt to about 2000 nt, e.g., about 100 nt, 200 nt, 500 nt or 1000 nt. Moreover, the regions flanking the DNA of interest need not be identical to the homology regions (the DNA regions flanking the preselected site) and may have between about 80% to about 100% sequence identity, preferably about 95% to about 100% sequence identity with the DNA regions flanking the preselected site. The longer the flanking region, the less stringent the requirement for homology. Furthermore, to achieve exchange of the target DNA sequence at the preselected site without changing the DNA sequence of the adjacent DNA sequences, the flanking DNA sequences should preferably be identical to the upstream and downstream DNA regions flanking the preselected site.

In order to target sequence modification at the preselected site, the flanking regions must be chosen so that 3' end of the upstream flanking region and/or the 5' end of the downstream flanking region align(s) with the ends of the predefined site. As such, the 3' end of the upstream flanking region determines the 5' end of the predefined site, while the 5' end of the downstream flanking region determines the 3' end of the predefined site.

The preselected site is located outside or away from said cleavage (and/or recognition) site, such that the site where it is intended to make the genomic modification (the preselected site) does not comprise the cleavage site and/or recognition site of the DSBI/SSBI enzyme, such that the preselected site does not overlap with the cleavage (and/or recognition) site. Outside/away from in this respect thus means upstream or downstream of the cleavage (and/or recognition) site.

In various embodiments, the at least one base editor according to the present invention is temporarily or permanently linked to at least one site-specific DSBI/SSBI enzyme complex or at least one modified site-specific DSBI/SSBI enzyme complex, or optionally to a component of said at least one site-specific DSBI/SSBI enzyme complex. The linkage can be covalent and/or non-covalent. Any base editor or site-specific DSBI/SSBI enzyme complex, or a catalytically active fragment thereof, or any component of a base editor complex or of a site-specific DSBI/SSBI enzyme complex as disclosed herein can be introduced into a cell as a nucleic acid fragment, the nucleic acid fragment representing or encoding a DNA, RNA or protein effector, or it can be introduced as DNA, RNA and/or protein, or any combination thereof.

The base editor is a protein or a fragment thereof having the capacity to mediate a targeted base modification, i.e., the conversion of a base of interest resulting in a point mutation of interest. Preferably, the at least one base editor in the context of the present invention is temporarily or permanently fused to at least one DSBI/SSBI enzyme, or optionally to a component of at least one DSBI/SSBI. The fusion can be covalent and/or non-covalent. Multiple publications have shown targeted base conversion, primarily cytidine (C) to thymine (T), using a CRISPR/Cas9 nickase or non-functional nuclease linked to a cytidine deaminase domain, Apolipoprotein B mRNA-editing catalytic polypeptide (APOBEC1), e.g., APOBEC derived from rat. The deamination of cytosine (C) is catalyzed by cytidine deaminases and results in uracil (U), which has the base-pairing properties of thymine (T). Most known cytidine deaminases operate on RNA, and the few examples that are known to accept DNA require single-stranded (ss) DNA. Studies on the dCas9-target DNA complex reveal that at least nine nucleotides (nt) of the displaced DNA strand are unpaired upon formation of the Cas9-guide RNA-DNA 'R-loop' complex (Jore et al., Nat. Struct. Mol. Biol., 18, 529-536 (2011)). Indeed, in the structure of the Cas9 R-loop complex, the first 11 nt of the protospacer on the displaced DNA strand are disordered, suggesting that their movement is not highly restricted. It has also been speculated that Cas9 nickase-induced mutations at cytosines in the non-template strand might arise from their accessibility by cellular cytosine deaminase enzymes. It was reasoned that a subset of this stretch of ssDNA in the R-loop might serve as an efficient substrate for a dCas9-tethered cytidine deaminase to effect direct, programmable conversion of C to U in DNA (Komor et al., supra). Recently, Goudelli et al., Programmable base editing of A• T to G• C in genomic DNA without DNA cleavage, Nature, 2017, 551(7681), 464, described adenine base editors (ABEs) that mediate the conversion of A•T to G•C in genomic DNA.

Enzymes effecting DNA methylation, as well as histone-modifying enzymes have been identified in the art. Histone posttranslational modifications play significant roles in regulating chromatin structure and gene expression. For example, enzymes for histone acetylation are described in Sterner D. E., Berger S. L. (June 2000): "Acetylation of histones and transcription-related factors", Microbiol. Mol. Biol. Rev. 64 (2): 435-59. Enzymes effecting histone methylation are described in Zhang Y., Reinberg D (2001): "Transcription regulation by histone methylation: interplay between different covalent modifications of the core histone tails", Genes Dev. 15 (18): 2343-60. Histone ubiquitination is described in Shilatifard A (2006): "Chromatin modifications by methylation and ubiquitination: implications in the regulation of gene expression", Annu. Rev. Biochem. 75: 243-69. Enzymes for histone phosphorylation are described in Nowak S. J., Corces V. G. (April 2004): "Phosphorylation of histone H3: a balancing act between chromosome condensation and transcriptional activation", Trends Genet. 20 (4): 214-20. Enzymes for histone sumoylation are described in Nathan D., Ingvarsdottir K., Sterner D. E., et al. (April 2006): "Histone sumoylation is a negative regulator in *Saccharomyces cerevisiae* and shows dynamic interplay with positive-acting histone modifications", Genes Dev. 20 (8): 966-76. Enzymes for histone ribosylation are described in Hassa P. O., Haenni S. S., Elser M., Hottiger M. O. (September 2006): "Nuclear ADP-ribosylation reactions in mammalian cells: where are we today and where are we going?", Microbiol. Mol. Biol. Rev. 70 (3): 789-829. Histone citrullination is catalyzed for example by an enzyme called peptidylarginine deiminase 4 (PAD4, also called PAD14), which converts both histone arginine (Arg) and mono-methyl arginine residues to citrulline.

Enzymes effecting DNA methylation and histone-modifying enzymes may be fused to a disarmed DSB or SSB inducing enzyme, which preferably recognizes a predetermined site in the genome of said cell.

Exemplary Transgenes

In various embodiments of the methods for genetic modification in a plant cell, the transgene may be a gene encoding resistance or tolerance to abiotic stress, including drought stress, osmotic stress, heat stress, cold stress, oxidative stress, heavy metal stress, nitrogen deficiency, phosphate deficiency, salt stress or waterlogging, herbicide resistance, including resistance to glyphosate, glufosinate/phosphino-tricin, hygromycin, protoporphyrinogen oxidase (PPO) inhibitors, ALS inhibitors, and Dicamba, a gene encoding resistance or tolerance to biotic stress, including a viral resistance gene, a fungal resistance gene, a bacterial resistance gene, an insect resistance gene, or a gene encoding a yield related trait, including lodging resistance, flowering time, shattering resistance, seed color, endosperm composition, or nutritional content.

In various embodiments of the methods for genetic modification in a plant cell, the method is effective to promote cell proliferation or cell regeneration, or is effective to increase the efficiency for regeneration of transgenic, gene edited or base edited plants. The method is effective preferably after genetic modification/modification of the genome. In various embodiments of the methods for genetic modification in a plant cell, the method is effective to induce direct or indirect (somatic) embryogenesis from a single cell, preferably an embryonic cell, a somatic cell or a protoplast, or from a callus cell, or from a callus cell. The method is effective preferably after genetic modification/modification of the genome. In various embodiments, the method is effective to increase the stable transformation efficiency of the transgene into the plant cell or is effective to increase the efficiency for generation of transgenic plants. In various embodiments, the method is effective to increase the efficiency of the genome engineering component to edit the genome of the plant cell or is effective to increase the efficiency for generation of transgenic, gene edited or base edited plants.

In some embodiments, the method is effective to improve the efficiency of regeneration of plants derived from recalcitrant genotypes, is effective to improve the efficiency of regeneration of plants from non-conventional tissue types, or is effective to accelerate the regeneration process, preferably after genetic modification/modification of the genome.

Transient Expression of RKD2 or RKD4 Genes

Also provided is a method for transient expression of an RKD2 or RKD4 gene in a plant cell. The method comprises introducing into the plant cell (i) a nucleic acid, recombinant gene or DNA construct described herein; and (ii) a transgene and/or a genome engineering component.

In some embodiments, RKD2 and RKD4 are transiently co-expressed. The co-expression may be effective to promote cell proliferation. Such co-expression may be effective to promote cell regeneration. The co-expression may be effective to induce embryogenesis from single cells, and thus provide ability to regenerate homogenous plants without selection. The co-expression may improve genome editing efficiency by co-delivery with genome-editing components.

Transient co-delivery of RKD2 and RKD4 may be carried out as described in U.S. Provisional Application No. 62/685,626, incorporated by reference herein in its entirety.

Transient expression can be carried out by transient transformation/transfection of a nucleic acid fragment encoding the RKD2 or RKD4 protein/polypeptide, expressed preferably under a chemically inducible promoter. Transient expression of a nucleic acid encoding an RKD2 polypeptide or a nucleic acid encoding an RKD4 polypeptide can also be realized by stable transformation of an RKD2 or RKD4 gene under the control of a tissue and development specific promoter or an inducible promoter. The RKD2 or RKD4 genes can be expressed and then be active transiently. The RKD2 or RKD4 genes can then be turned off and degraded shortly when plant cell development is changed or the inducing condition(s) are removed. For example, the dexamethasone-inducible promoter pOp6 (SEQ ID NO: 15) may be used to drive an RKD2 or RKD4 gene for transient transformation.

Transient expression can arise from any of transient transfection, transient transformation, and stable transformation. "Transient transformation" and "transient transfection" comprise the transfer of a foreign material [i.e. a nucleic acid fragment, protein, ribonucleoprotein (RNP), etc.] into host cells resulting in gene expression and/or activity without integration and stable inheritance of the foreign material. The foreign components are not permanently incorporated into the cellular genome, but provide a temporal action resulting in a modification of the genome. A transient transformation event may be unable to be transmitted to next generation, and thus is non-inheritable. "Stable transformation" refers to the event where a transferred nucleic acid fragment is integrated into the genome of a host cell (includes both nuclear and organelle genomes) resulting to stable inheritance of the nucleic acid fragment.

For example, transient expression can be used for transient genome editing. Transient activity and/or transient presence of the genome engineering component in the plant cell can result in introduction of one or more double-stranded breaks in the genome of the plant cell, one or more single-stranded breaks in the genome of the plant cell, one or more base-editing events in the genome of the plant cell, or one or more of DNA methylation, histone acetylation, histone methylation, histone ubiquitination, histone phosphorylation, histone sumoylation, histone ribosylation or histone citrullination in the genome of the plant cell. The resulting modification in the genome of the plant cell can, for example, be selected from a replacement of at least one nucleotide, a deletion of at least one nucleotide, an insertion of at least one nucleotide, a change of DNA methylation, a change in histone acetylation, histone methylation, histone ubiquitination, histone phosphorylation, histone sumoylation, histone ribosylation, or histone citrullination or any combination thereof.

Alternatively to the direct or indirect chemical induction of the heterologous promoter operatively linked to the polynucleotide sequence encoding the RKD2 polypeptide or the RKD4 polypeptide the transient expression can be also achieved by means of one or more site-directed transcriptional activators. Such site-directed transcriptional activator can be a synthetic transcription factor described in U.S. Provisional Applications No. 62/609,508 and No. 62/758,068, incorporated by reference herein. The synthetic transcription factor can comprise at least one recognition domain and at least one gene expression modulation domain, in particular an activation domain, wherein the synthetic transcription factor is configured to modulate the expression of an endogenous gene in the genome of plant or plant cell. Such an endogenous gene is preferably a (native) morphogenic gene which encodes polypeptides involved in plant developmental processes like root formation or shoot formation. In some embodiments, the endogenous morphogenic gene is selected from the group consisting of an endogenous nucleic acid encoding an RKD4 polypeptide or an endogenous nucleic acid encoding an RKD2 polypeptide. In some embodiments, the at least one recognition domain is, or is a fragment of, a molecule selected from the group consisting of at least one TAL effector, at least one disarmed CRISPR/nuclease system, at least one Zinc-finger domain, and at least one disarmed homing endonuclease, or any combination thereof.

In some embodiments, the at least one disarmed CRISPR/nuclease system is a CRISPR/dCas9 system, a CRISPR/dCpf1 system, a CRISPR/dCsm1 system, a CRISPR/dMAD7 system, a CRISPR/dCasX system or a CRISPR/dCasY system, or any combination thereof, and wherein the at least one disarmed CRISPR/nuclease system comprises at least one guide RNA.

In some embodiments, the at least one activation domain is selected from the group consisting of an acidic transcriptional activation domain, preferably, wherein the at least one activation domain is from a TAL effector gene of *Xanthomonas oryzae*, VP16 or tetrameric VP64 from Herpes simplex, VPR, SAM, Scaffold, Suntag, P300, VP160, or any combination thereof. In some embodiments, the activation domain is VP64.

In some embodiments, the synthetic transcription factor is configured to modulate expression, preferably transcription, of the morphogenic gene by binding to a regulation region located at a certain distance in relation to the start codon. In preferred embodiments, the synthetic transcription factor is configured to increase expression, preferably transcription, of the morphogenic gene by binding to a regulation region located at a certain distance in relation to the start codon.

In some embodiments, the site-directed transcriptional activator/synthetic transcription factor, or the nucleic acid encoding the same, comprises at least one recognition domain and at least one activation domain, wherein the site-directed transcriptional activator is configured to increase the expression of an endogenous RKD4 polypeptide or an endogenous RKD2 polypeptide, preferably by binding to a regulation region located at a certain distance in relation to the start codon of the endogenous RKD4 polypeptide or the endogenous RKD2 polypeptide.

The "regulation region" as used herein refer to the binding site of at least one recognition domain to a target sequence in the genome at or near a morphogenic gene. There may be two discrete regulation regions, or there may be overlapping regulation regions, depending on the nature of the at least one activation domain and the at least one recognition domain as further disclosed herein, which different domains of the synthetic transcription factor can be assembled in a modular manner.

In certain embodiments, the at least one recognition domain may target at least one sequence (recognition site) relative to the start codon of a gene of interest, which sequence may be at least 1000 bp upstream (−) or downstream (+), −700 bp to +700 bp, −550 bp to +500 bp, or −550 bp to +425 bp relative to of the start codon of a gene of interest. Promoter-near recognizing recognition domains might be preferable in certain embodiments, whereas it represents an advantage of the specific synthetic transcription factors that the targeting range of the synthetic transcription factors is highly expanded over conventional or naturally occurring transcription factors. As the recognition and/or the activation domains can be specifically designed and constructed to specifically identify and target hot-spots of modulation.

In certain embodiments, the at least one recognition site may be −169 bp to −4 bp, −101 bp to −48 bp, −104 to −42 bp, or −175 to +450 bp (upstream (−) or downstream (+), respectively) relative to the start codon of a gene of interest to provide an optimum sterical binding environment allowing the best modulation, preferably transcriptional activation, activity. In particular for CRISPR-based synthetic transcription factors acting together with a guide RNA as recognition moiety, the binding site can also reside in within the coding region of a gene of interest (downstream of the start codon of a gene of interest).

In further embodiments, the recognition domain of the synthetic transcription factor can bind to the 5' and/or 3' untranslated region (UTR) of a gene of interest. In embodiments where different recognition domains are employed, the at least two recognition domains can bind to different target regions of a morphogenic gene, including 5' and/or 3'UTRs, but they can also bind outside the gene region, but still in a certain distance of at most 1 to 1500 bps thereto. One preferred region where a recognition domain can bind resides about −4 bp to about −300, preferably about −40 bp to about −170 bp upstream of the start codon of a morphogenic gene of interest. Furthermore, the length of a recognition domain and thus the corresponding recognition site in a genome of interest may thus vary depending on the synthetic transcription factor and the nature of the recognition domain applied. Based on the molecular characteristics of the at least one recognition domain, this will also determine the length of the corresponding at least one recognition site. For example, where individual zinc finger may be from about 8 bp to about 20 bp, wherein arrays of between three to six zinc finger motifs may be preferred, individual TALE recognition sites may be from about 11 to about 30 bp, or more. Recognition sites of gRNAs of a CRISPR-based synthetic transcription factor comprise the targeting or "spacer" sequence of a gRNA hybridizing to a genomic region of interest, whereas the gRNA comprises further domains, including a domain interacting with a disarmed CRISPR effector. The recognition site of a synthetic transcription factor based on a disarmed CRISPR effector will comprise a PAM motif, as the PAM sequence is necessary for target binding of any CRISPR effector and the exact sequence is dependent upon the species of the CRISPR effector, i.e., a disarmed CRISPR effector.

Introduction of RKD2 or RKD4 Genes

The nucleic acids encoding RKD2 or RKD4 and/or genome engineering components can be introduced as DNA such as plasmid DNA, RNA, mRNA or RNP.

The RKD2 or RKD4 genes may be co-delivered with one or more genome engineering components. As used herein, "co-delivery" or "co-deliver" and "co-introduction" or "co-introduce" are used interchangeably. In terms of the present invention, "co-introducing" refers to the process in which at least two different components are delivered into the same plant cell concurrently. Thus, the genome engineering components, and RKD2 and/or RKD4, are introduced together into the same plant cell. Co-introduction into the plant cell can be conducted by particle bombardment, microinjection, *agrobacterium*-mediated transformation, electroporation, electrofusion, agroinfiltration or vacuum infiltration.

It is believed that transformed cells are less regenerable than wild type cells. Transformed cells are susceptible to programmed cell death due to presence of foreign DNA inside of the cells. Stresses arising from delivery (e.g., bombardment damage) may trigger a cell death as well. Therefore, promoting cell division is essential for the regeneration of the modified cells. Further, genome engineering efficiency is controlled largely by host cell statuses. Cells undergoing rapid cell-division, like those in plant meristem, are the most suitable recipients for genome engineering. Promoting cell division will probably increase DNA integration or modification during DNA replication and division process, and thus increase genome engineering efficiency.

When an RKD2 or RKD4 polypeptide is expressed in a plant cell along with a transgene, the RKD2 or RKD4 polypeptide can increase expression of the transgene and polypeptides encoded by the transgene. When an RKD2 or RKD4 polypeptide is expressed in a plant cell along with a genome engineering component and the transgene, the activity of the genome engineering component may be increased. Such increase may result in more efficient integration of the transgene into the genome of the plant cell.

The RKD4 polypeptide coding sequence can be from any number of plants known in the art. Such plants include, but are not limited to, *Zea mays, Arabidopsis thaliana*, and *Triticum aestivum*. In some embodiments, the RKD4 polypeptide coding sequence is from *Triticum aestivum* RKD4. In some embodiments, the RKD4 polypeptide coding sequence is from *Arabidopsis thaliana* RKD4. In some embodiments, the RKD4 polypeptide coding sequence is from *Zea mays* RKD4. In some embodiments, the RKD2 polypeptide coding sequence is from *Triticum aestivum* RKD2. In some embodiments, the RKD2 polypeptide coding sequence is from *Arabidopsis thaliana* RKD2. In some embodiments, the RKD2 polypeptide coding sequence is from *Zea mays* RKD2.

For the purpose of this invention, the "sequence identity" of two related nucleotide or amino acid sequences, expressed as a percentage, refers to the number of positions in the two optimally aligned sequences which have identical residues ($\times100$) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as program NEEDLE as implemented in the European Molecular Biology Open Software Suite (EMBOSS), e.g., version 6.3.1.2 (Trends in Genetics 16 (6), 276 (2000)), with its default parameter, e.g., for proteins matrix=EBLOSUM62, gapopen=10.0 and gapextend=0.5.

As used herein, the term "hybridize(s)(ing)" refers to the formation of a hybrid between two nucleic acid molecules via base-pairing of complementary nucleotides. The term "hybridize(s)(ing) under stringent conditions" means hybridization under specific conditions. An example of such conditions includes conditions under which a substantially complementary strand, namely a strand composed of a nucleotide sequence having at least 80% complementarity, hybridizes to a given strand, while a less complementary strand does not hybridize. Alternatively, such conditions refer to specific hybridizing conditions of sodium salt concentration, temperature and washing conditions. As an example, highly stringent conditions comprise incubation at 42° C., 50% formamide, 5×SSC (150 mM NaCl, 15 mM trisodium citrate), 50 mM sodium phosphate, 5×Denhardt's solution, 10×dextran sulfate, 20 mg/ml sheared salmon sperm DNA and washing in 0.2×SSC at about 65° C. (SSC stands for 0.15 M sodium chloride and 0.015 M trisodium citrate buffer). Alternatively, highly stringent conditions may mean hybridization at 68° C. in 0.25 M sodium phosphate, pH 7.2, 7% SDDS, 1 mM EDTA and 1% BSA for 16 hours and washing twice with 2×SSC and 0.1% SDDS at 68° C. Further alternatively, highly stringent hybridisation conditions are, for example: Hybridizing in 4×SSC at 65° C. and then multiple washing in 0.1×SSC at 65° C. for a total of approximately 1 hour, or hybridizing at 68° C. in 0.25 M sodium phosphate, pH 7.2, 7% SDS, 1 mM EDTA and 1% BSA for 16 hours and subsequent washing twice with 2×SSC and 0.1% SDS at 68° C.

Epigenetically-Regulating Chemicals

An epigenetically regulating chemical, e.g., protein deacetylase inhibitor (ii.1), can be co-introduced with the genome engineering component. Exemplary epigenetically regulating chemicals for use according to the invention include, but are not limited to, histone deacetylase inhibitors (HDACis) such as trichostatin A (TSA), and DNA methyltransferase inhibitors.

It is assumed that the co-delivered epigenetically regulating chemicals (ii.1) (in particular HDACis) relax plant chromatin structure, promote the DNA accessibility to the genome engineering components in the bombarded cells, thus consequently promote genome engineering (i.e. transformation and genome editing) efficiencies. Without wishing to be bound by theory, the basic structural and functional unit of genetic material is the nucleosome, in which negatively charged DNA is wrapped around a positively charged histone octamer and associated linker histones. Nucleosome units further fold and pack into chromatin (Andrews, A. J., and Luger, K. (2011). Nucleosome structure(s) and stability: Variations on a theme. Annu. Rev. Biophys. 40: 99-117.). DNA accessibility largely depends on compactness of the nucleosomes and chromatins. Chromatin-remodeling enzymes dynamically modify lysine or other amino acids of histones, which cause changes in their charges and interactions with DNA and other proteins, and result in chromatin folding or unfolding (Bannister A. J., Kouzarides T. (2011) Regulation of chromatin by histone modifications. Cell Res 21: 381-95.). By adding or removing an acetyl group, acetylation and deacetylation of the lysine residue in histone proteins are often involved in the reversible modulation of chromatin structure in eukaryotes, and mediate chromatin accessibility and the regulation of gene expression. Histone deacetylases (HDAC) are enzymes that remove acetyl groups from lysine resides on the N-terminal tail of histones, which makes the histone more positively charged, and therefore allows the histone to wrap DNA more tightly. Inhibition of HDACs might help chromatin unfolding and enable the DNA to be more accessible.

Chromatin remodeling and other epigenetic modifications surely play an important role in regulating cell totipotency and regeneration (Zhang, H., and Ogas, J. (2009). An epigenetic perspective on developmental regulation of seed genes. Mol. Plant 2: 610-627.). Inhibition of histone deacetylase (HDAC) activities have been shown associated with plant regeneration and microspore embryogenesis (Miguel, C., and Marum, L., 2011. An epigenetic view of plant cells cultured in vitro: somaclonal variation and beyond. J. Exp. Bot. 62:3713-3725., Li Hui et al. (2014) The Histone Deacetylase Inhibitor Trichostatin A Promotes Totipotency in the Male Gametophyte Plant Cell, 26: 195-209.). Inhibition of HDAC activity or downstream HDAC-mediated pathways plays a major role in the initiation of stress-induced haploid embryogenesis. One such HDACi is trichostatin A (TSA). It has been shown that TSA induces massive embryogenic cell proliferation in the male gametophyte of *B. napus*. TSA treatment leads to a high frequency of sporophytic cell division in cultured microspores and pollen.

Various methods may be used to increase further the genome engineering efficiency in presence of one or more epigenetically regulating chemicals, e.g., protein deacetylase inhibitors, in particular HDACi. Such an HDACi may be trichostatin A (TSA), N-Hydroxy-7-(4-dimethylamino-benzoyl)-aminoheptanamide (M344), suberoylanilide hydroxamic acid (SAHA), or others. These HDACis are selected from hydroxamic acid (HA)-based chemicals, which target to zinc dependent HDACs.

Phytohormones

In various embodiments, one or more phytohormones, such as auxins and cytokinins like 2,4-D, 6-Benzylaminopurine (6-BA) and Zeatin, are co-delivered with one or more of a nucleic acid encoding RKD2 or RKD4, a genome engineering component, and a transgene.

Plant somatic cells are able to resume cell division and regenerate into an entire plant in in-vitro culture through somatic embryogenesis or organogenesis, which largely depends on phytohormones, such as auxins and cytokinins.

One of auxins is 2,4-Dichlorophenoxyacetic acid (2,4-D), which is nearly indispensable for somatic embryogenesis and cell regeneration in monocot plants, e.g., maize and wheat. Meanwhile, cytokinins, e.g., 6 benzylaminopurine (6-BA) or Zeatin, are essential for plant organogenesis, and shoot meristem initiation and development. The methods to improve genome engineering efficiency may include co-delivery of one or more of phytohormones (2,4-D, 6-BA, Zeatin, etc.) with the genome engineering component.

A genome engineering component and at least one of the epigenetically-regulating chemicals and phytohormones can be co-introduced into one plant cell.

As used herein, "co-delivery" or "co-deliver" and "co-introduction" or "co-introduce" are used interchangeably. In terms of the present invention, "co-introducing" refers to the process, in which at least two different components are delivered into the same plant cell concurrently. Thus, the genome engineering component and at least one of the epigenetically-regulating chemicals and phytohormones may be introduced together into the same plant cell.

Co-introduction into the plant cell can be conducted by particle bombardment, microinjection, *agrobacterium*-mediated transformation, electroporation, agroinfiltration or vacuum infiltration. According to the invention, methods based on physical delivery like particle bombardment, microinjection, electroporation, nanoparticles, and cell-penetrating peptides (CPPs) are particularly preferred for co-introducing a nucleic acid encoding RKD2 or RKD4, genome engineering components, and/or transgenes. Particularly preferred is the co-introduction via particle bombardment.

Regeneration of a Plant Cell into a Whole Plant

According to another aspect of the present invention, the genetically modified plant cells can be regenerated into a whole (fertile) plant. Thus, in a preferred aspect of the invention, the genetic modification of a plant cell is followed by a step of regenerating a plant. Accordingly, the present invention provides a method for producing a genetically modified plant comprising the steps:

a) genetically modifying a plant cell according to any of the above methods for genetic modification in a plant cell, and b) regenerating a plant from the modified plant cell of step a), Single or multiple cells proliferate and develop into tissues, organs, and eventually entire plants. In some embodiments, the produced plant does not contain any of the genome engineering components, nucleic acids encoding RKD2 or RKD4 introduced, or co-introduced in step a). Step b) of regenerating a plant can for example comprise culturing the genetically modified plant cell from step a) on a regeneration medium.

The efficiency of plant regeneration or of increasing the regeneration ability of a plant cell can be improved by introducing into the plant cell any of the nucleic acids encoding RKD2 or RKD4, recombinant genes and DNA constructs described herein.

Production of a Genetically Modified Plant

The present invention also provides a genetically modified plant obtained or obtainable by the above methods for producing a genetically modified plant or a progeny plant thereof. The genetically modified plant may comprise any of the genetically modified plant cells described herein.

In various embodiments, the produced plant does not contain any of the genome engineering components or nucleic acids encoding RKD2 or RKD4 introduced or co-introduced into a plant cell used to generate the produced plant.

The present invention also provides a plant or a seed derived from the above-described genetically modified cells without a conventional selection. As used herein, "conventional selection" refers to any processes to select and purify the transformed cells from wild-type cells by using an integrated selection marker, e.g., antibiotic (e.g., kanamycin, hygromycin), or herbicide (e.g., phosphinothricin, glyphosate) resistance gene. Without a conventional selection, such a plant or seed may not have any of the genome engineering components integrated, and thus leads to transgene-free genetic modified plants.

The genetic modification can be a permanent and heritable change in the genome of the plant cell. Plant tissue culture and genome engineering can be carried out using currently available methods, comprising of microparticle bombardment, *Agrobacterium* transformation, electroporation, etc. Transformation and transgene expression may be monitored by use of a visible report gene, for example, the red fluorescent tDTomato gene (tDT) that encodes an exceptionally bright red fluorescent protein with excitation maximum at 554 nm and emission maximum at 581 nm. The genome editing efficiency can be analyzed for instance by next generation sequencing (NGS), qPCR, marker capillary electrophoresis analysis, and Droplet Digital PCR. Site-specific modification was further conformed by Sanger sequencing.

Cultivation Step

The plant cell into which nucleic acids encoding RKD2 or RKD4, genome engineering components, and/or transgenes have been introduced, or co-introduced, can be cultivated under conditions allowing the genetic modification of the genome of said plant cell by activity of the genome engineering component in the presence of one or more of nucleic acids encoding RKD2 or RKD4, and one or more transgenes.

As used herein, "genetic modification of the genome" includes any type of manipulation such that endogenous nucleotides have been altered to include a mutation, such as a deletion, an insertion, a transition, a transversion, or a combination thereof. For instance, an endogenous coding region could be deleted. Such mutations may result in a polypeptide having a different amino acid sequence than was encoded by the endogenous polynucleotide. Another example of a genetic modification is an alteration in the regulatory sequence, such as a promoter, to result in increased or decreased expression of an operably linked endogenous coding region.

Conditions that are "suitable" for a genetic modification of the plant genome to occur, such as cleavage of a polynucleotide, or "suitable" conditions are conditions that do not prevent such events from occurring. Thus, these conditions permit, enhance, facilitate, and/or are conducive to the event. Depending on the respective genome engineering component (i), these conditions may differ.

In the method of the present invention, the plant cell is preferably transiently transformed with the genome engineering component (i) and the at least one compound (ii). As used herein, "transient transformation" refers to the transfer of a foreign material [i.e. a nucleic acid fragment, protein, ribonucleoprotein (RNP), etc.] into host cells resulting in gene expression and/or activity without integration and stable inheritance of the foreign material. Thus, the genome engineering component (i) is transiently active and/or transiently present in the plant cell. The genome engineering component is not permanently incorporated into the cellular genome, but provides a temporal action resulting in a modification of the genome. For example, transient activity and/or transient presence of the genome engineering component in the plant cell can result in introducing one or more double-stranded breaks in the genome of the plant cell, one or more single-stranded breaks in the genome of the plant cell, one or more base-editing events in the genome of the plant cell, or one or more of DNA methylation, histone acetylation, histone methylation, histone ubiquitination, histone phosphorylation, histone sumoylation, histone ribosylation or histone citrullination in the genome of the plant cell.

The introduction of one or more double-stranded breaks or one or more single-stranded breaks is preferably followed by non-homologous end joining (NHEJ) and/or by homology directed repair (HDR) of the break(s) through a homologous recombination mechanism.

The resulting modification in the genome of the plant cell can, for example, be selected from an insertion of a transgene, preferably an expression cassette comprising a transgene of interest, a replacement of at least one nucleotide, a deletion of at least one nucleotide, an insertion of at least one nucleotide, a change of DNA methylation, a change in histone acetylation, histone methylation, histone ubiquitination, histone phosphorylation, histone sumoylation, histone ribosylation, or histone citrullination or any combination thereof. According to a particularly preferred aspect of the invention, no exogenous genetic material related to the applied gene editing machinery/systems is stably integrated into the genome of the plant cell.

The genetic modification can be a permanent and heritable change in the genome of the plant cell.

Subject matter of the present invention are also the plant cells that are obtained or obtainable by the methods described above. Accordingly, one embodiment of the invention is a genetically modified plant cell obtained or obtainable by the above method for genetic modification in a plant cell. The genetic modification in these plant cells compared to the original plant cells may, for example, include an insertion of a transgene, preferably an expression cassette comprising a transgene of interest, a replacement of at least one nucleotide, a deletion of at least one nucleotide, an insertion of at least one nucleotide, a change of DNA methylation, a change in histone acetylation, histone methylation, histone ubiquitination, histone phosphorylation, histone sumoylation, histone ribosylation, or histone citrullination or any combination thereof. Preferably, the genetically modified plant cell does not comprise any exogenous genetic materials stably integrated into the genome of the plant cell.

Genetically modified plant cells can be part of a whole plant or part thereof. Thus, the present invention also relates to a plant or plant part comprising the above genetically modified plant cell.

According to another aspect of the present invention, the genetically modified plant cells can be regenerated into a whole (fertile) plant. Thus, in a preferred aspect of the invention, the genetic modification of a plant cell is followed by a step of regenerating a plant. Accordingly, the present invention provides a method for producing a genetically modified plant comprising the steps:

a) genetically modifying a plant cell according to the above method for genetic modification in a plant cell, and b) regenerating a plant from the modified plant cell of step a).

Step b) of regenerating a plant can for example comprise culturing the genetically modified plant cell from step a) on a regeneration medium.

Regeneration techniques rely on manipulation of certain phytohormones in a tissue culture growth medium, occasionally relying on a biocide and/or herbicide marker that can be introduced. Regeneration can be obtained from plant somatic cells, callus cells or embryonic cells and protoplasts derived from different explants, e.g., callus, immature or mature embryos, leaves, shoot, roots, flowers, microspores, embryonic tissue, meristematic tissues, organs, or any parts thereof. Such regeneration techniques are described generally in Klee (1987) Ann. Rev. of Plant Phys. 38:467-486. Plant regeneration from cultured protoplasts is described in Evans et al., Protoplasts Isolation and Culture, Handbook of Plant Cell Culture, pp. 124-176, Macmillan Publishing Company, New York, 1983; and Binding, Regeneration of Plants, Plant Protoplasts, pp. 21-73, CRC Press, Boca Raton, 1985. To obtain whole plants from transformed or gene edited cells, the cells can be grown under controlled environmental conditions in a series of media containing nutrients and hormones, a process known as tissue culture. Once whole plants are generated and produce seed, evaluation of the progeny begins.

The present invention also provides a genetically modified plant obtained or obtainable by the above method for producing a genetically modified plant or a progeny plant thereof.

Further subject matter of the present invention is a plant cell or a seed derived from the above genetically modified plant.

Further subject matter of the present invention is a plant, plant cell or a seed derived from the above genetically modified cell without a marker gene-based selection. As used herein, "marker gene-based selection" refers to any processes to select, identify and/or purify the modified cells, in particular the transformed, gene edited or base edited cells, from wild-type cells by using an integrated selection marker (gene), e.g., antibiotic resistance gene (e.g., kanamycin resistance gene, hygromycin resistance gene), or herbicide resistance gene (e.g., phosphinothricin resistance gene, glyphosate resistance gene). Without such selection, such a plant, plant cell or seed may not have any of the genome engineering components integrated, which may yield (i) transgene-free genetic modified plants or (ii) modified plants which have integrated solely the transgene of interest.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Cray, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR-Basics: From Background to Bench, First Edition, Springer Verlag, Germany.

| Sequences | |
|---|---|
| SEQ ID NO: | Description |
| 1 | cDNA of AtRKD4 |
| 2 | AtRKD4 protein |
| 3 | cDNA of TaRKD2 genotype 1 |
| 4 | cDNA of TaRKD2 genotype 2 |
| 5 | TaRKD2 protein |
| 6 | cDNA of AtLEC2 |
| 7 | AtLEC2 protein |
| 8 | cDNA of AtWUS |
| 9 | AtWUS protein |
| 10 | cDNA of AtBBM |
| 11 | AtBBM protein |
| 12 | cDNA of AtAGL 15 |
| 13 | AtAGL15 protein |
| 14 | pERV1-hygro carrying TaRKD2 as CDS |
| 15 | pOP6 promoter |
| 16 | cDNA of LhGR |
| 17 | LhGR protein |
| 18 | cDNA tdTomato |
| 19 | tdTomato protein |
| 20 | Ubiquitin intron |
| 21 | double 35S promoter |
| 22 | XVE/OLexA system |
| 23 | ubiquitin promoter |

All patents, patent applications, and publications or public disclosures (including publications on internet) referred to or cited herein are incorporated by reference in their entirety.

EXAMPLES

The present invention is further illustrated by the following examples. However, it is to be understood that the invention is not limited to such examples. The use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. Preparation of pZY ZZ-TOP, a Plasmid with a Bidirectional Promoter pOp6 Operably Linked to a Developmental Gene and a GUS Reporter Gene, as Well as a Dexamethasone-Inducible Transcription Factor that Activates pOp6

A plasmid (pZY ZZ-TOP) is generated that harbors a chemically (Dexamethasone, Dex) inducible promoter system (Zuo, J., & Chua, N. H. (2000). Chemical-inducible systems for regulated expression of plant genes. *Current Opinion in Biotechnology*, 11(2), 146-151.) A map of the plasmid is shown in FIG. 1. The plasmid comprises a pOp6 promoter (SEQ ID NO: 15). The pOp6 promoter is bidirectional and, upon dexamethasone exposure (Sigma-Aldrich. Product #D4902-500MG), both a developmental gene as well as a GUS gene are expressed (FIG. 1). The plasmid also comprises the gene LhGR (DNA (SEQ ID NO: 16 and amino acid (SEQ ID NO: 17)). LhGR is expressed constitutively (e.g., pUbi1 promoter+intron). LhGR is a transcription factor that will only enter the nucleus in presence of dexamethasone. After entering the nucleus, LhGR activates the pOp6. Accordingly, the pZY ZZ-TOP provides for dexamethasone-inducible expression of GUS and the developmental gene.

This expression system is used for stable transformation. GUS staining is used to identify leaky expression without chemical induction. In all subsequent examples, only plants that did not express the GUS gene without chemical induction were considered. Plants that expressed GUS without chemical induction were not used.

Example 2. Assessment of Transcription Factors for Ability to Induce Plant Regeneration by Somatic Embryogenesis In a further example, five different transcription factors were tested for their efficiency of inducing plant regeneration via somatic embryogenesis. The coding sequences of AtLEC2 (SEQ ID NO: 6), AtWUS (SEQ ID NO: 8), AtBBM (SEQ ID NO: 10), AtAGL15 (SEQ ID NO: 12), and AtRKD4 (SEQ ID NO: 1) were cloned into the inducible promoter system pZY ZZ-TOP of Example 1. The expression of each of AtLEC2, AtWUS, AtBBM, AtAGL15 and AtRKD4 was inducible by dexamethasone.

These dexamethasone-inducible binary constructs based on the pOp6/LhGR transactivation system were stably transformed into *Arabidopsis thaliana* Col-0 by floral dip (Craft et al. (2005). New pOp/LhG4 vectors for stringent glucocorticoid-dependent transgene expression in *Arabidopsis*. The Plant Journal, 41(6), 899-918.). *Arabidopsis thaliana* Col-0 was grown under controlled environment conditions (16 h light/8 h dark, 22° C.) in plates containing 50% MS media supplemented with 1% sucrose. Forty independent transgenic lines were tested for leaky expression by GUS staining.

Non-leaky transformants were induced 5 to 7 days after germination. Chemical induction of gene expression was carried out by growing plants on plates containing 20 uM dexamethasone for 7 days and then transferring plants to media without inducer. The frequency of somatic embryos was determined by microscopy imaging after staining with Sudan Red 7B.

Figure 2:
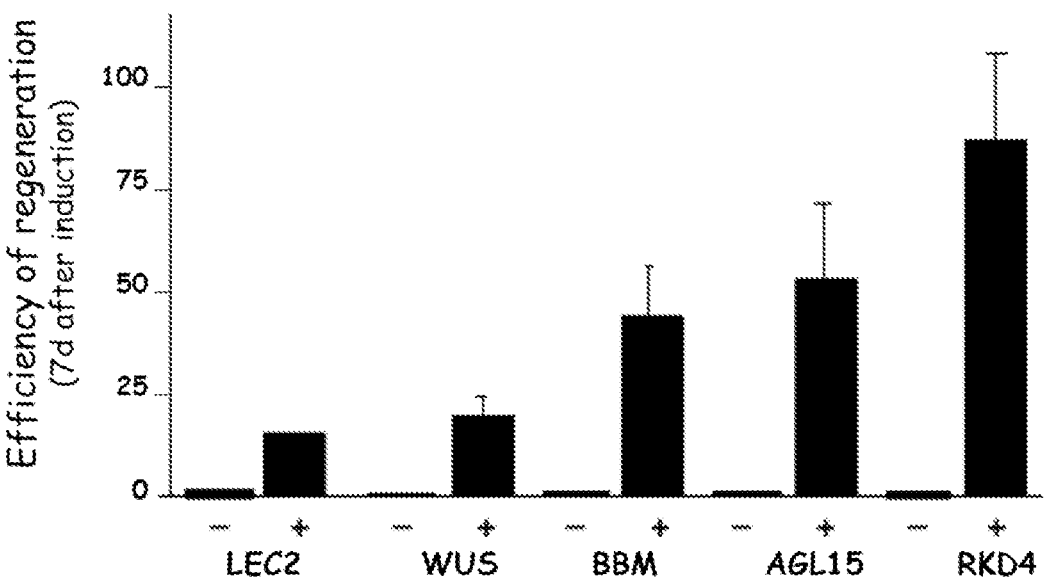
FIG. 2 is a graph showing a comparison of the efficiency of regeneration mediated by various developmental genes under a chemically inducible promoter system after induction. Plants were transformed with a pZY ZZ-TOP plasmid in which different developmental genes (i.e. LEC2, WUS, BBM, AGL15 and RKD4) were inserted into the plasmid. Some plants were treated with dexamethasone to induce expression of the developmental genes (as indicted by "+" on the X-axis), while other plants were not so treated ("−"). The efficiency of regeneration on the y-axis refers to the frequency of somatic embryo formation.

The results are shown in FIG. 2. RKD4 has the highest efficiency to form embryogenic structures upon Dexamethasone exposure.

Figure 3:
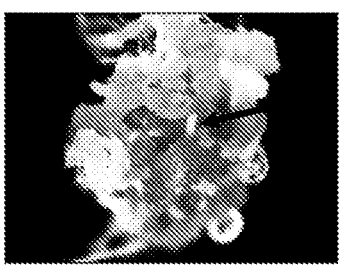
FIG. 3 shows somatic embryo formation induced in *Arabidopsis thaliana* plants expressing RKD4 in the above pOp6/LhGR transactivation system. Somatic embryo formation was observed in the root (left panel), leaves (middle panel), or both root and leaves (right panel).
Figure 3:
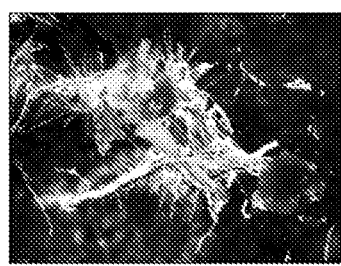
Figure 3:
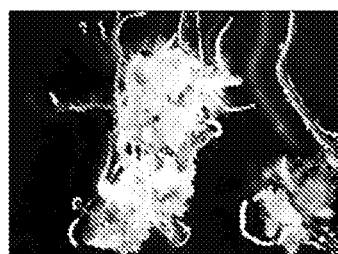

Example 3. RKD4 Expressed in the pOp6/LhGR Transactivation System is Capable of Dexamethasone-Induced Somatic Embryogenesis The functionality of the inducible promoter system controlling RKD4 was tested in *Arabidopsis thaliana*. *Arabidopsis* seeds were germinated until formation of a primary root. The plantlets were then transferred onto Dex-containing plates (as described in Example 2). The plantlets were imaged, with the data shown in FIG. 3. Somatic embryo formation was observed in the root (FIG. 3, left panel), the leaves (FIG. 3, middle panel), or both (FIG. 3, right panel). A loss of chlorophyll can also be observed. After moving the structures to Dex-free media, the somatic embryo structures start to green again. These data demonstrate that RKD4 expression is able to induce somatic embryogenesis in the absence of hormones.

Figure 4:
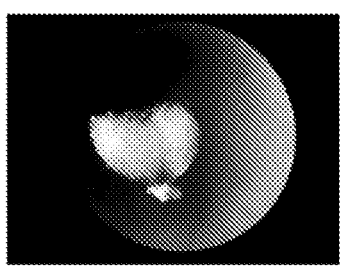
FIG. 4 shows AtRKD4-mediated regeneration of *Phalaenopsis amabilis* plants after Dexamethasone-induced expression of AtRKD4 in basal parts of the leaves. Presence of somatic embryo (arrow) was determined after 0 (left), 7 (middle) and 14 days (right) after removal of dexamethasone from medium.
Figure 4:
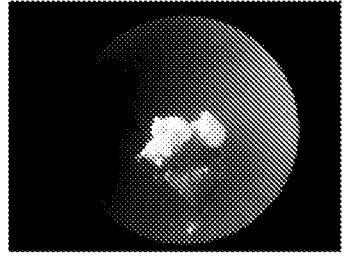
Figure 4:
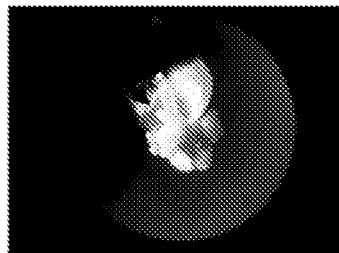

Example 4. AtRKD4 Expressed in the pOp6/LhGR Transactivation System can Induce Somatic Embryo Formation in a Horticulturally Relevant Species The horticulturally relevant species of *Phalaenopsis amabilis* was transformed using *Agrobacterium tumefaciens* GV3101 with a dexamethasone-inducible AtRKD4 binary construct as described in Example 1. Basal parts of the leaves of stably transformed plants were incubated for two days in plates containing 50% MS media containing 20 μM dexamethasone, and then transferred to media lacking dexamethasone. The presence of a somatic embryo was determined after 0, 7 and 14 days after transfer, with the data shown in FIG. 4.

Example 5. AtRKD4 Expressed in the pOp6/LhGR Transactivation System can Induce Somatic Embryo Formation in an Agriculturally Relevant Species of *Triticum aestivum*

Figure 5:
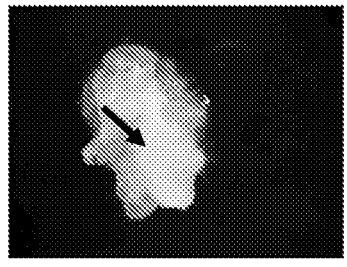
FIG. 5 shows estradiol-induced expression of TaRKD2 in *Triticum aestivum* plants. Induction and development of embryogenic structures have been observed: callus formation (left panel, arrow), greening (middle panel), and emerging leaves (right panel, arrows).
Figure 5:
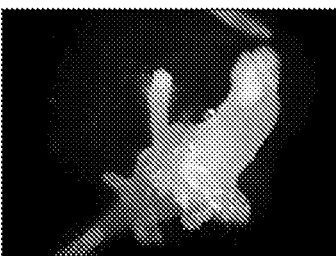
Figure 5:

The effect of induced RKD4 expression in the agriculturally relevant species of *Triticum aestivum* was assayed. Wheat immature embryos were transformed with *Agrobacterium* EHA105 carrying an estradiol-inducible TaRKD2 (SEQ ID NO: 3) binary construct (Valdivia et al., 2013). Transformed embryos were isolated from seed 12 days after pollination and were grown in 50% MS media containing 30 uM β-estradiol for 7 days. The induction of embryogenic structures could be observed in that media (callus formation; FIG. 5, left panel). The embryonic structures were transferred to media without inducer so as to induce somatic embryos. Greening was observed (FIG. 5, middle panel), followed by emerging leaves (FIG. 5, right panel). The example demonstrates an effect of RKD4 expression in an agriculturally relevant species.

Figure 6:
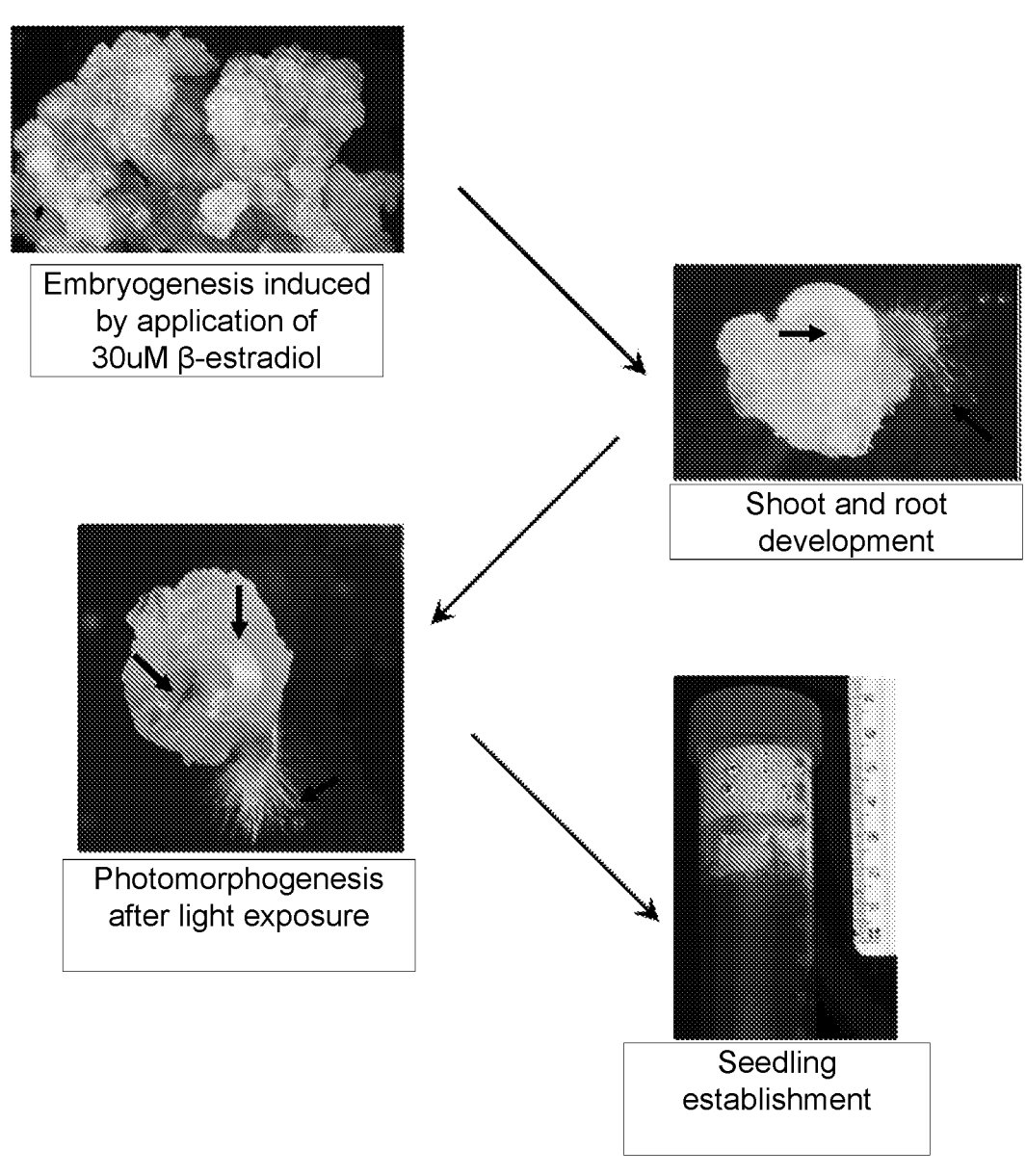
FIG. 6 shows estradiol-induced expression of TaRKD2 in *Hordeum vulgare* plants. Induction and development of embryogenic structures have been observed: callus formation (upper left panel), shoot and root development (upper right panel, arrow), greening (bottom left panel) and seedling formation (bottom right panel).

Example 6. Expression of TaRKD2 in *Hordeum vulgare* Immature Embryos could Induce Somatic Embryo Formation In one further example, *Hordeum vulgare* immature embryos were transformed with *Agrobacterium* EHA105 carrying an estradiol-inducible TaRKD2 (SEQ ID NO: 3) binary construct (Valdivia et al., 2013). Transformed immature barley embryos were isolated from seed and were grown in 50% MS media containing 30 uM β-estradiol for 7 days (FIG. 6, upper left panel) and then transferred to media without inducer to induce somatic embryos. After removing the embryogenic structures from the inducing media, shoot and root development could be observed (FIG. 6, upper right panel). Subsequently, the structures were moved into the light, where the tissues started to green (FIG. 6, bottom left panel). About 60 days after initial immature embryo isolation, seedlings could be established (FIG. 6, bottom right panel).

Example 7. Co-Expression of RKD2 and RKD4 in *Zea mays*

Figure 7:
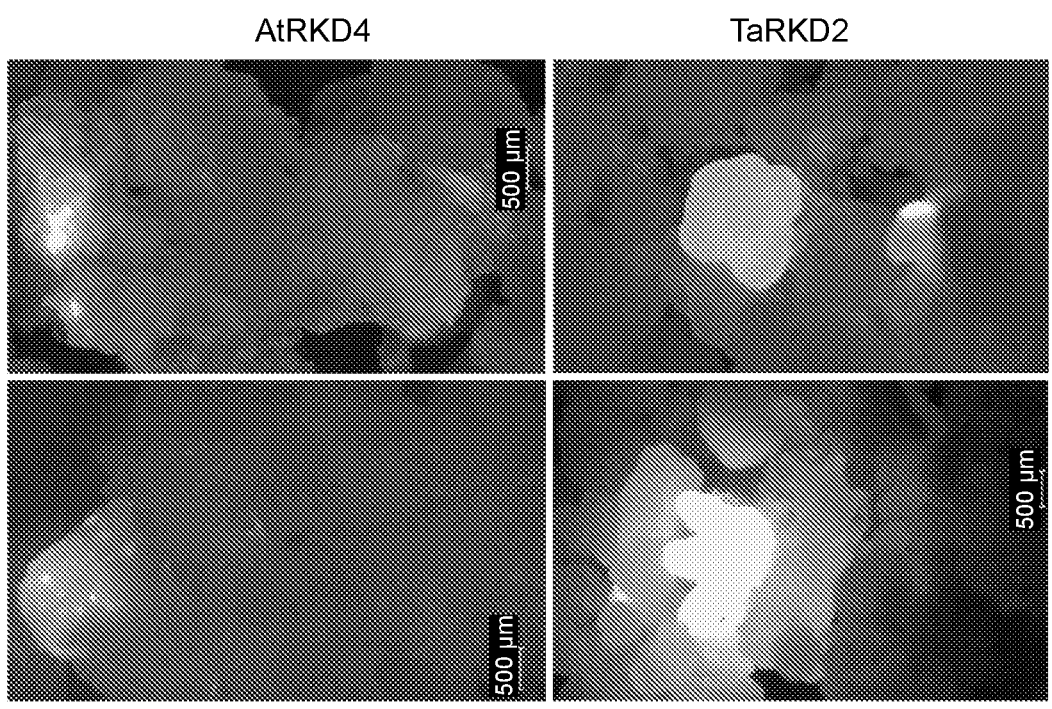
FIG. 7 shows dexamethasone-induced expression of AtRKD4 and TaRKD2 in *Zea mays*. The dexamethasone-inducible construct (see Example 1) was co-bombarded with the red fluorescent tdTomato gene under a constitutive promoter. Upon exposure to dexamethasone, the induction of formation of massive callus structures with stable tdTomato integration can be observed after 33 days post bombardment for AtRKD4 (left panels) and TaRKD2 (right panels).
Figure 8:
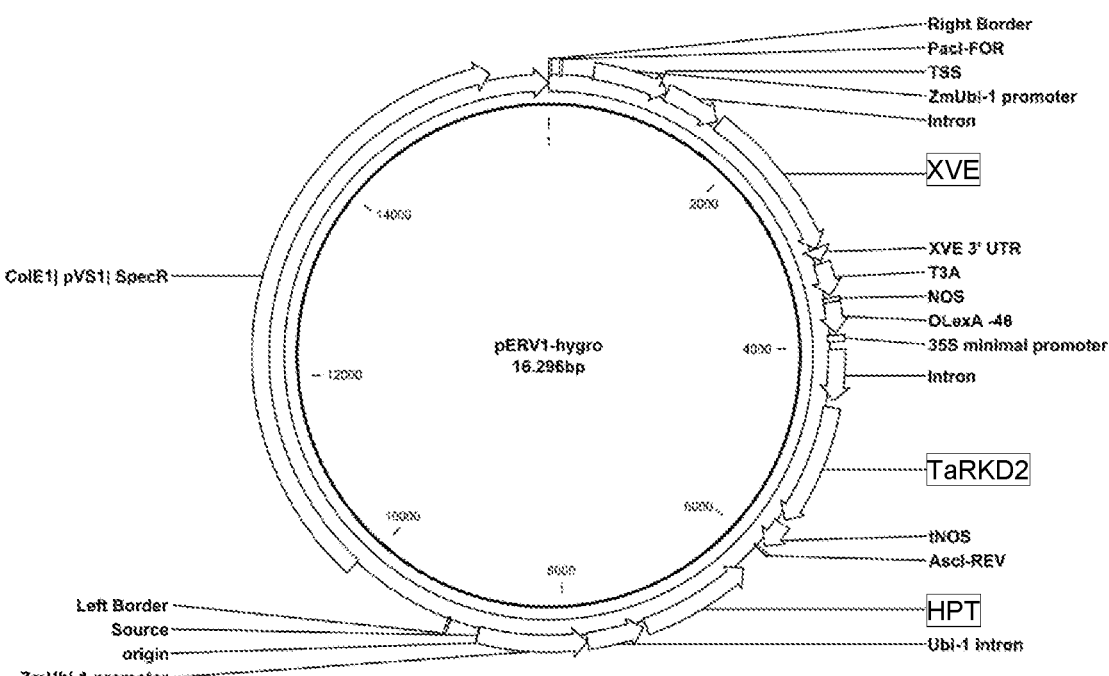
FIG. 8 shows a plasmid map of pERV1-hygro carrying a XVE/OLexA system for chemical β-estradiol inducibility (Borghi, L. (2010). Inducible gene expression systems for plants. In Plant Developmental Biology (pp. 65-75). Humana Press, Totowa, NJ.) of expression of developmental gene of interest.

The benefits of RKD4 (from *Arabidopsis thaliana*) and RKD2 (from *Triticum aestivum* (SEQ ID NO: 4)) expression could be demonstrated in *Zea mays* callus. The two sequences were cloned into the construct described in Example 1 and co-bombarded with the red fluorescent tdTomato gene (DNA: SEQ ID NO: 18; amino acid: SEQ ID NO: 19) under a constitutive promoter (e.g., double 35S promoter (SEQ ID NO: 21) and Ubiquitin intron (SEQ ID NO: 20)). Upon exposure to dexamethasone, the induction of embryogenesis was measured in terms of formation of massive callus structures with stable tdTomato integration. Callus structures showing red fluorescence can be observed after 33 days (FIG. 7, AtRKD4 in the left panels, TaRKD2 in the right panels). The structures were derived from a single cell being hit by the two constructs, leading to embryogenesis and expression of the red fluorescent marker.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for genetic modification in a maize plant cell, the method comprising:
   (a) introducing into the maize plant cell
      (i) a nucleic acid comprising a polynucleotide sequence encoding a RKD2 polypeptide and a RKD4 polypeptide, a recombinant gene comprising the nucleic acid, or a DNA construct comprising the nucleic acid; and
      (ii) a transgene of interest and/or a genome engineering component;
   (b) optionally, cultivating the maize plant cell under conditions allowing the synthesis of the RKD2 polypeptide or the RKD4 polypeptide from the nucleic acid after chemical induction; and
   (c) optionally, cultivating the maize plant cell under conditions allowing the genetic modification of the genome of said maize plant cell by integration of the transgene of interest and activity of the genome engineering component in the presence of the RKD2 polypeptide and the RKD4 polypeptide;
   wherein the polynucleotide sequence encoding the RKD2 polypeptide and the RKD4 polypeptide is operably linked to a heterologous promoter, which is either directly chemically inducible or indirectly chemically inducible,
   wherein the nucleic acid encoding the RKD2 polypeptide and the RKD4 polypeptide comprises a nucleic acid having a coding sequence selected from the group consisting of a nucleic acid comprising the nucleotide sequence of SEQ ID NO: 3 or 4, a nucleic acid comprising a nucleotide sequence at least 95% identity to SEQ ID NO: 3 or 4 over a full length of the nucleic acid, a nucleic acid comprising the nucleotide sequence of SEQ ID NO: 1, and a nucleic acid comprising a nucleotide sequence at least 95% identity to SEQ ID NO: 1 over a full length of the nucleic acid.

2. The method of claim 1, wherein the method improves the efficiency of plant regeneration.

3. The method of claim 1, wherein the method increases the regeneration ability of the plant cell.

4. The method of claim 1, wherein in step (b) the RKD2 polypeptide or the RKD4 polypeptide is synthesized from the nucleic acid upon direct or indirect chemical induction of the heterologous promoter.

5. The method of claim 1, wherein the heterologous promoter is the XVE/OLexA system for chemical β-estradiol inducibility.

6. The method of claim 5, wherein the XVE/OLexA system comprises the nucleic acid sequence of SEQ ID NO: 22, or a nucleic acid sequence at least 95% identical to SEQ ID NO: 22.

7. The method of claim 1, wherein the heterologous promoter is an inducible bidirectional promoter.

8. The method of claim 7, wherein the inducible bidirectional promoter is operably linked to a second nucleic acid sequence encoding a desired polypeptide.

9. The method of claim 8, wherein the second nucleic acid sequence comprises a reporter gene and a polynucleotide encoding a reporter protein.

10. The method of claim 9, wherein the reporter is GUS or tdTomato.

11. The method of claim 7, wherein the inducible bidirectional promoter is a dexamethasone inducible promoter.

12. The method of claim 11, wherein the promoter is pOp1, pOp2, pOp4 or pOp6.

13. The method of claim 12, wherein the pOp6 comprises the nucleic acid sequence of SEQ ID NO: 15, or a nucleic acid sequence at least 95% identical to SEQ ID NO: 15.

14. The method of claim 12, wherein in step (a) (i) a further a nucleic acid comprising a polynucleotide sequence encoding a transcription factor operably linked to a strong constitutive promoter is introduced into the plant cell, wherein the transcription factor activates pOp6 upon binding to dexamethasone.

15. The method of claim 14, wherein the transcription factor is LhGR or LhG4.

16. The method of claim 15, wherein the LhGR has the amino acid sequence of SEQ ID NO: 17, or an amino acid sequence at least 95% identical to SEQ ID NO: 17; or wherein the nucleic acid encoding LhGR comprises the coding sequence of SEQ ID NO: 16, or a coding sequence at least 95% identical to SEQ ID NO: 16.

17. The method of claim 14, wherein the strong constitutive promoter is a ubiquitin promoter or a double 35S promoter.

18. The method of claim 17, wherein the double 35S promoter comprises the nucleotide sequence of SEQ ID NO: 21, or a nucleotide sequence at least 95% identical to SEQ ID NO: 21.

19. The method of claim 17, wherein the ubiquitin promoter comprises the nucleotide sequence of SEQ ID NO: 23, or a nucleotide sequence at least 95% identical to SEQ ID NO: 23.

20. The method of claim 19, wherein the ubiquitin promoter comprises additionally a ubiquitin intron comprising the nucleotide sequence of SEQ ID NO: 20, or a nucleotide sequence at least 95% identical to SEQ ID NO: 20.

21. The method of claim 1, wherein the maize plant cell is cultivated under conditions allowing the genetic modification of the genome of said maize plant cell by integration of the transgene of interest and activity of the genome engineering component in the presence of the RKD2 polypeptide and the RKD4 polypeptide.

22. The method of claim 21, wherein the cultivated maize plant cell does not express a reporter gene in the absence of a chemical agent which induces the chemically-inducible promoter.

23. The method of claim 21, wherein the maize plant cell is cultivated to yield an embryonic structure.

24. The method of claim 23, wherein the embryonic structure is cultivated to yield a regenerated maize plant.

25. The method of claim 1, wherein the RKD2 polypeptide and the RKD4 polypeptide is transiently present, transiently active and/or transiently expressed in the maize plant cell.

26. The method of claim 1, wherein the genome engineering component comprises a) an enzyme inducing a double-stranded break (DSB) or a nucleic acid encoding same, and optionally a repair nucleic acid molecule, wherein the DSB-inducing enzyme recognizes a predetermined site in the genome of said cell;

b) an enzyme inducing a single-stranded break (SSB) or a nucleic acid encoding same, and optionally a repair nucleic acid molecule, wherein the SSB-inducing enzyme recognizes a predetermined site in the genome of said cell;

c) a base editor enzyme, optionally fused to a disarmed DSB- or SSB-inducing enzyme, wherein the base editor enzyme recognizes a predetermined site in the genome of said cell; or d) an enzyme effecting DNA methylation, histone acetylation, histone methylation, histone ubiquitination, histone phosphorylation, histone ribosylation or histone citrullination, optionally fused to a disarmed DSB- or SSB-inducing enzyme, wherein the enzyme recognizes a predetermined site in the genome of said cell.

27. The method of claim 1, wherein the genome engineering component is a CRISPR/Cas endonuclease, a CRISPR/Cas9 endonuclease, a CRISPR/Cpf1 endonuclease, a CRISPR/Csm1 endonuclease, a CRISPR/MAD7 endonuclease, a CRISPR/CasX endonuclease, a CRISPR/CasY endonuclease, a zinc finger nuclease (ZFN), a homing endonuclease, a meganuclease, or a TAL effector nuclease.

28. The method of claim 1, wherein the activity of the genome engineering component in step (c) comprises inducing one or more double-stranded breaks in the genome of the maize plant cell, one or more single strand breaks in the genome of the maize plant cell, one or more base editing events in the genome of the maize plant cell, or one or more of DNA methylation, histone acetylation, histone methylation, histone ubiquitination, histone phosphorylation, histone sumoylation, histone ribosylation or histone citrullination in the genome of the maize plant cell.

29. The method of claim 28, wherein the induction of one or more double-stranded breaks or one or more single strand breaks is followed by non-homologous end joining (NHEJ) and/or by homology directed repair of the break(s) through a homologous recombination mechanism (HDR).

30. The method of claim 1, wherein the transgene in step (a) (ii) is selected from the group consisting of a gene encoding resistance or tolerance to abiotic stress, a gene encoding herbicide resistance, a gene encoding resistance or tolerance to biotic stress, and a gene encoding a yield related trait.

31. The method of claim 1, wherein in step (c) the modification of said genome is selected from i) a replacement of at least one nucleotide;

ii) a deletion of at least one nucleotide;

iii) an insertion of at least one nucleotide;

iv) a change of the DNA methylation;

v) a change in histone acetylation, histone methylation, histone ubiquitination, histone phosphorylation, histone sumoylation, histone ribosylation or histone citrullination; and vi) any combination of i)-v).

32. The method of claim 1, wherein the method promotes maize cell proliferation or maize cell regeneration.

33. The method of claim 1, wherein the method induces embryogenesis from a single maize cell.

34. The method of claim 1, wherein the method increases the stable transformation efficiency of the transgene into the maize plant cell.

35. The method of claim 1, wherein the method increases the efficiency of the genome engineering component to edit the genome of the maize plant cell.

36. A maize plant cell comprising a) a polynucleotide encoding a RKD2 polypeptide and a polynucleotide encoding a RKD4 polypeptide; and b) a transgene of interest and/or a genome engineering component;

wherein the polynucleotide encoding the RKD2 polypeptide or the RKD4 polypeptide is operably linked to a heterologous promoter, which is either directly chemically inducible or indirectly chemically inducible, and wherein the nucleic acid encoding the RKD2 polypeptide and the RKD4 polypeptide comprises a nucleic acid having a coding sequence selected from the group consisting of a nucleic acid comprising the nucleotide sequence of SEQ ID NO: 3 or 4, a nucleic acid comprising a nucleotide sequence at least 95% identity to SEQ ID NO: 3 or 4 over a full length of the nucleic acid, a nucleic acid comprising the nucleotide sequence of SEQ ID NO: 1, and a nucleic acid comprising a nucleotide sequence at least 95% identity to SEQ ID NO: 1 over a full length of the nucleic acid.

37. A maize plant cell comprising a DNA construct, wherein the DNA construct comprises a) a nucleic acid comprising a polynucleotide encoding a RKD2 and a RKD4 polypeptide operably linked to a chemically inducible bidirectional promoter, b) a reporter gene operably linked to the bidirectional promoter, and c) a third recombinant gene encoding a transcription factor operably linked to a strong constitutive promoter, wherein the nucleic acid encoding the RKD2 polypeptide and the RKD4 polypeptide comprises a nucleic acid having a coding sequence selected from the group consisting of a nucleic acid comprising the nucleotide sequence of SEQ ID NO: 3 or 4, a nucleic acid comprising a nucleotide sequence at least 95% identity to SEQ ID NO: 3 or 4 over a full length of the nucleic acid, a nucleic acid comprising the nucleotide sequence of SEQ ID NO: 1, and a nucleic acid comprising a nucleotide sequence at least 95% identity to SEQ ID NO: 1 over a full length of the nucleic acid.

38. A method for producing a genetically modified maize plant, comprising the steps:

(a) genetically modifying the maize plant cell according to the method of claim 1, and (b) regenerating a maize plant from the modified maize plant cell of step (a).

39. The method of claim 38, wherein the produced maize plant does not contain any of the genome engineering components stably integrated into the genome of the maize plant.

40. A method of using a nucleic acid comprising a polynucleotide encoding a RKD2 polypeptide and a RKD4 polypeptide, a recombinant gene comprising the nucleic acid, a DNA construct comprising the nucleic acid for improving the efficiency of maize plant regeneration or increasing the regeneration ability of a maize plant cell upon chemical induction, the method comprising:

(a) introducing into the maize plant cell (i) a nucleic acid comprising a polynucleotide sequence encoding the RKD2 polypeptide and the RKD4 polypeptide, a recombinant gene comprising the nucleic acid, or a DNA construct comprising the nucleic acid; and (ii) a transgene of interest and/or a genome engineering component;

(b) optionally, cultivating the maize plant cell under conditions allowing the synthesis of the RKD2 polypeptide or the RKD4 polypeptide from the nucleic acid after chemical induction; and (c) optionally, cultivating the maize plant cell under conditions allowing the genetic modification of the genome of said maize plant cell by integration of the transgene of interest and activity of the genome engineering component in the presence of the RKD2 polypeptide and the RKD4 polypeptide;

wherein the polynucleotide sequence encoding the RKD2 polypeptide and the RKD4 polypeptide is operably linked to a heterologous promoter, which is either directly chemically inducible or indirectly chemically inducible, wherein the nucleic acid encoding the RKD2 polypeptide and the RKD4 polypeptide comprises a nucleic acid having a coding sequence selected from the group consisting of a nucleic acid comprising the nucleotide sequence of SEQ ID NO: 3 or 4, a nucleic acid comprising a nucleotide sequence at least 95% identity to SEQ ID NO: 3 or 4 over a full length of the nucleic acid, a nucleic acid comprising the nucleotide sequence of SEQ ID NO: 1, and a nucleic acid comprising a nucleotide sequence at least 95% identity to SEQ ID NO: 1 over a full length of the nucleic acid.

* * * * *

SEQUENCE LISTING

<160> NUMBER OF SEQ ID NOS: 23

<210> SEQ ID NO 1
<211> LENGTH: 771
<212> TYPE: DNA
<213> ORGANISM: Artificial Sequence
<220> FEATURE:
<223> OTHER INFORMATION: cDNA of AtRKD4 encoding SEQ ID NO: 2

<400> SEQUENCE: 1

```
atgagttcgt caaaacattc ctctgttttt aactattctg ctctgtttct atcactgttt     60
cttcaacaaa tggatcagaa ctctcttcat catctcgatt ctccaaaaat cgaaaacgag    120
tatgaaccag attcgttata cgacatgtta gataagttgc ctccgcttga ttctctccta    180
gatatggaag atttgaaacc aaatgcaggg ttgcactttc agttccatta caatagcttt    240
gaagatttct tcgaaaacat tgaagtggat aacacaattc catctgatat tcacttgttg    300
acacaagagc cctacttctc aagtgactcc tcttcctctt caccattggc tatccaaaac    360
gacggtctca tttccaacgt gaaagttgaa aaggtaacag ttaagaagaa gaggaacctt    420
aagaaaaaga ggcaagacaa attggagatg tctgagatca aacaattttt cgataggccg    480
atcatgaaag cggctaaaga actgaacgtg ggactcactg tgttgaagaa gcgatgcagg    540
gaattaggaa tttaccggtg gcctcaccgg aagctcaaga gtctaaactc tcttataaag    600
aatctcaaga atgttggaat ggaagaggaa gtgaagaact tggaggaaca taggtttctt    660
attgaacaag aacctgatgc agaactcagt gatggaacca agaagctaag gcaagcttgt    720
ttcaaagcca attataagag aagaaaatca cttggtgatg attattattg a             771
```

<210> SEQ ID NO 2
<211> LENGTH: 256
<212> TYPE: PRT
<213> ORGANISM: Arabidopsis thaliana

<400> SEQUENCE: 2

```
Met Ser Ser Ser Lys His Ser Ser Val Phe Asn Tyr Ser Ala Leu Phe
1               5                   10                  15

Leu Ser Leu Phe Leu Gln Gln Met Asp Gln Asn Ser Leu His His Leu
            20                  25                  30

Asp Ser Pro Lys Ile Glu Asn Glu Tyr Glu Pro Asp Ser Leu Tyr Asp
        35                  40                  45

Met Leu Asp Lys Leu Pro Pro Leu Asp Ser Leu Leu Asp Met Glu Asp
    50                  55                  60

Leu Lys Pro Asn Ala Gly Leu His Phe Gln Phe His Tyr Asn Ser Phe
65                  70                  75                  80

Glu Asp Phe Phe Glu Asn Ile Glu Val Asp Asn Thr Ile Pro Ser Asp
                85                  90                  95

Ile His Leu Leu Thr Gln Glu Pro Tyr Phe Ser Ser Asp Ser Ser Ser
            100                 105                 110

Ser Ser Pro Leu Ala Ile Gln Asn Asp Gly Leu Ile Ser Asn Val Lys
        115                 120                 125

Val Glu Lys Val Thr Val Lys Lys Arg Asn Leu Lys Lys Lys Arg
    130                 135                 140

Gln Asp Lys Leu Glu Met Ser Glu Ile Lys Gln Phe Phe Asp Arg Pro
145                 150                 155                 160

Ile Met Lys Ala Ala Lys Glu Leu Asn Val Gly Leu Thr Val Leu Lys
                165                 170                 175
```

-continued

```
Lys Arg Cys Arg Glu Leu Gly Ile Tyr Arg Trp Pro His Arg Lys Leu
        180             185             190

Lys Ser Leu Asn Ser Leu Ile Lys Asn Leu Lys Asn Val Gly Met Glu
    195             200             205

Glu Glu Val Lys Asn Leu Glu Glu His Arg Phe Leu Ile Glu Gln Glu
    210             215             220

Pro Asp Ala Glu Leu Ser Asp Gly Thr Lys Lys Leu Arg Gln Ala Cys
225             230             235             240

Phe Lys Ala Asn Tyr Lys Arg Arg Lys Ser Leu Gly Asp Asp Tyr Tyr
            245             250             255
```

```
<210> SEQ ID NO 3
<211> LENGTH: 1104
<212> TYPE: DNA
<213> ORGANISM: Artificial Sequence
<220> FEATURE:
<223> OTHER INFORMATION: cDNA of TaRKD2 genotype 1 encoding SEQ ID NO: 5

<400> SEQUENCE: 3
atggagatgc aacaacaata cttcgggggg gacggcgatg cggactggtt ccatcaactc      60
gcattgcttc ccccacttcc aatctcatcg tctctccccc cactcccgat gtcagagggc     120
tcatgtctcc ctatggcagc agcagctgca gctgcactcc cccttggcga ttgctcgagc     180
gccctcatga tacgccctga ggaacagatg tcttgccttc caatgaaccc ctctccagcg     240
gtcgtcgacg atgtctactc ttcctacgca ccgaacaatg tcgacgtgtt gccgccattc     300
ccggcaggac ttgacgacgc tctgttgatg gagtcttttt ctgacatcga cctcgaggag     360
tttgctgacg catttggcca caagatcaag acagaacccc tcgacgatgc catggtcccc     420
gcggaccacg acttcgcggc tcaagcccaa caggcctgcc ctgtggtcat catgaatcag     480
caacaactca acgcacccag agacgtgcgc ctgctcattg acccggatga tgatgacagc     540
accgtggtgg ccggggggcta tgaagctgca gcggtggggt gcgccgagca gaaacaggtc     600
aggccagcac cacgtagggt gagaaagagc tcaggcggcg caagaccagc cgcgggagga     660
aagtccctcg atcacatcgg attcgaggaa ctcaggacct atttctatat gccaatcacc     720
aaggcagcga gggaaatgaa cgtggggctg acagtcctga agaagagatg ccgggaactg     780
ggggtggcgc gctggccaca cagaaagatg aagtctctga gaagcctgat cctcaacatt     840
caggagatgg ggaagggcgc aacatctccc gcagccgtgc aggggggaact tgaagcgctt     900 gagaggtatt gcgccattat ggaggagaac ccggctatag agctcaccga gcaaacgaag     960
aagctcaggc aggcttgttt caaagagaat tataagcggc gtagagccgc cgcttctgtt    1020
aatcttctcg atcactgcta taacgatctg gcatctcatg agcagcaaat gcctctccca    1080
caaatgggat tctttggatt ttag                                           1104
```

```
<210> SEQ ID NO 4
<211> LENGTH: 1104
<212> TYPE: DNA
<213> ORGANISM: Artificial Sequence
<220> FEATURE:
<223> OTHER INFORMATION: cDNA of TaRKD2 genotype 2 encoding SEQ ID NO: 5

<400> SEQUENCE: 4
atggagatgc aacagcaata cttcggcggt gatggcgatg ctgactggtt ccaccagctc      60
gccttgctcc cgcctttgcc gatctcttcg tctctgccgc ctctccccat gagcgagggc     120
agctgcttac ccatggccgc cgccgccgcg gcggcgcttc ctcttgggga ttgctcatca     180
```

-continued

```
gctctcatga ttaggccgga agaacagatg agctgcctgc cgatgaaccc ttcgccagct      240
gttgtcgatg atgtgtacag cagctacgcc cccaacaatg tcgacgtcct cccgccgttt      300
cctgcaggtc tcgacgacgc gctgctcatg gagtccttca gcgatatcga cctggaggag      360
ttcgccgacg ccttcggcca caagattaag accgagcctc tcgacgacgc tatggtgccg      420
gcggatcacg atttcgcggc gcaagcgcaa caggcgtgcc cagtggtgat catgaaccag      480
cagcagctga atgcaccacg cgacgtgcgc ctgctcatag atcccgacga cgatgactca      540
actgtcgtcg ccggggggcta tgaggctgcg gccgttgggt gcgctgagca gaagcaggtg      600
aggccggcgc cacgtcgtgt gcgcaagagc agcggtgggg cacgcccagc cgccggtggg      660
aaaagcctcg atcacatagg gtttgaggag ctacgtacgt atttctacat gcctatcacc      720
aaggcggcgc gggagatgaa cgttggtctc accgtgctca gaagcgctg ccgagagctc       780 ggggtcgccc gctggcctca ccggaagatg aagagcctca ggtcactcat cctcaacatc      840
caggagatgg ggaagggcgc aacgtcgccg gcggctgtgc aaggggaact agaggcgctt      900
gagaggtatt gcgccataat ggaggagaac ccggcgatcg agctgactga gcagaccaag      960
aagctgcggc aggcctgctt taaggagaac tacaagagga ggagagcggc ggcctccgtc     1020
aacttgctcg accattgcta caacgacttg gccagtcatg agcagcagat gccattgcca     1080
cagatgggtt tctttgggtt ctaa                                            1104
```

<210> SEQ ID NO 5
<211> LENGTH: 367
<212> TYPE: PRT
<213> ORGANISM: Triticum aestivum

<400> SEQUENCE: 5

```
Met Glu Met Gln Gln Gln Tyr Phe Gly Gly Asp Gly Asp Ala Asp Trp
1               5                   10                  15

Phe His Gln Leu Ala Leu Leu Pro Pro Leu Pro Ile Ser Ser Ser Leu
            20                  25                  30

Pro Pro Leu Pro Met Ser Glu Gly Ser Cys Leu Pro Met Ala Ala Ala
        35                  40                  45

Ala Ala Ala Ala Leu Pro Leu Gly Asp Cys Ser Ser Ala Leu Met Ile
    50                  55                  60

Arg Pro Glu Glu Gln Met Ser Cys Leu Pro Met Asn Pro Ser Pro Ala
65                  70                  75                  80

Val Val Asp Asp Val Tyr Ser Ser Tyr Ala Pro Asn Asn Val Asp Val
                85                  90                  95

Leu Pro Pro Phe Pro Ala Gly Leu Asp Asp Ala Leu Leu Met Glu Ser
            100                 105                 110

Phe Ser Asp Ile Asp Leu Glu Glu Phe Ala Asp Ala Phe Gly His Lys
        115                 120                 125

Ile Lys Thr Glu Pro Leu Asp Asp Ala Met Val Pro Ala Asp His Asp
        130                 135                 140

Phe Ala Ala Gln Ala Gln Gln Ala Cys Pro Val Val Ile Met Asn Gln
145                 150                 155                 160

Gln Gln Leu Asn Ala Pro Arg Asp Val Arg Leu Leu Ile Asp Pro Asp
                165                 170                 175

Asp Asp Asp Ser Thr Val Val Ala Gly Gly Tyr Glu Ala Ala Ala Val
            180                 185                 190

Gly Cys Ala Glu Gln Lys Gln Val Arg Pro Ala Pro Arg Arg Val Arg
        195                 200                 205
```

-continued

```
Lys Ser Ser Gly Gly Ala Arg Pro Ala Ala Gly Gly Lys Ser Leu Asp
    210                 215                 220

His Ile Gly Phe Glu Glu Leu Arg Thr Tyr Phe Tyr Met Pro Ile Thr
225                 230                 235                 240

Lys Ala Ala Arg Glu Met Asn Val Gly Leu Thr Val Leu Lys Lys Arg
                245                 250                 255

Cys Arg Glu Leu Gly Val Ala Arg Trp Pro His Arg Lys Met Lys Ser
                260                 265                 270

Leu Arg Ser Leu Ile Leu Asn Ile Gln Glu Met Gly Lys Gly Ala Thr
                275                 280                 285

Ser Pro Ala Ala Val Gln Gly Glu Leu Glu Ala Leu Glu Arg Tyr Cys
    290                 295                 300

Ala Ile Met Glu Glu Asn Pro Ala Ile Glu Leu Thr Glu Gln Thr Lys
305                 310                 315                 320

Lys Leu Arg Gln Ala Cys Phe Lys Glu Asn Tyr Lys Arg Arg Arg Ala
                325                 330                 335

Ala Ala Ser Val Asn Leu Leu Asp His Cys Tyr Asn Asp Leu Ala Ser
                340                 345                 350

His Glu Gln Gln Met Pro Leu Pro Gln Met Gly Phe Phe Gly Phe
        355                 360                 365
```

<210> SEQ ID NO 6
<211> LENGTH: 1092
<212> TYPE: DNA
<213> ORGANISM: Artificial Sequence
<220> FEATURE:
<223> OTHER INFORMATION: cDNA of AtLEC2 encoding SEQ ID NO: 7

<400> SEQUENCE: 6

```
atggataact tcttaccctt tccctcttct aacgcaaact ctgtccaaga actctctatg      60
gatcctaaca caatcgctc gcacttcaca acagtcccta cttatgatca tcatcaggct     120
cagcctcatc acttcttgcc tccgtttca tacccggtgg agcagatggc ggcggtgatg     180
aatcctcagc cggtttactt atcggagtgt tatcctcaga tcccggttac gcaaaccgga     240
agtgaattcg gttctctggt tggtaatcct tgtttgtggc aagagagagg tggttttctt     300
gatccgcgta tgacgaagat ggcaaggatc aacaggaaaa acgccatgat gagatcaaga     360
aacaactcta gccctaattc tagtccaagt gagttggttg attcaaagag acagctgatg     420
atgcttaact tgaaaaataa cgtgcagatc tccgacaaga aagatagcta ccaacagtcc     480
acatttgata caagaagct tagggttttg tgtgagaagg aattgaagaa cagcgatgtt     540
gggtcactcg ggaggatagt tctaccaaag agagatgcag aagcaaatct tccgaagcta     600
tctgataaag aaggaatcgt tgtacagatg agagatgttt tctctatgca gtcttggtct     660
ttcaaataca agttttggtc caataacaag agcagaatgt atgtcctcga gaacacagga     720
gaatttgtga gcaaaatgg agctgagata ggagactttt taacaatata cgaggacgaa     780
agcaagaatc tctacttcgc catgaatgga aattcgggaa acaaaatga aggaagagaa     840 aatgagtcga gggaaaggaa ccactacgaa gaggcaatgc ttgattacat accaagagac     900
gaagaggaag cttccattgc aatgctcatc ggaaatctaa acgatcacta tcccatccct     960
aacgatctca tggacctcac cactgacctt cagcaccatc aagccacgtc ctcatcaatg    1020
ccacctgagg atcacgcgta cgtgggttca tccgatgatc aggtgagctt taacgacttt    1080
gagtggtggt ga                                                        1092
```

```
<210> SEQ ID NO 7
<211> LENGTH: 363
<212> TYPE: PRT
<213> ORGANISM: Arabidopsis thaliana

<400> SEQUENCE: 7

Met Asp Asn Phe Leu Pro Phe Pro Ser Ser Asn Ala Asn Ser Val Gln
1               5                   10                  15

Glu Leu Ser Met Asp Pro Asn Asn Asn Arg Ser His Phe Thr Thr Val
            20                  25                  30

Pro Thr Tyr Asp His His Gln Ala Gln Pro His His Phe Leu Pro Pro
        35                  40                  45

Phe Ser Tyr Pro Val Glu Gln Met Ala Ala Val Met Asn Pro Gln Pro
    50                  55                  60

Val Tyr Leu Ser Glu Cys Tyr Pro Gln Ile Pro Val Thr Gln Thr Gly
65                  70                  75                  80

Ser Glu Phe Gly Ser Leu Val Gly Asn Pro Cys Leu Trp Gln Glu Arg
                85                  90                  95

Gly Gly Phe Leu Asp Pro Arg Met Thr Lys Met Ala Arg Ile Asn Arg
            100                 105                 110

Lys Asn Ala Met Met Arg Ser Arg Asn Asn Ser Ser Pro Asn Ser Ser
        115                 120                 125

Pro Ser Glu Leu Val Asp Ser Lys Arg Gln Leu Met Met Leu Asn Leu
    130                 135                 140

Lys Asn Asn Val Gln Ile Ser Asp Lys Lys Asp Ser Tyr Gln Gln Ser
145                 150                 155                 160

Thr Phe Asp Asn Lys Lys Leu Arg Val Leu Cys Glu Lys Glu Leu Lys
                165                 170                 175

Asn Ser Asp Val Gly Ser Leu Gly Arg Ile Val Leu Pro Lys Arg Asp
            180                 185                 190

Ala Glu Ala Asn Leu Pro Lys Leu Ser Asp Lys Glu Gly Ile Val Val
        195                 200                 205

Gln Met Arg Asp Val Phe Ser Met Gln Ser Trp Ser Phe Lys Tyr Lys
    210                 215                 220

Phe Trp Ser Asn Asn Lys Ser Arg Met Tyr Val Leu Glu Asn Thr Gly
225                 230                 235                 240

Glu Phe Val Lys Gln Asn Gly Ala Glu Ile Gly Asp Phe Leu Thr Ile
                245                 250                 255

Tyr Glu Asp Glu Ser Lys Asn Leu Tyr Phe Ala Met Asn Gly Asn Ser
            260                 265                 270

Gly Lys Gln Asn Glu Gly Arg Glu Asn Glu Ser Arg Glu Arg Asn His
        275                 280                 285

Tyr Glu Glu Ala Met Leu Asp Tyr Ile Pro Arg Asp Glu Glu Glu Ala
    290                 295                 300

Ser Ile Ala Met Leu Ile Gly Asn Leu Asn Asp His Tyr Pro Ile Pro
305                 310                 315                 320

Asn Asp Leu Met Asp Leu Thr Thr Asp Leu Gln His His Gln Ala Thr
                325                 330                 335

Ser Ser Ser Met Pro Pro Glu Asp His Ala Tyr Val Gly Ser Ser Asp
            340                 345                 350

Asp Gln Val Ser Phe Asn Asp Phe Glu Trp Trp
        355                 360

<210> SEQ ID NO 8
<211> LENGTH: 879
```

<212> TYPE: DNA
<213> ORGANISM: Artificial Sequence
<220> FEATURE:
<223> OTHER INFORMATION: cDNA of AtWUS encoding SEQ ID NO: 9

<400> SEQUENCE: 8
atggagccgc cacagcatca gcatcatcat catcaagccg accaagaaag cggcaacaac      60
aacaacaaca agtccggctc tggtggttac acgtgtcgcc agaccagcac gaggtggaca     120
ccgacgacgg agcaaatcaa aatcctcaaa gaactttact acaacaatgc aatccggtca     180
ccaacagccg atcagatcca gaagatcact gcaaggctga cagttcgg aaagattgag      240 ggcaagaacg tcttttactg gttccagaac cataaggctc gtgagcgtca agaagagag     300 ttcaacggaa caaacatgac cacaccatct tcatcaccca actcggttat gatggcggct     360
aacgatcatt atcatcctct acttcaccat catcacggtg ttcccatgca gagacctgct     420
aattccgtca acgttaaact taaccaagac catcatctct atcatcataa caagccatat     480
cccagcttca ataacgggaa tttaaatcat gcaagctcag gtactgaatg tggtgttgtt     540
aatgcttcta atggctacat gagtagccat gtctatggat ctatggaaca agactgttct     600
atgaattaca caacgtagg tggaggatgg gcaaacatgg atcatcatta ctcatctgca     660
ccttacaact tcttcgatag agcaaagcct ctgtttggtc tagaaggtca tcaagaagaa     720
gaagaatgtg gtggcgatgc ttatctggaa catcgacgta cgcttcctct cttccctatg     780
cacggtgaag atcacatcaa cggtggtagt ggtgccatct ggaagtatgg ccaatcggaa     840 gttcgcccctt gcgcttctct tgagctacgt ctgaactag                          879

<210> SEQ ID NO 9
<211> LENGTH: 292
<212> TYPE: PRT
<213> ORGANISM: Arabidopsis thaliana

<400> SEQUENCE: 9

Met Glu Pro Pro Gln His Gln His His His Gln Ala Asp Gln Glu
1               5                   10                  15

Ser Gly Asn Asn Asn Asn Asn Lys Ser Gly Ser Gly Gly Tyr Thr Cys
                20                  25                  30

Arg Gln Thr Ser Thr Arg Trp Thr Pro Thr Thr Glu Gln Ile Lys Ile
        35                  40                  45

Leu Lys Glu Leu Tyr Tyr Asn Asn Ala Ile Arg Ser Pro Thr Ala Asp
    50                  55                  60

Gln Ile Gln Lys Ile Thr Ala Arg Leu Arg Gln Phe Gly Lys Ile Glu
65                  70                  75                  80

Gly Lys Asn Val Phe Tyr Trp Phe Gln Asn His Lys Ala Arg Glu Arg
                85                  90                  95

Gln Lys Lys Arg Phe Asn Gly Thr Asn Met Thr Thr Pro Ser Ser Ser
            100                 105                 110

Pro Asn Ser Val Met Met Ala Ala Asn Asp His Tyr His Pro Leu Leu
        115                 120                 125

His His His His Gly Val Pro Met Gln Arg Pro Ala Asn Ser Val Asn
        130                 135                 140

Val Lys Leu Asn Gln Asp His His Leu Tyr His His Asn Lys Pro Tyr
145                 150                 155                 160

Pro Ser Phe Asn Asn Gly Asn Leu Asn His Ala Ser Ser Gly Thr Glu
                165                 170                 175

Cys Gly Val Val Asn Ala Ser Asn Gly Tyr Met Ser Ser His Val Tyr

-continued

```
            180              185              190
Gly Ser Met Glu Gln Asp Cys Ser Met Asn Tyr Asn Asn Val Gly Gly
        195              200              205
Gly Trp Ala Asn Met Asp His His Tyr Ser Ser Ala Pro Tyr Asn Phe
    210              215              220
Phe Asp Arg Ala Lys Pro Leu Phe Gly Leu Glu Gly His Gln Glu Glu
225              230              235              240
Glu Glu Cys Gly Gly Asp Ala Tyr Leu Glu His Arg Arg Thr Leu Pro
            245              250              255
Leu Phe Pro Met His Gly Glu Asp His Ile Asn Gly Gly Ser Gly Ala
        260              265              270
Ile Trp Lys Tyr Gly Gln Ser Glu Val Arg Pro Cys Ala Ser Leu Glu
    275              280              285
Leu Arg Leu Asn
    290
```

<210> SEQ ID NO 10
<211> LENGTH: 1755
<212> TYPE: DNA
<213> ORGANISM: Artificial Sequence
<220> FEATURE:
<223> OTHER INFORMATION: cDNA of AtBBM encoding SEQ ID NO: 11

<400> SEQUENCE: 10

```
atgaactcga tgaataactg gttaggcttc tctctctctc tcatgatca aaatcatcac      60 cgtacggatg ttgactcctc caccaccaga accgccgtag atgttgccgg agggtactgt     120
tttgatctgg ccgctccctc cgatgaatct tctgccgttc aaacatcttt tctttctcct     180
ttcggtgtca ccctcgaagc tttcaccaga gacaataata gtcactcccg agattgggac     240
atcaatggtg gtgcatgcaa taacattaac aataacgaac aaaatggacc aaagcttgag     300
aatttcctcg ccgcaccac cacgatttac aataccaacg agaccgttgt agatggaaat      360
ggcgattgtg gaggaggaga cggtggtggt ggcggctcac taggcctttc gatgataaaa     420
acatggctga gtaatcattc ggttgctaat gctaatcatc aagacaatgg taacggtgca     480
cgaggcttgt ccctctctat gaattcatct actagtgata gcaacaacta caacaacaat     540
gatgatgtcg tccaagagaa gactattgtt gatgtcgtag aaactacacc gaagaaaact     600
attgagagtt ttggacaaag gacgtctata taccgcggtg ttacaaggca tcggtggaca     660
ggtagatacg aggcacattt atgggacaat agttgcaaaa gagaaggcca gactcgcaaa     720
ggaagacaag tttatctggg aggttatgac aaagaagaaa aagcagctag gcttacgat      780 ttagccgcac taaagtattg gggaaccacc actactacta acttcccctt gagtgaatat     840
gagaaagagg tagaagagat gaagcacatg acgaggcaag agtatgttgc ctctctgcgc     900
aggaaaagta gtggtttctc tcgtggtgca tcgatttatc gaggagtaac aaggcatcac     960
caacatggaa ggtggcaagc taggatcgga agagtcgccg gtaacaaaga cctctacttg    1020
ggaactttcg gcacacagga gaggctgct gaggcttatg acattgcagc cattaaattc     1080
agaggattaa gcgcagtgac taacttcgac atgaacagat acaatgttaa agcaatcctc    1140
gagagcccga gtctacctat tggtagttct gcgaaacgtc tcaaggacgt taataatccg    1200
gttccagcta tgatgattag taataacgtt tcagagagtg caaataatgt tagcggttgg    1260
caaaacactg cgtttcagca tcatcaggga atggatttga gcttattgca gcaacagcag    1320
gagaggtacg ttggttatta caatggagga aacttgtcta ccgagagtac tagggtttgt    1380
```

-continued

```
ttcaaacaag aggaggaaca acaacacttc ttgagaaact cgccgagtca catgactaat    1440
gttgatcatc atagctcgac ctctgatgat tctgttaccg tttgtggaaa tgttgttagt    1500
tatggtggtt atcaaggatt cgcaatccct gttggaacat cggttaatta cgatcccttt    1560
actgctgctg agattgctta caacgcaaga aatcattatt actatgctca gcatcagcaa    1620
caacagcaga ttcagcagtc gccgggagga gattttccgg tggcgatttc gaataaccat    1680
agctctaaca tgtactttca cggggaaggt ggtggagaag gggctccaac gttttcagtt    1740
tggaacgaca cttag                                                      1755
```

```
<210> SEQ ID NO 11
<211> LENGTH: 584
<212> TYPE: PRT
<213> ORGANISM: Arabidopsis thaliana

<400> SEQUENCE: 11

Met Asn Ser Met Asn Asn Trp Leu Gly Phe Ser Leu Ser Pro His Asp
1               5                   10                  15

Gln Asn His His Arg Thr Asp Val Asp Ser Ser Thr Thr Arg Thr Ala
            20                  25                  30

Val Asp Val Ala Gly Gly Tyr Cys Phe Asp Leu Ala Ala Pro Ser Asp
        35                  40                  45

Glu Ser Ser Ala Val Gln Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Asn Ile Asn Asn Asn Glu Gln Asn Gly
                85                  90                  95

Pro Lys Leu Glu Asn Phe Leu Gly Arg Thr Thr Thr Ile Tyr Asn Thr
            100                 105                 110

Asn Glu Thr Val Val Asp Gly Asn Gly Asp Cys Gly Gly Gly Asp Gly
            115                 120                 125

Gly Gly Gly Gly Ser Leu Gly Leu Ser Met Ile Lys Thr Trp Leu Ser
        130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asn Asp Asp Val Val Gln Glu Lys Thr Ile Val Asp Val
            180                 185                 190

Val Glu Thr Thr Pro Lys Lys Thr Ile Glu Ser Phe Gly Gln Arg Thr
            195                 200                 205

Ser Ile Tyr Arg Gly Val Thr Arg His Arg Trp Thr Gly Arg Tyr Glu
        210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Thr Thr Thr Thr
            260                 265                 270

Thr Asn Phe Pro Leu Ser Glu Tyr Glu Lys Glu Val Glu Glu Met Lys
            275                 280                 285

His Met Thr Arg Gln Glu Tyr Val Ala Ser Leu Arg Arg Lys Ser Ser
    290                 295                 300
```

```
Gly Phe Ser Arg Gly Ala Ser Ile Tyr Arg Gly Val Thr Arg His His
305             310             315             320

Gln His Gly Arg Trp Gln Ala Arg Ile Gly Arg Val Ala Gly Asn Lys
            325             330             335

Asp Leu Tyr Leu Gly Thr Phe Gly Thr Gln Glu Glu Ala Ala Glu Ala
        340             345             350

Tyr Asp Ile Ala Ala Ile Lys Phe Arg Gly Leu Ser Ala Val Thr Asn
        355             360             365

Phe Asp Met Asn Arg Tyr Asn Val Lys Ala Ile Leu Glu Ser Pro Ser
    370             375             380

Leu Pro Ile Gly Ser Ser Ala Lys Arg Leu Lys Asp Val Asn Asn Pro
385             390             395             400

Val Pro Ala Met Met Ile Ser Asn Asn Val Ser Glu Ser Ala Asn Asn
            405             410             415

Val Ser Gly Trp Gln Asn Thr Ala Phe Gln His His Gln Gly Met Asp
            420             425             430

Leu Ser Leu Leu Gln Gln Gln Gln Glu Arg Tyr Val Gly Tyr Tyr Asn
        435             440             445

Gly Gly Asn Leu Ser Thr Glu Ser Thr Arg Val Cys Phe Lys Gln Glu
    450             455             460

Glu Glu Gln Gln His Phe Leu Arg Asn Ser Pro Ser His Met Thr Asn
465             470             475             480

Val Asp His His Ser Ser Thr Ser Asp Asp Ser Val Thr Val Cys Gly
            485             490             495

Asn Val Val Ser Tyr Gly Gly Tyr Gln Gly Phe Ala Ile Pro Val Gly
            500             505             510

Thr Ser Val Asn Tyr Asp Pro Phe Thr Ala Ala Glu Ile Ala Tyr Asn
        515             520             525

Ala Arg Asn His Tyr Tyr Tyr Ala Gln His Gln Gln Gln Gln Gln Ile
    530             535             540

Gln Gln Ser Pro Gly Gly Asp Phe Pro Val Ala Ile Ser Asn Asn His
545             550             555             560

Ser Ser Asn Met Tyr Phe His Gly Glu Gly Gly Gly Glu Gly Ala Pro
            565             570             575

Thr Phe Ser Val Trp Asn Asp Thr
            580
```

<210> SEQ ID NO 12
<211> LENGTH: 807
<212> TYPE: DNA
<213> ORGANISM: Artificial Sequence
<220> FEATURE:
<223> OTHER INFORMATION: cDNA of AtAGL15 encoding SEQ ID NO: 13

<400> SEQUENCE: 12

```
atgggtcgtg gaaaaatcga gataaagagg atcgagaatg cgaatagcag acaagtcact      60
ttttccaaga ggcgttctgg gttacttaag aaagctcgtg agctctctgt tctttgtgat     120
gctgaagttg ctgtcatcgt cttctctaag tctggcaagc tcttcgagta ctccagtact     180
ggaatgaagc aaacactttc cagatacggt aatcaccaga gttcttcagc ttctaaagca     240
gaggaggatt gtgcagaggt ggatatttta aaggatcaac tttcaaagct tcaagagaaa     300
catttacaac tgcagggcaa gggcttgaat cctctgacct ttaaagagct gcaaagcctt     360
gagcagcaac tatatcatgc attgattact gtcagagagc gaaaggaacg attgctgact     420
aaccaacttg aagaatcacg cctcaaggaa caacgagcag agttggaaaa cgagaccttg     480
```

```
cgtagacagg ttcaagaact gaggagcttt ctcccgtcgt tcacccacta tgttccatcc      540
tacatcaaat gctttgctat agatccaaag aacgctctca taaaccacga cagtaaatgc      600
agcctccaga acaccgattc agacacaact ttgcaattag ggttgccggg agaggcacat      660
gatagaagga cgaatgaagg agaaagagag agcccgtcaa gcgattcagt gacaacaaac      720
acgagcagcg aaactgcaga aagaggggat cagtctagtt tagcaaattc tccacctgaa      780
gccaaaagac aaaggttctc tgtttag                                          807
```

```
<210> SEQ ID NO 13
<211> LENGTH: 268
<212> TYPE: PRT
<213> ORGANISM: Arabidopsis thaliana

<400> SEQUENCE: 13

Met Gly Arg Gly Lys Ile Glu Ile Lys Arg Ile Glu Asn Ala Asn Ser
1               5                   10                  15

Arg Gln Val Thr Phe Ser Lys Arg Arg Ser Gly Leu Leu Lys Lys Ala
            20                  25                  30

Arg Glu Leu Ser Val Leu Cys Asp Ala Glu Val Ala Val Ile Val Phe
        35                  40                  45

Ser Lys Ser Gly Lys Leu Phe Glu Tyr Ser Ser Thr Gly Met Lys Gln
    50                  55                  60

Thr Leu Ser Arg Tyr Gly Asn His Gln Ser Ser Ser Ala Ser Lys Ala
65                  70                  75                  80

Glu Glu Asp Cys Ala Glu Val Asp Ile Leu Lys Asp Gln Leu Ser Lys
                85                  90                  95

Leu Gln Glu Lys His Leu Gln Leu Gln Gly Lys Gly Leu Asn Pro Leu
            100                 105                 110

Thr Phe Lys Glu Leu Gln Ser Leu Glu Gln Gln Leu Tyr His Ala Leu
        115                 120                 125

Ile Thr Val Arg Glu Arg Lys Glu Arg Leu Leu Thr Asn Gln Leu Glu
        130                 135                 140

Glu Ser Arg Leu Lys Glu Gln Arg Ala Glu Leu Glu Asn Glu Thr Leu
145                 150                 155                 160

Arg Arg Gln Val Gln Glu Leu Arg Ser Phe Leu Pro Ser Phe Thr His
            165                 170                 175

Tyr Val Pro Ser Tyr Ile Lys Cys Phe Ala Ile Asp Pro Lys Asn Ala
            180                 185                 190

Leu Ile Asn His Asp Ser Lys Cys Ser Leu Gln Asn Thr Asp Ser Asp
        195                 200                 205

Thr Thr Leu Gln Leu Gly Leu Pro Gly Glu Ala His Asp Arg Arg Thr
    210                 215                 220

Asn Glu Gly Glu Arg Glu Ser Pro Ser Ser Asp Ser Val Thr Thr Asn
225                 230                 235                 240

Thr Ser Ser Glu Thr Ala Glu Arg Gly Asp Gln Ser Ser Leu Ala Asn
                245                 250                 255

Ser Pro Pro Glu Ala Lys Arg Gln Arg Phe Ser Val
            260                 265
```

```
<210> SEQ ID NO 14
<211> LENGTH: 16296
<212> TYPE: DNA
<213> ORGANISM: Artificial Sequence
<220> FEATURE:
<223> OTHER INFORMATION: plasmid pERV1-hygro carrying TaRKD2 as CDS
```

-continued

<400> SEQUENCE: 14

```
ggtttacccg ccaatatatc ctgtcaaaca ctgatagttt aaaccgaagg cgggaaacga      60
caatctgatc gggtaccggg cccaagatct ggcccttaag gccttactag gctgcagtgc     120
agcgtgaccc ggtcgtgccc ctctctagag ataatgagca ttgcatgtct aagttataaa     180
aaattaccac atattttttt tgtcacactt gtttgaagtg cagtttatct atctttatac     240
atatatttaa actttactct acgaataata taatctatag tactacaata atatcagtgt     300
tttagagaat catataaatg aacagttaga catggtctaa aggacaattg agtattttga     360
caacaggact ctacagtttt atctttttag tgtgcatgtg ttctcctttt tttttgcaaa     420
tagcttcacc tatataatac ttcatccatt ttattagtac atccatttag ggtttagggt     480
taatggtttt tatagactaa ttttttttagt acatctattt tattctattt tagcctctaa     540
attaagaaaa ctaaaactct attttagttt ttttatttaa taatttagat ataaaataga     600
ataaaataaa gtgactaaaa attaaacaaa tacccttttaa gaaattaaaa aaactaagga     660
aacatttttc ttgtttcgag tagataatgc cagcctgtta aacgccgtcg atcgacgagt     720
ctaacggaca ccaaccagcg aaccagcagc gtcgcgtcgg gccaagcgaa gcagacggca     780
cggcatctct gtcgctgcct ctggacccct ctcgagagtt ccgctccacc gttggacttg     840
ctccgctgtc ggcatccaga aattgcgtgg cggagcggca gacgtgagcc ggcacggcag     900
gcggcctcct cctcctctca cggcaccggc agctacgggg gattcctttc ccaccgctcc     960
ttcgctttcc cttcctcgcc cgccgtaata aatagacacc ccctccacac cctctttccc    1020
caacctcgtg ttgttcggag cgcacacaca cacaaccaga tctcccccaa atccacccgt    1080
cggcacctcc gcttcaaggt acgccgctcg tcctccccccc ccccccctct ctaccttctc    1140
tagatcggcg ttccggtcca tggttagggc ccggtagttc tacttctgtt catgtttgtg    1200
ttagatccgt gtttgtgtta gatccgtgct gctagcgttc gtacacggat gcgacctgta    1260
cgtcagacac gttctgattg ctaacttgcc agtgtttctc tttggggaat cctgggatgg    1320
ctctagccgt tccgcagacg ggatcgatct aggataggta tacatgttga tgtgggtttt    1380
actgatgcat atacatgatg gcatatgcag catctattca tatgctctaa ccttgagtac    1440
ctatctatta taataaacaa gtatgtttta taattatttt gatcttgata tacttggatg    1500
atggcatatg cagcagctat atgtggattt ttttagccct gccttcatac gctatttatt    1560
tgcttggtac tgtttctttt gtcgatgctc accctgttgt ttggtgttac ttctgcaggt    1620
actagtattc cgggcggaat gaaagcgtta acggccaggc aacaagaggt gtttgatctc    1680
atccgtgatc acatcagcca gacaggtatg ccgccgacgc gtgcggaaat cgcgcagcgt    1740
ttggggttcc gttccccaaa cgcggctgaa gaacatctga aggcgctggc acgcaaaggc    1800
gttattgaaa ttgtttccgg cgcatcacgc gggattcgtc tgttgcagga agaggaagaa    1860
gggttgccgc tggtaggtcg tgtggctgcc ggtgaaccgt cgagcgcccc cccgaccgat    1920
gtcagcctgg gggacgagct ccacttagac ggcgaggacg tggcgatggc gcatgccgac    1980
gcgctagacg atttcgatct ggacatgttg ggggacgggg attccccggg tccgggattt    2040
accccccacg actccgcccc ctacggcgct ctggatatgg ccgacttcga gtttgagcag    2100
atgtttaccg atgcccttgg aattgacgag tacggtgggg atccgtctgc tggagacatg    2160
agagctgcca acctttggcc aagcccgctc atgatcaaac gctctaagaa gaacagcctg    2220
gccttgtccc tgacggccga ccagatggtc agtgccttgt tggatgctga gcccccccata    2280
```

```
ctctattccg agtatgatcc taccagaccc ttcagtgaag cttcgatgat gggcttactg   2340
accaacctgg cagacaggga gctggttcac atgatcaact gggcgaagag ggtgccaggc   2400
tttgtggatt tgaccctcca tgatcaggtc caccttctag aatgtgcctg gctagagatc   2460
ctgatgattg tgtctcgtctg gcgctccatg gagcacccag ggaagctact gtttgctcct   2520
aacttgctct tggacaggaa ccagggaaaa tgtgtagagg gcatggtgga gatcttcgac   2580
atgctgctgg ctacatcatc tcggttccgc atgatgaatc tgcagggaga ggagtttgtg   2640
tgcctcaaat ctattatttt gcttaattct ggagtgtaca catttctgtc cagcaccctg   2700
aagtctctgg aagagaagga ccatatccac cgagtcctgg acaagatcac agacactttg   2760
atccacctga tggccaaggc aggcctgacc ctgcagcagc agcaccagcg gctggcccag   2820
ctcctcctca tcctctccca catcaggcac atgagtaaca aaggcatgga gcatctgtac   2880
agcatgaagt gcaagaacgt ggtgcccctc tatgacctgc tgctggagat gctggacgcc   2940
caccgcctac atgcgcccac tagccgtgga ggggcatccg tggaggagac ggaccaaagc   3000
cacttggcca ctgcgggctc tacttcatcg cattccttgc aaaagtatta catcacgggg   3060
gaggcagagg gtttccctgc cacagtctga gagctccctg gcggaattcc cagagatgtt   3120
agctgaaatc atcactaatc agataccaaa atattcaaat ggaaatatca aaaagcttct   3180
gtttcatcaa aaatgactcg acctaactga gtaagctagc ttgttcgagt attatggcat   3240
tgggaaaact gttttttcttg taccatttgt tgtgcttgta atttactgtg ttttttattc   3300
ggttttcgct atcgaactgt gaaatggaaa tggatggaga agagttaatg aatgatatgg   3360
tccttttgtt cattctcaaa ttaatattat ttgtttttc tcttatttgt tgtgtgttga   3420
atttgaaatt ataagagata tgcaaacatt ttgttttgag taaaaatgtg tcaaatcgtg   3480
gcctctaatg accgaagtta atatgaggag taaaacacta gatccccaaa caagcttgga   3540
aactgaaggc gctcgagtta ctagatcggg gaattgatcc cccctcgaca gcttgcatgc   3600
cgcttgggct gcaggtcgag gctaaaaaac taatcgcatt atcatcccct cgacgtactg   3660
tacatataac cactggtttt atatacagca gtactgtaca tataaccact ggtttttatat   3720 acagcagtcg acgtactgta catataacca ctggtttttat atacagcagt actgtacata   3780
taaccactgg ttttatatac agcagtcgag gtaagattag atatggatat gtatatggat   3840
atgtatatgg tggtaatgcc atgtaatatg ctcgactcta ggatcttcgc aagacccttc   3900
ctctatataa ggaagttcat ttcatttgga gaggacacgc tgaagctagt cgactctagc   3960
ctccctaggc tgccggacga cgagctcctc cccctccc ctccgccgcc gccgcgccgg   4020
taaccacccc gccctctcc tctttctttc tccgttttt tttccgtctc ggtctcgatc   4080
tttggccttg gtagtttggg tgggcgagag gcggcttcgt gcgcgcccag atcggtcgc   4140 gggagggggcg ggatctcgcg gctggggctc tcgccggcgt ggatccggcc cggatctcgc   4200
ggggaatggg gctctcggat gtagatctgc gatccgccgt tgttgggggga gatgatgggg   4260 ggtttaaaat ttccgccatg ctaaacaaga tcaggaagag gggaaaaggg cactatggtt   4320 tatatttta tatatttctg ctgcttcgtc aggcttagat gtgctagatc ttcttctttc   4380
tttcttcttt ttgtgggtag aatttgaatc cctcagcatt gttcatcggt agttttttctt   4440 ttcatgattt gtgacaaatg cagcctcgtg cggagctttt ttgtaggcgc gggctgcagg   4500
aattcaagct tacgcgtgtc atcacaagtt tgtacaaaaa agcaggctat ggagatgcaa   4560
caacaatact tcggggggga cggcgatgcg gactggttcc atcaactcgc attgcttccc   4620
ccacttccaa tctcatcgtc tctcccccca ctcccgatgt cagagggctc atgtctccct   4680
```

-continued

```
atggcagcag cagctgcagc tgcactcccc cttggcgatt gctcgagcgc cctcatgata   4740
cgccctgagg aacagatgtc ttgccttcca atgaacccct ctccagcggt cgtcgacgat   4800
gtctactctt cctacgcacc gaacaatgtc gacgtgttgc cgccattccc ggcaggactt   4860
gacgacgctc tgttgatgga gtctttttct gacatcgacc tcgaggagtt tgctgacgca   4920
tttggccaca agatcaagac agaacccctc gacgatgcca tggtccccgc ggaccacgac   4980
ttcgcggctc aagcccaaca ggcctgccct gtggtcatca tgaatcagca acaactcaac   5040
gcacccagag acgtgcgcct gctcattgac ccggatgatg atgacagcac cgtggtggcc   5100
gggggctatg aagctgcagc ggtggggtgc gccgagcaga aacaggtcag gccagcacca   5160
cgtagggtga aaagagctc aggcggcgca agaccagccg cgggaggaaa gtccctcgat   5220
cacatcggat tcgaggaact caggacctat ttctatatgc caatcaccaa ggcagcgagg   5280
gaaatgaacg tggggctgac agtcctgaag aagagatgcc gggaactggg ggtggcgcgc   5340
tggccacaca gaaagatgaa gtctctgaga agcctgatcc tcaacattca ggagatgggg   5400
aagggcgcaa catctcccgc agccgtgcag ggggaacttg aagcgcttga gaggtattgc   5460
gccattatgg aggagaaccc ggctatagag ctcaccgagc aaacgaagaa gctcaggcag   5520
gcttgtttca aagagaatta taagcggcgt agagccgccg cttctgttaa tcttctcgat   5580
cactgctata cgatctggc atctcatgag cagcaaatgc ctctcccaca aatgggattc   5640
tttggatttt agacccagct ttcttgtaca aagtggtgat gactcgaatt tccccgatcg   5700
ttcaaacatt tggcaataaa gtttcttaag attgaatcct gttgccggtc ttgcgatgat   5760
tatcatataa tttctgttga attacgttaa gcatgtaata attaacatgt aatgcatgac   5820
gttatttatg agatgggttt ttatgattag agtcccgcaa ttatacattt aatacgcgat   5880
agaaaacaaa atatagcgcg caaactagga taaattatcg cgcgcggtgt catctatgtt   5940
actagatcgc tcgacgcggc cgccatggcc tctagtggat cagcttgcat gcctgcaggt   6000
cactggattt tggttttagg aattagaaat tttattgata gaagtatttt acaaatacaa   6060
atacatacta agggtttctt atatgctcaa cacatgagcg aaaccctata agaaccctaa   6120
ttcccttatc tgggaactac tcacacatta ttctggagaa aaatagagag agatagattt   6180
gtagagagag actggtgatt tttgcggact ccggtcggca tctactctat tcctttgccc   6240
tcggacgagt gctggggcgt cggtttccac tatcggcgag tacttctaca cagccatcgg   6300
tccagacggc cgcgcttctg cgggcgattt gtgtacgccc gacagtcccg ctccggatc   6360 ggacgattgc gtcgcatcga ccctgcgccc aagctgcatc atcgaaattg ccgtcaacca   6420
agctctgata gagttggtca agaccaatgc ggagcatata cgcccggagc cgcggcgatc   6480
ctgcaagctc cggatgcctc cgctcgaagt agcgcgtctg ctgctccata caagccaacc   6540
acggcctcca gaagaagatg ttggcgacct cgtattggga atccccgaac atcgcctcgc   6600
tccagtcaat gaccgctgtt atgcggccat tgtccgtcag gacattgttg gagccgaaat   6660
ccgcgtgcac gaggtgccgg acttcggggc agtcctcggc ccaaagcatc agctcatcga   6720
gagcctgcgc gacggacgca ctgacggtgt cgtccatcac agtttgccag tgatacacat   6780
ggggatcagc aatcgcgcat atgaaatcac gccatgtagt gtattgaccg attccttgcg   6840
gtccgaatgg gccgaacccg ctcgtctggc taagatcggc cgcagcgatc gcatccatgg   6900
cctccgcgac cggctgcaga acagcgggca gttcggtttc aggcaggtct tgcaacgtga   6960 cacccctgtgc acggcgggag atgcaatagg tcaggctctc gctgaattcc ccaatgtcaa   7020
```

-continued

```
gcacttccgg aatcgggagc gcggccgatg caaagtgccg ataaacataa cgatctttgt    7080
agaaaccatc ggcgcagcta tttacccgca ggacatatcc acgccctcct acatcgaagc    7140
tgaaagcacg agattcttcg ccctccgaga gctgcatcag gtcggagacg ctgtcgaact    7200
tttcgatcag aaacttctcg acagacgtcg cggtgagttc aggctttttc atatcttatt    7260
gcccccgggg gccctcgacc tgcagaagta acaccaaaca acagggtgag catcgacaaa    7320
agaaacagta ccaagcaaat aaatagcgta tgaaggcagg gctaaaaaaa tccacatata    7380
gctgctgcat atgccatcat ccaagtatat caagatcaaa ataattataa aacatacttg    7440
tttattataa tagataggta ctcaaggtta gagcatatga atagatgctg catatgccat    7500
catgtatatg catcagtaaa acccacatca acatgtatac ctatcctaga tcgatcccgt    7560
ctgcggaacg gctagagcca tcccaggatt ccccaaagag aaacactggc aagttagcaa    7620
tcagaacgtg tctgacgtac aggtcgcatc cgtgtacgaa cgctagcagc acggatctaa    7680
cacaaacacg gatctaacac aaacatgaac agaagtagaa ctaccgggcc ctaaccatgg    7740
accggaacgc cgatctagag aaggtagaga ggggggggg gggaggacga gcggcgtacc    7800
ttgaagcgga ggtgccgacg ggtggatttg ggggagatct ggttgtgtgt gtgtgcgctc    7860
cgaacaacac gaggttgggg aaagagggtg tggaggggt gtctatttat tacggcgggc    7920
gaggaaggga aagcgaagga gcggtgggaa aggaatcccc cgtagctgcc ggtgccgtga    7980
gaggaggagg aggccgcctg ccgtgccggc tcacgtctgc cgctccgcca cgcaatttct    8040
ggatgccgac agcggagcaa gtccaacggt ggagcggaac tctcgagagg ggtccagagg    8100
cagcgacaga gatgccgtgc cgtctgcttc gcttggcccg acgcgacgct gctggttcgc    8160
tggttggtgt ccgttagact cgtcgatcga cggcgtttaa caggctggca ttatctactc    8220
gaaacaagaa aaatgtttcc ttagtttttt taatttctta aagggtattt gtttaatttt    8280
tagtcacttt attttattct attttatatc taaattatta aataaaaaaa ctaaaataga    8340
gttttagttt tcttaattta gaggctaaaa tagaataaaa tagatgtact aaaaaaatta    8400
gtctataaaa accattaacc ctaaacccta aatggatgta ctaataaaat ggatgaagta    8460
ttatataggt gaagctattt gcaaaaaaaa aggagaacac atgcacacta aaaagataaa    8520
actgtagagt cctgttgtca aaatactcaa ttgtccttta gaccatgtct aactgttcat    8580
ttatatgatt ctctaaaaca ctgatattat tgtagtacta tagattatat tattcgtaga    8640
gtaaagttta aatatatgta taaagataga taaactgcac ttcaaacaag tgtgacaaaa    8700
aaaatatgtg gtaatttttt ataacttaga catgcaatgc tcattatctc tagagagggg    8760
cacgaccggg tcacgctgca ctgcagacta ctagagccga tcgtgaagtt tctcatctaa    8820
gcccccattt ggacgtgaat gtagacacgt cgaaataaag atttccgaat tagaataatt    8880
tgtttattgc tttcgcctat aaatacgacg gatcgtaatt tgtcgtttta tcaaaatgta    8940
ctttcatttt ataataacgc tgcggacatc tacatttttg aattgaaaaa aaattggtaa    9000
ttactctttc ttttctcca tattgaccat catactcatt gctgatccat gtagatttcc    9060
cggacatgaa gccatttaca attgaatata tcctgccgcc gctgccgctt tgcacccggt    9120
ggagcttgca tgtggtttc tacgcagaac tgagccggtt aggcagataa tttccattga    9180
gaactgagcc atgtgcacct tcccccaac acggtgagcg acggggcaac ggagtgatcc    9240
acatgggact tttaaacatc atccgtcgga tggcgttgcg agagaagcag tcgatccgtg    9300
agatcagccg acgcaccggg caggcgcgca acacgtcgc aaagtatttg aacgcaggta    9360
caatcgagcc gacgttcacg cggaacgacc aagcaagcta tgttgcgatt acttcgccaa    9420
```

-continued

```
ctattgcgat aacaagaaaa agccagcctt tcatgatata tctcccaatt tgtgtagggc    9480
ttattatgca cgcttaaaaa taataaaagc agacttgacc tgatagtttg gctgtgagca    9540
attatgtgct tagtgcatct aacgcttgag ttaagccgcg ccgcgaagcg gcgtcggctt    9600
gaacgaattg ttagacatta tttgccgact accttggtga tctcgccttt cacgtagtgg    9660
acaaattctt ccaactgatc tgcgcgcgag gccaagcgat cttcttcttg tccaagataa    9720
gcctgtctag cttcaagtat gacgggctga tactgggccg gcaggcgctc cattgcccag    9780
tcggcagcga catccttcgg cgcgattttg ccggttactg cgctgtacca aatgcgggac    9840
aacgtaagca ctacatttcg ctcatcgcca gcccagtcgg gcggcgagtt ccatagcgtt    9900
aaggtttcat ttagcgcctc aaatagatcc tgttcaggaa ccggatcaaa gagttcctcc    9960
gccgctggac ctaccaaggc aacgctatgt tctcttgctt ttgtcagcaa gatagccaga   10020
tcaatgtcga tcgtggctgg ctcgaagata cctgcaagaa tgtcattgcg ctgccattct   10080
ccaaattgca gttcgcgctt agctggataa cgccacggaa tgatgtcgtc gtgcacaaca   10140
atggtgactt ctacagcgcg gagaatctcg ctctctccag gggaagccga gtttccaaa    10200 aggtcgttga tcaaagctcg ccgcgttgtt tcatcaagcc ttacggtcac cgtaaccagc   10260
aaatcaatat cactgtgtgg cttcaggccg ccatccactg cggagccgta caaatgtacg   10320
gccagcaacg tcggttcgag atggcgctcg atgacgccaa ctacctctga tagttgagtc   10380
gatacttcgg cgatcaccgc ttccctcatg atgtttaact ttgttttagg gcgactgccc   10440
tgctgcgtaa catcgttgct gctccataac atcaaacatc gacccacggc gtaacgcgct   10500
tgctgcttgg atgcccgagg catagactgt accccaaaaa aacagtcata acaagccatg   10560
aaaaccgcca ctgcgccgtt accaccgctg cgttcggtca aggttctgga ccagttgcgt   10620
gagcgcatac gctacttgca ttacagctta cgaaccgaac aggcttatgt ccactgggtt   10680
cgtgccttca tccgtttcca cggtgtgcgt cacccggcaa ccttgggcag cagcgaagtc   10740
gaggcatttc tgtcctggct ggcgaacgag cgcaaggttt cggtctccac gcatcgtcag   10800
gcatacccac cggtgccttg atgtgggcgc cggcggtcga gtggcgacgg cgcggcttgt   10860
ccgcgccctg gtagattgcc tggccgtagg ccagccattt ttgagcggcc agcggccgcg   10920
ataggccgac gcgaagcggc ggggcgtagg gagcgcagcg accgaagggt aggcgctttt   10980
tgcagctctt cggctgtgcg ctggccagac agttatgcac aggccaggcg ggttttaaga   11040
gttttaataa gttttaaaga gttttaggcg gaaaaatcgc ctttttttctc ttttatatca   11100 gtcacttaca tgtgtgaccg gttcccaatg tacggctttg ggttcccaat gtacgggttc   11160
cggttcccaa tgtacggctt tgggttccca atgtacgtgc tatccacagg aaagagacct   11220
tttcgacctt tttcccctgc tagggcaatt tgccctagca tctgctccgt acattaggaa   11280
ccggcggatg cttcgccctc gatcaggttg cggtagcgca tgactaggat cgggccagcc   11340
tgccccgcct cctccttcaa atcgtactcc ggcaggtcat ttgacccgat cagcttgcgc   11400
acggtgaaac agaacttctt gaactctccg gcgctgccac tgcgttcgta gatcgtcttg   11460
aacaaccatc tggcttctgc cttgcctgcg gcgcggcgtg ccaggcggta gagaaaacgg   11520
ccgatgccgg gatcgatcaa aaagtaatcg gggtgaaccg tcagcacgtc cgggttcttg   11580
ccttctgtga tctcgcggta catccaatca gctagctcga tctcgatgta ctccggccgc   11640
ccggtttcgc tctttacgat cttgtagcgg ctaatcaagg cttcaccctc ggataccgtc   11700
accaggcggc cgttcttggc cttcttcgta cgctgcatgg caacgtgcgt ggtgtttaac   11760
```

-continued

```
cgaatgcagg tttctaccag gtcgtctttc tgctttccgc catcggctcg ccggcagaac   11820
ttgagtacgt ccgcaacgtg tggacggaac acgcggccgg gcttgtctcc cttcccttcc   11880
cggtatcggt tcatggattc ggttagatgg gaaaccgcca tcagtaccag gtcgtaatcc   11940
cacacactcg ccatgccggc cggccctgcg gaaacctcta cgtgcccgtc tggaagctcg   12000
tagcggatca cctcgccagc tcgtcggtca cgcttcgaca gacggaaaac ggccacgtcc   12060
atgatgctgc gactatcgcg ggtgcccacg tcatagagca tcggaacgaa aaaatctggt   12120
tgctcgtcgc ccttgggcgg cttcctaatc gacggcgcac cggctgccgg cggttgccgg   12180
gattctttgc ggattcgatc agcggccgct tgccacgatt caccggggcg tgcttctgcc   12240
tcgatgcgtt gccgctgggc ggcctgcgcc gccttcaact tctccaccag gtcatcaccc   12300
agcgccgcgc cgatttgtac cgggccggat ggtttgcgac cgctcacgcc gattcctcgg   12360
gcttgggggt tccagtgcca ttgcagggcc ggcagacaac ccagccgctt acgcctggcc   12420
aaccgcccgt tcctccacac atggggcatt ccacggcgtc ggtgcctggt tgttcttgat   12480
tttccatgcc gcctccttta gccgctaaaa ttcatctact catttattca tttgctcatt   12540
tactctggta gctgcgcgat gtattcagat agcagctcgg taatggtctt gccttggcgt   12600
accgcgtaca tcttcagctt ggtgtgatcc tccgccggca actgaaagtt gacccgcttc   12660
atggctggcg tgtctgccag gctggccaac gttgcagcct tgctgctgcg tgcgctcgga   12720
cggccggcac ttagcgtgtt tgtgcttttg ctcattttct ctttacctca ttaactcaaa   12780
tgagttttga tttaatttca gcggccagcg cctggacctc gcgggcagcg tcgccctcgg   12840
gttctgattc aagaacggtt gtgccggcgg cggcagtgcc tgggtagctc acgcgctgcg   12900
tgatacggga ctcaagaatg ggcagctcgt acccggccag cgcctcggca acctcaccgc   12960
cgatgcgcgt gcctttgatc gcccgcgaca cgacaaaggc cgcttgtagc cttccatccg   13020
tgacctcaat gcgctgctta accagctcca ccaggtcggc ggtggcccat atgtcgtaag   13080
ggcttggctg caccggaatc agcacgaagt cggctgcctt gatcgcggac acagccaagt   13140
ccgccgcctg gggcgctccg tcgatcacta cgaagtcgcg ccggccgatg gccttcacgt   13200
cgcggtcaat cgtcgggcgg tcgatgccga caacggttag cggttgatct tcccgcacgg   13260
ccgcccaatc gcgggcactg ccctggggat cggaatcgac taacagaaca tcggccccgg   13320
cgagttgcag ggcgcgggct agatgggttg cgatggtcgt cttgcctgac ccgcctttct   13380
ggttaagtac agcgataacc ttcatgcgtt ccccttgcgt atttgtttat ttactcatcg   13440
catcatatac gcagcgaccg catgacgcaa gctgttttac tcaaatacac atcacctttt   13500
tagacggcgg cgctcggttt cttcagcggc caagctcgcc ggccaggccg cgagcttggc   13560
atcagacaaa ccggccagga tttcatgcag ccgcacggtt gagacgtgcg cgggcggctc   13620
gaacacgtac ccggccgcga tcatctccgc ctcgatctct tcggtaatga aaaacggttc   13680
gtcctggccg tcctggtgcg gtttcatgct tgttcctctt ggcgttcatt ctcggcggcc   13740
gccagggcgt cggcctcggt caatgcgtcc tcacggaagg caccgcgccg cctgcctcg   13800 gtgggcgtca cttcctcgct gcgctcaagt gcgcggtaca gggtcgagcg atgcacgcca   13860
agcagtgcag ccgcctcttt cacggtgcgg ccttcctggt cgatcagctc gcgggcgtgc   13920
gcgatctgtg ccggggtgag ggtagggcgg gggccaaact tcacgcctcg cgccttggcg   13980
gcctcgcgcc cgctccgggt gcggtcgatg attaggggaac gctcgaactc ggcaatgccg   14040
gcgaacacgg tcaacaccat gcggccggcc ggcgtggtgg tgtcggccca cggctctgcc   14100
aggctacgca ggcccgcgcc ggcctcctgg atgcgctcgg caatgtccag taggtcgcgg   14160
```

-continued

```
gtgctgcggg ccaggcggtc tagcctggtc actgtcacaa cgtcgccagg gcgtaggtgg    14220
tcaagcatcc tggccagctc cgggcggtcg cgcctggtgc cggtgatctt ctcggaaaac    14280
agcttggtgc agccggccgc gtgcagttcg gcccgttggt tggtcaagtc ctggtcgtcg    14340
gtgctgacgc gggcatagcc cagcaggcca gcggcggcgc tcttgttcat ggcgtaatgt    14400
ctccggttct agtcgcaagt attctacttt atgcgactaa aacacgcgac aagaaaacgc    14460
caggaaaagg gcagggcggc agcctgtcgc gtaacttagg acttgtgcga catgtcgttt    14520
tcagaagacg gctgcactga acgtcagaag ccgactgcac tatagcagcg gaggggttgg    14580
atcgacctcg acgtacccct gcctcgcgcg tttcggtgat gacggtgaaa acctctgaca    14640
catgcagctc ccggagacgg tcacagcttg tctgtaagcg gatgccggga gcagacaagc    14700
ccgtcagggc gcgtcagcgg gtgttggcgg gtgtcggggc gcagccatga cccagtcacg    14760
tagcgatagc ggagtgtata ctggcttaac tatgcggcat cagagcagat tgtactgaga    14820
gtgcaccata tgcggtgtga ataccgcac agatgcgtaa ggagaaaata ccgcatcagg    14880
cgctcttccg cttcctcgct cactgactcg ctgcgctcgg tcgttcggct gcggcgagcg    14940
gtatcagctc actcaaaggc ggtaatcggt tatccacaga atcaggggat aacgcaggaa    15000
agaacatgtg agcaaaaggc cagcaaaagg ccaggaaccg taaaaaggcc gcgttgctgg    15060 cgttttttcca taggctccgc ccccctgacg agcatcacaa aaatcgacgc tcaagtcaga    15120
ggtggcgaaa cccgacagga ctataaagat accaggcgtt tccccctgga agctccctcg    15180
tgcgctctcc tgttccgacc ctgccgctta ccggatacct gtccgccttt ctcccttcgg    15240
gaagcgtggc gctttctcat agctcacgct gtaggtatct cagttcggtg taggtcgttc    15300
gctccaagct gggctgtgtg cacgaacccc cgttcagcc cgaccgctgc gccttatccg    15360
gtaactatcg tcttgagtcc aacccggtaa gacacgactt atcgccactg gcagcagcca    15420
ctggtaacag gattagcaga gcgaggtatg taggcggtgc tacagagttc ttgaagtggt    15480
ggcctaacta cggctacact agaagaacag tatttggtat ctgcgctctg ctgaagccag    15540
ttaccttcgg aaaaagagtt ggtagctctt gatccggcaa acaaaccacc gctggtagcg    15600
gtggtttttt tgtttgcaag cagcagatta cgcgcagaaa aaaaggatct caagaagatc    15660
ctttgatctt ttctacgggg tctgacgctc agtggaacga aaactcacgt taagggattt    15720
tggtcatgag attatcaaaa aggatcttca cctagatcct tttcggcgtc cacatcaacg    15780
gcgtcggcgg cgactgccca ggcaagaccg agatgcaccg cgatatcttg ctgcgttcgg    15840
atattttcgt ggagttcccg ccacagaccc ggattgaagg cgagatccag caactcgcgc    15900
cagatcatcc tgtgacggaa ctttggcgcg tgatgactgg ccaggacgtc ggccgaaaga    15960
gcgacaagca gatcacgctt ttcgacagcg tcggatttgc gatcgaggat tttttcggcgc    16020 tgcgctacgt ccgcgaccgc gttgagggat caagccacag cagcccactc gaccttctag    16080
ccgacccaga cgagccaagg gatctttttg gaatgctgct ccgtcgtcag gctttccgac    16140
gtttgggtgg ttgaacagaa gtcattatcg cacggaatgc caagcactcc cgaggggaac    16200
cctgtggttg gcatgcacat acaaatggac gaacggataa accttttcac gcccttttaa    16260
atatccgatt attctaataa acgctctttt ctctta                             16296
```

<210> SEQ ID NO 15
<211> LENGTH: 707
<212> TYPE: DNA
<213> ORGANISM: Artificial Sequence
<220> FEATURE:

<223> OTHER INFORMATION: W pOp6 W promoter

<400> SEQUENCE: 15

```
ctagctgtag ttgtagaatg taaaatgtaa tgttgttgtt gtttgttgtt gttgttggta      60
attgttgtaa aaatacgcgc gtctagcttc agcgtgtcct ctccaaatga aatgaacttc     120
cttatataga ggaagggtct tgcgaagatc gatccactag tctttcaatt gtgagcgctc     180
acaattcttt ctcttccctt tcttctttct agtctagtct ttcaattgtg agcgctcaca     240
attctttctc ttccctttct tctttctagt ctagtctttc aattgtgagc gctcacaatt     300
ctttctcttc cctttcttct ttctagtcta gtctttcaat tgtgagcgct cacaattctt     360
tctcttccct ttcttctttc tagtctagtc tttcaattgt gagcgctcac aattctttct     420 cttcccttttc ttctttctag tctagtcttt caattgtgag cgctcacaat tctttctctt     480 cccttttcttc tttctagtct ttcaattgtg agcgctcaca attctttctc ttcccttttct     540 tctttctagc tccaccgcgg tggcggccgg ccgctctagt ggatcgatct tcgcaagacc     600
cttcctctat ataaggaagt tcatttcatt tggagaggac acgctgaagc tagacgcgcg     660
tatttttaca acaattacca acaacaacaa caaacaacaa caacatt                   707
```

<210> SEQ ID NO 16
<211> LENGTH: 2226
<212> TYPE: DNA
<213> ORGANISM: Artificial Sequence
<220> FEATURE:
<223> OTHER INFORMATION: cDNA of LhGR encoding SEQ ID NO: 17

<400> SEQUENCE: 16

```
atggctagtg aagctcgaaa aacaaagaaa aaaatcaaag ggattcagca agccactgca      60
ggagtctcac aagacacttc ggaaaatcct aacaaaacaa tagttcctgc agcattacca     120
cagctcaccc ctaccttggt gtcactgctg gaggtgattg aacccgaggt gttgtatgca     180
ggatatgata gctctgttcc agattcagca tggagaatta tgaccacact caacatgtta     240
ggtgggcgtc aagtgattgc agcagtgaaa tgggcaaagg cgataccagg cttcagaaac     300
ttacacctgg atgaccaaat gaccctgcta cagtactcat ggatgtttct catggcattt     360
gccctgggtt ggagatcata cagacaatca gtggaaacc tgctctgctt tgctcctgat     420
ctgattatta tgagcagag aatgtctcta ccctgcatgt atgaccaatg taaacacatg     480
ctgttcgtct cctctgagct ccagcgattg caggtatcct atgaagagta tctctgtatg     540
aaaaccttac tgcttctctc ctcagttcct aaggaaggtc tgaagagcca agagttattt     600
gatgagattc gaatgactta tatcaaagag ctaggaaaag ccatcgtcaa aagggaaggg     660
aactccagtc agaactggca acggttttac caactgacaa agcttctgga ctccatgcat     720
gaggtggttg agaatctcct tacctactgc ttccagacat ttttggataa gaccatgagt     780
attgaattcc cagagatgtt agctgaaatc atcactaatc agataccaaa gtactcaaac     840
ggtaatatca agaagcttct gtttcatcaa aaatctacta gcaaaccggt aacgttatac     900
gacgtcgctg aatacgccgg cgtttctcat caaaccgttt ctagagtggt taaccaggct     960
tcacatgtta gcgctaaaac ccgggaaaaa gttgaagctg ccatggctga gctcaactac     1020
atcccgaacc gtgttgcgca gcagctggct ggtaaacaaa gcttgctgat cggtgtcgcg     1080
acctcgagct tggccctgca cgcgcgtcg caaattgtcg cggcgattaa atctcgcgcc     1140
gatcaactgg gtgccagcgt ggtggtgtcg atggtagaac gaagcggcgt cgaagcctgt     1200
aaagcggcgg tgcacaatct tctcgcgcaa cgcgtcagtg ggctgatcat taactatccg     1260
```

-continued

```
ctggatgacc aggatgccat tgctgtggaa gctgcctgca ctaatgttcc ggcgttattt    1320
cttgatgtct ctgaccagac acccatcaac agtattattt tctcccatga agacggtacg    1380
cgactgggcg tggagcatct ggtcgcattg ggtcaccagc aaatcgcgct gttagcgggc    1440
ccattaagtt ctgtctcggc gcgtctgcgt ctggctggct ggcataaata tctcactcgc    1500
aatcaaattc agccgatagc ggaacgggaa ggcgactgga gtgccatgtc cggttttcaa    1560
caaaccatgc aaatgctgaa tgagggcatc gttcccactg cgatgctggt tgccaacgat    1620
cagatggcgc tgggcgcaat gcgcgccatt accgagtccg ggctgcgcgt tggtgcggat    1680
atctcggtag tgggatacga cgataccgaa gacagctcat gttatatccc gccgttaacc    1740
accatcaaac aggattttcg cctgctgggg caaaccagcg tggaccgctt gctgcaactc    1800
tctcagggcc aggcggtgaa gggcaatcag ctgttgcccg tctcactggt gaaaagaaaa    1860
accactagtg gatcggaatt cgccaatttt aatcaaagtg ggaatattgc tgatagctca    1920
ttgtccttca ctttcactaa cagtagcaac ggtccgaacc tcataacaac tcaaacaaat    1980
tctcaagcgc tttcacaacc aattgcctcc tctaacgttc atgataactt catgaataat    2040
gaaatcacgg ctagtaaaat tgatgatggt aataattcaa aaccactgtc acctggttgg    2100
acggaccaaa ctgcgtataa cgcgtttgga atcactacag ggatgtttaa taccactaca    2160
atggatgatg tatataacta tctattcgat gatgaagata ccccaccaaa cccaaaaaaa    2220
gagtaa                                                               2226
```

```
<210> SEQ ID NO 17
<211> LENGTH: 741
<212> TYPE: PRT
<213> ORGANISM: Artificial Sequence
<220> FEATURE:
<223> OTHER INFORMATION: LhGR protein

<400> SEQUENCE: 17

Met Ala Ser Glu Ala Arg Lys Thr Lys Lys Ile Lys Gly Ile Gln
1               5                   10                  15

Gln Ala Thr Ala Gly Val Ser Gln Asp Thr Ser Glu Asn Pro Asn Lys
            20                  25                  30

Thr Ile Val Pro Ala Ala Leu Pro Gln Leu Thr Pro Thr Leu Val Ser
        35                  40                  45

Leu Leu Glu Val Ile Glu Pro Glu Val Leu Tyr Ala Gly Tyr Asp Ser
    50                  55                  60

Ser Val Pro Asp Ser Ala Trp Arg Ile Met Thr Thr Leu Asn Met Leu
65                  70                  75                  80

Gly Gly Arg Gln Val Ile Ala Ala Val Lys Trp Ala Lys Ala Ile Pro
                85                  90                  95

Gly Phe Arg Asn Leu His Leu Asp Asp Gln Met Thr Leu Leu Gln Tyr
            100                 105                 110

Ser Trp Met Phe Leu Met Ala Phe Ala Leu Gly Trp Arg Ser Tyr Arg
        115                 120                 125

Gln Ser Ser Gly Asn Leu Leu Cys Phe Ala Pro Asp Leu Ile Ile Asn
    130                 135                 140

Glu Gln Arg Met Ser Leu Pro Cys Met Tyr Asp Gln Cys Lys His Met
145                 150                 155                 160

Leu Phe Val Ser Ser Glu Leu Gln Arg Leu Gln Val Ser Tyr Glu Glu
                165                 170                 175

Tyr Leu Cys Met Lys Thr Leu Leu Leu Leu Ser Ser Val Pro Lys Glu
```

-continued

```
               180             185             190
Gly Leu Lys Ser Gln Glu Leu Phe Asp Glu Ile Arg Met Thr Tyr Ile
           195             200             205
Lys Glu Leu Gly Lys Ala Ile Val Lys Arg Glu Gly Asn Ser Ser Gln
       210             215             220
Asn Trp Gln Arg Phe Tyr Gln Leu Thr Lys Leu Leu Asp Ser Met His
225             230             235             240
Glu Val Val Glu Asn Leu Leu Thr Tyr Cys Phe Gln Thr Phe Leu Asp
           245             250             255
Lys Thr Met Ser Ile Glu Phe Pro Glu Met Leu Ala Glu Ile Ile Thr
           260             265             270
Asn Gln Ile Pro Lys Tyr Ser Asn Gly Asn Ile Lys Lys Leu Leu Phe
       275             280             285
His Gln Lys Ser Thr Ser Lys Pro Val Thr Leu Tyr Asp Val Ala Glu
       290             295             300
Tyr Ala Gly Val Ser His Gln Thr Val Ser Arg Val Val Asn Gln Ala
305             310             315             320
Ser His Val Ser Ala Lys Thr Arg Glu Lys Val Glu Ala Ala Met Ala
           325             330             335
Glu Leu Asn Tyr Ile Pro Asn Arg Val Ala Gln Gln Leu Ala Gly Lys
           340             345             350
Gln Ser Leu Leu Ile Gly Val Ala Thr Ser Ser Leu Ala Leu His Ala
       355             360             365
Pro Ser Gln Ile Val Ala Ala Ile Lys Ser Arg Ala Asp Gln Leu Gly
       370             375             380
Ala Ser Val Val Val Ser Met Val Glu Arg Ser Gly Val Glu Ala Cys
385             390             395             400
Lys Ala Ala Val His Asn Leu Leu Ala Gln Arg Val Ser Gly Leu Ile
           405             410             415
Ile Asn Tyr Pro Leu Asp Asp Gln Asp Ala Ile Ala Val Glu Ala Ala
           420             425             430
Cys Thr Asn Val Pro Ala Leu Phe Leu Asp Val Ser Asp Gln Thr Pro
       435             440             445
Ile Asn Ser Ile Ile Phe Ser His Glu Asp Gly Thr Arg Leu Gly Val
       450             455             460
Glu His Leu Val Ala Leu Gly His Gln Gln Ile Ala Leu Leu Ala Gly
465             470             475             480
Pro Leu Ser Ser Val Ser Ala Arg Leu Arg Leu Ala Gly Trp His Lys
           485             490             495
Tyr Leu Thr Arg Asn Gln Ile Gln Pro Ile Ala Glu Arg Glu Gly Asp
           500             505             510
Trp Ser Ala Met Ser Gly Phe Gln Gln Thr Met Gln Met Leu Asn Glu
           515             520             525
Gly Ile Val Pro Thr Ala Met Leu Val Ala Asn Asp Gln Met Ala Leu
       530             535             540
Gly Ala Met Arg Ala Ile Thr Glu Ser Gly Leu Arg Val Gly Ala Asp
545             550             555             560
Ile Ser Val Val Gly Tyr Asp Asp Thr Glu Asp Ser Ser Cys Tyr Ile
           565             570             575
Pro Pro Leu Thr Thr Ile Lys Gln Asp Phe Arg Leu Leu Gly Gln Thr
           580             585             590
Ser Val Asp Arg Leu Leu Gln Leu Ser Gln Gly Gln Ala Val Lys Gly
           595             600             605
```

```
Asn Gln Leu Leu Pro Val Ser Leu Val Lys Arg Lys Thr Thr Ser Gly
    610             615             620
```

```
Ser Glu Phe Ala Asn Phe Asn Gln Ser Gly Asn Ile Ala Asp Ser Ser
625             630             635             640
```

```
Leu Ser Phe Thr Phe Thr Asn Ser Ser Asn Gly Pro Asn Leu Ile Thr
            645             650             655
```

```
Thr Gln Thr Asn Ser Gln Ala Leu Ser Gln Pro Ile Ala Ser Ser Asn
            660             665             670
```

```
Val His Asp Asn Phe Met Asn Asn Glu Ile Thr Ala Ser Lys Ile Asp
        675             680             685
```

```
Asp Gly Asn Asn Ser Lys Pro Leu Ser Pro Gly Trp Thr Asp Gln Thr
    690             695             700
```

```
Ala Tyr Asn Ala Phe Gly Ile Thr Thr Gly Met Phe Asn Thr Thr Thr
705             710             715             720
```

```
Met Asp Asp Val Tyr Asn Tyr Leu Phe Asp Asp Glu Asp Thr Pro Pro
            725             730             735
```

```
Asn Pro Lys Lys Glu
        740
```

```
<210> SEQ ID NO 18
<211> LENGTH: 717
<212> TYPE: DNA
<213> ORGANISM: Artificial Sequence
<220> FEATURE:
<223> OTHER INFORMATION: cDNA of tdTomato encoding SEQ ID NO: 19

<400> SEQUENCE: 18
atggtgagca agggcgagga ggtcatcaaa gagttcatgc gcttcaaggt gcgcatggag      60
ggctccatga acggccacga gttcgagatc gagggcgagg cgagggccg ccccctacgag     120 ggcacccaga ccgccaagct gaaggtgacc aagggcggcc ccctgccctt cgcctgggac     180
atcctgtccc cccagttcat gtacggctcc aaggcgtacg tgaagcaccc cgccgacatc     240
cccgattaca agaagctgtc cttccccgag ggcttcaagt gggagcgcgt gatgaacttc     300
gaggacggcg tctggtgac cgtgacccag gactcctccc tgcaggacgg cacgctgatc      360
tacaaggtga agatgcgcgg caccaacttc cccccgacg gccccgtaat gcagaagaag     420
accatgggct gggaggcctc caccgagcgc ctgtacccc gcgacggcgt gctgaagggc     480
gagatccacc aggccctgaa gctgaaggac ggcggccact acctggtgga gttcaagacc    540
atctacatgg ccaagaagcc cgtgcaactg cccggctact actacgtgga caccaagctg     600
gacatcacct cccacaacga ggactacacc atcgtggaac agtacgagcg ctccgagggc     660
cgccaccacc tgttcctgta cggcatggac gagctgtaca gtctagagg tacctga         717
```

```
<210> SEQ ID NO 19
<211> LENGTH: 238
<212> TYPE: PRT
<213> ORGANISM: Artificial Sequence
<220> FEATURE:
<223> OTHER INFORMATION: tdTomato protein

<400> SEQUENCE: 19

Met Val Ser Lys Gly Glu Glu Val Ile Lys Glu Phe Met Arg Phe Lys
1               5               10              15
```

```
Val Arg Met Glu Gly Ser Met Asn Gly His Glu Phe Glu Ile Glu Gly
            20              25              30
```

```
Glu Gly Glu Gly Arg Pro Tyr Glu Gly Thr Gln Thr Ala Lys Leu Lys
```

-continued

```
              35                40                45
Val Thr Lys Gly Gly Pro Leu Pro Phe Ala Trp Asp Ile Leu Ser Pro
    50                55                60

Gln Phe Met Tyr Gly Ser Lys Ala Tyr Val Lys His Pro Ala Asp Ile
65                70                75                80

Pro Asp Tyr Lys Lys Leu Ser Phe Pro Glu Gly Phe Lys Trp Glu Arg
                85                90                95

Val Met Asn Phe Glu Asp Gly Gly Leu Val Thr Val Thr Gln Asp Ser
            100               105               110

Ser Leu Gln Asp Gly Thr Leu Ile Tyr Lys Val Lys Met Arg Gly Thr
            115               120               125

Asn Phe Pro Pro Asp Gly Pro Val Met Gln Lys Lys Thr Met Gly Trp
    130               135               140

Glu Ala Ser Thr Glu Arg Leu Tyr Pro Arg Asp Gly Val Leu Lys Gly
145               150               155               160

Glu Ile His Gln Ala Leu Lys Leu Lys Asp Gly Gly His Tyr Leu Val
            165               170               175

Glu Phe Lys Thr Ile Tyr Met Ala Lys Lys Pro Val Gln Leu Pro Gly
            180               185               190

Tyr Tyr Tyr Val Asp Thr Lys Leu Asp Ile Thr Ser His Asn Glu Asp
            195               200               205

Tyr Thr Ile Val Glu Gln Tyr Glu Arg Ser Glu Gly Arg His His Leu
    210               215               220

Phe Leu Tyr Gly Met Asp Glu Leu Tyr Lys Ser Arg Gly Thr
225               230               235
```

<210> SEQ ID NO 20
<211> LENGTH: 515
<212> TYPE: DNA
<213> ORGANISM: Artificial Sequence
<220> FEATURE:
<223> OTHER INFORMATION: Ubiquitin intron

<400> SEQUENCE: 20

```
cgccgctcgt cctccccccc ccccctctc taccttctct agatcggcgt tccggtccat      60
ggttagggcc cggtagttct acttctgttc atgtttgtgt tagatccgtg tttgtgttag     120
atccgtgctg ctagcgttcg tacacggatg cgacctgtac gtcagacacg ttctgattgc     180
taacttgcca gtgtttctct ttggggaatc ctgggatggc tctagccgtt ccgcagacgg     240
gatcgatcta ggataggtat acatgttgat gtgggtttta ctgatgcata tacatgatgg     300
catatgcagc atctattcat atgctctaac cttgagtacc tatctattat aataaacaag     360
tatgttttat aattattttg atcttgatat acttggatga tggcatatgc agcagctata     420
tgtggatttt tttagccctg ccttcatacg ctatttattt gcttggtact gtttctttg      480 tcgatgctca ccctgttgtt tggtgttact ctgc                                 515
```

<210> SEQ ID NO 21
<211> LENGTH: 693
<212> TYPE: DNA
<213> ORGANISM: Artificial Sequence
<220> FEATURE:
<223> OTHER INFORMATION: double 35S promoter

<400> SEQUENCE: 21

```
gtctcagaag accaaagggc tattgagact tttcaacaaa gggtaatatc gggaaacctc      60
ctcggattcc attgcccagc tatctgtcac ttgatcaaaa ggacagtaga aaaggaaggt     120
```

-continued

```
ggcacctaca aatgccatca ttgcgataaa ggaaaggcta tcgttcaaga tgcctctgcc      180
gacagtggtc ccaaagatgg accccccaccc acgaggagca tcgtggaaaa agaagacgtt      240
ccaaccacgt cttcaaagca agtgaattga tgtgataaca tggtggagca cgacactctc      300
gtctactcca agaatatcaa agatacagtc tcagaagacc aaagggctat tgagactttt      360
caacaaaggg taatatcggg aaacctcctc ggattccatt gcccagctat cggtcacttg      420
atcaaaagga cagtagaaaa ggaaggtggc acctacaaat gccatcattg cgataaagga      480
aaggctatcg ttcaagatgc ctctgccgac agtggtccca aagatggacc cccacccacg      540
aggagcatcg tggaaaaaga agacgttcca accacgtctt caaagcaagt ggattgatgt      600
gatatctcca ctgacgtaag ggatgacgca caatcccact atccttcgca agaccttcc      660 tctatataag gaagttcatt tcatttggag agg                                   693
```

<210> SEQ ID NO 22
<211> LENGTH: 4075
<212> TYPE: DNA
<213> ORGANISM: Artificial Sequence
<220> FEATURE:
<223> OTHER INFORMATION: XVE/OLexA promoter system

<400> SEQUENCE: 22

```
ttttgcaaat agcttcacct atataatact tcatccattt tattagtaca tccatttagg       60
gtttagggtt aatggttttt atagactaat ttttttagta catctatttt attctatttt      120
agcctctaaa ttaagaaaac taaaactcta ttttagtttt tttatttaat aatttagata      180
taaaatagaa taaaataaag tgactaaaaa ttaaacaaat accctttaag aaattaaaaa      240
aactaaggaa acatttttct tgtttcgagt agataatgcc agcctgttaa acgccgtcga      300
tcgacgagtc taacggacac caaccagcga accagcagcg tcgcgtcggg ccaagcgaag      360
cagacggcac ggcatctctg tcgctgcctc tggacccctc tcgagagttc cgctccaccg      420
ttggacttgc tccgctgtcg gcatccagaa attgcgtggc ggagcggcag acgtgagccg      480
gcacggcagg cggcctcctc ctcctctcac ggcaccggca gctacggggg attcctttcc      540
caccgctcct tcgctttccc ttcctcgccc gccgtaataa atagacaccc cctccacacc      600
ctctttcccc aacctcgtgt tgttcggagc gcacacacac acaaccagat ctcccccaaa      660
tccacccgtc ggcacctccg cttcaaggta cgccgctcgt cctcccccccc cccccctctc      720 taccttctct agatcggcgt tccggtccat ggttagggcc cggtagttct acttctgttc      780
atgtttgtgt tagatccgtg tttgtgttag atccgtgctg ctagcgttcg tacacggatg      840
cgacctgtac gtcagacacg ttctgattgc taacttgcca gtgtttctct ttggggaatc      900
ctgggatggc tctagccgtt ccgcagacgg gatcgatcta ggataggtat acatgttgat      960
gtgggtttta ctgatgcata tacatgatgg catatgcagc atctattcat atgctctaac     1020
cttgagtacc tatctattat aataaacaag tatgtttttat aattattttg atcttgatat     1080
acttggatga tggcatatgc agcagctata tgtggatttt tttagccctg ccttcatacg     1140
ctatttattt gcttggtact gtttcttttg tcgatgctca ccctgttgtt ggtgttact     1200 tctgcaggta ctagtattcc gggcggaatg aaagcgttaa cggccaggca acaagaggtg     1260
tttgatctca tccgtgatca catcagccag acaggtatgc cgccgacgcg tgcggaaatc     1320
gcgcagcgtt tggggttccg ttccccaaac gcggctgaag aacatctgaa ggcgctggca     1380
cgcaaaggcg ttattgaaat tgtttccggc gcatcacgcg ggattcgtct gttgcaggaa     1440
```

```
gaggaagaag ggttgccgct ggtaggtcgt gtggctgccg gtgaaccgtc gagcgccccc    1500
ccgaccgatg tcagcctggg ggacgagctc cacttagacg gcgaggacgt ggcgatggcg    1560
catgccgacg cgctagacga tttcgatctg gacatgttgg gggacgggga ttccccgggt    1620
ccgggattta ccccccacga ctccgccccc tacggcgctc tggatatggc cgacttcgag    1680
tttgagcaga tgtttaccga tgcccttgga attgacgagt acggtgggga tccgtctgct    1740
ggagacatga gagctgccaa cctttggcca agcccgctca tgatcaaacg ctctaagaag    1800
aacagcctgg ccttgtccct gacggccgac cagatggtca gtgccttgtt ggatgctgag    1860
ccccccatac tctattccga gtatgatcct accagaccct tcagtgaagc ttcgatgatg    1920
ggcttactga ccaacctggc agacagggag ctggttcaca tgatcaactg ggcgaagagg    1980
gtgccaggct ttgtggattt gaccctccat gatcaggtcc accttctaga atgtgcctgg    2040
ctagagatcc tgatgattgg tctcgtctgg cgctccatgg agcacccagg gaagctactg    2100
tttgctccta acttgctctt ggacaggaac cagggaaaat gtgtagaggg catggtggag    2160
atcttcgaca tgctgctggc tacatcatct cggttccgca tgatgaatct gcagggagag    2220
gagtttgtgt gcctcaaatc tattattttg cttaattctg gagtgtacac atttctgtcc    2280
agcaccctga agtctctgga agagaaggac catatccacc gagtcctgga caagatcaca    2340
gacactttga tccacctgat ggccaaggca ggcctgaccc tgcagcagca gcaccagcgg    2400
ctggcccagc tcctcctcat cctctcccac atcaggcaca tgagtaacaa aggcatggag    2460
catctgtaca gcatgaagtg caagaacgtg gtgcccctct atgacctgct gctggagatg    2520
ctggacgccc accgcctaca tgcgcccact agccgtggag gggcatccgt ggaggagacg    2580
gaccaaagcc acttggccac tgcgggctct acttcatcgc attccttgca aaagtattac    2640
atcacggggg aggcagaggg tttccctgcc acagtctgag agctccctgg cggaattccc    2700
agagatgtta gctgaaatca tcactaatca gataccaaaa tattcaaatg gaaatatcaa    2760
aaagcttctg tttcatcaaa aatgactcga cctaactgag taagctagct tgttcgagta    2820
ttatggcatt gggaaaactg ttttttcttgt accatttgtt gtgcttgtaa tttactgtgt    2880
tttttattcg gttttcgcta tcgaactgtg aaatggaaat ggatggagaa gagttaatga    2940
atgatatggt ccttttgttc attctcaaat taatattatt tgtttttttct cttatttgtt    3000 gtgtgttgaa tttgaaatta taagagatat gcaaacattt tgttttgagt aaaaatgtgt    3060
caaatcgtgg cctctaatga ccgaagttaa tatgaggagt aaaacactag atccccaaac    3120
aagcttggaa actgaaggcg ctcgagttac tagatcgggg aattgatccc ccctcgacag    3180
cttgcatgcc gcttgggctg caggtcgagg ctaaaaaact aatcgcatta tcatcccctc    3240
gacgtactgt acatataacc actggtttta tatacagcag tactgtacat ataaccactg    3300
gttttatata cagcagtcga cgtactgtac atataaccac tggttttata tacagcagta    3360
ctgtacatat aaccactggt tttatataca gcagtcgagg taagattaga tatggatatg    3420
tatatggata tgtatatggt ggtaatgcca tgtaatatgc tcgactctag gatcttcgca    3480
agacccttcc tctatataag gaagttcatt tcatttggag aggacacgct gaagctagtc    3540
gactctagcc tccctaggct gccggacgac gagctcctcc ccctcccccc tccgccgccg    3600
ccgcgccggt aaccaccccg cccctctcct ctttctttct ccgttttttt ttccgtctcg    3660
gtctcgatct ttggccttgg tagtttgggt gggcgagagg cggcttcgtg cgcgcccaga    3720
tcggtgcgcg ggaggggcgg gatctcgcgg ctggggctct cgccggcgtg gatccggccc    3780
ggatctcgcg gggaatgggg ctctcggatg tagatctgcg atccgccgtt gttgggggag    3840
```

-continued

```
atgatggggg gtttaaaatt tccgccatgc taaacaagat caggaagagg ggaaaagggc      3900
actatggttt atatttttat atatttctgc tgcttcgtca ggcttagatg tgctagatct      3960
tcttctttct ttcttctttt tgtgggtaga atttgaatcc ctcagcattg ttcatcggta      4020
gttttctttt tcatgatttg tgacaaatgc agcctcgtgc ggagcttttt tgtag          4075
```

```
<210> SEQ ID NO 23
<211> LENGTH: 687
<212> TYPE: DNA
<213> ORGANISM: Zea mays

<400> SEQUENCE: 23
ttttgcaaat agcttcacct atataatact tcatccattt tattagtaca tccatttagg        60
gtttagggtt aatggttttt atagactaat tttttttagta catctatttt attctatttt      120
agcctctaaa ttaagaaaac taaaactcta ttttagtttt tttatttaat aatttagata       180
taaaatagaa taaaataaag tgactaaaaa ttaaacaaat accctttaag aaattaaaaa       240
aactaaggaa acatttttct tgtttcgagt agataatgcc agcctgttaa acgccgtcga       300
tcgacgagtc taacggacac caaccagcga accagcagcg tcgcgtcggg ccaagcgaag       360
cagacggcac ggcatctctg tcgctgcctc tggacccctc tcgagagttc cgctccaccg       420
ttggacttgc tccgctgtcg gcatccagaa attgcgtggc ggagcggcag acgtgagccg       480
gcacggcagg cggcctcctc ctcctctcac ggcaccggca gctacggggg attcctttcc       540
caccgctcct tcgctttccc ttcctcgccc gccgtaataa atagacaccc cctccacacc       600
ctctttcccc aacctcgtgt tgttcggagc gcacacacac acaaccagat ctcccccaaa       660
tccacccgtc ggcacctccg cttcaag                                           687
```